United States Patent
Kinsho et al.

(10) Patent No.: US 8,791,288 B2
(45) Date of Patent: Jul. 29, 2014

(54) ACID-LABILE ESTER MONOMER HAVING SPIROCYCLIC STRUCTURE, POLYMER, RESIST COMPOSITION, AND PATTERNING PROCESS

(75) Inventors: Takeshi Kinsho, Joetsu (JP); Tomohiro Kobayashi, Joetsu (JP); Masayoshi Sagehashi, Joetsu (JP); Takeru Watanabe, Joetsu (JP); Koji Hasegawa, Joetsu (JP); Seiichiro Tachibana, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 373 days.

(21) Appl. No.: 12/787,004

(22) Filed: May 25, 2010

(65) Prior Publication Data
US 2010/0304295 A1 Dec. 2, 2010

Related U.S. Application Data

(60) Provisional application No. 61/181,084, filed on May 26, 2009.

(51) Int. Cl.
*C07C 69/54* (2006.01)
*C08F 22/10* (2006.01)
*G03F 7/004* (2006.01)
*G03F 7/039* (2006.01)
*G03F 7/26* (2006.01)

(52) U.S. Cl.
USPC ........ 560/220; 526/318; 430/270.1; 430/326; 430/910

(58) Field of Classification Search
USPC ............... 430/270.1, 326, 908, 910; 526/318; 560/18, 32, 64, 104, 220
See application file for complete search history.

(56) References Cited

U.S. PATENT DOCUMENTS

| | | | |
|---|---|---|---|
| 6,248,920 B1 * | 6/2001 | Takechi et al. | 560/116 |
| 6,280,898 B1 | 8/2001 | Hasegawa et al. | |
| 6,312,867 B1 | 11/2001 | Kinsho et al. | |
| 6,329,125 B2 | 12/2001 | Takechi et al. | |
| 6,448,420 B1 | 9/2002 | Kinsho et al. | |
| 6,830,866 B2 | 12/2004 | Kobayashi et al. | |
| 6,946,233 B2 | 9/2005 | Nishi et al. | |
| 2008/0085469 A1 * | 4/2008 | Ohsawa et al. | 430/286.1 |
| 2009/0023878 A1 | 1/2009 | Maeda et al. | |

FOREIGN PATENT DOCUMENTS

| | | | |
|---|---|---|---|
| JP | 9-073173 A | 3/1997 | |
| JP | 9-090637 A | 4/1997 | |
| JP | 2000-026446 A | 1/2000 | |
| JP | 2000-159758 A | 6/2000 | |
| JP | 2000-327633 A | 11/2000 | |
| JP | 2000-336121 A | 12/2000 | |
| JP | 2003-066612 A | 3/2003 | |
| JP | 2003-113213 A | 4/2003 | |
| JP | 2009-063889 | * 3/2009 | |

OTHER PUBLICATIONS

Machine translation of JP 2009-063889, published on Mar. 26, 2009.*
Michael J. Burke, Murray M. Allan, Masood Parvez and Brian A. Keay—Synthesis and applications of (1R,5S,6S)-6-(2,2-dimethylpropanamido)spiro(4.4)nonan-1-ol as a chiral auxiliary in Diels-Alder reactions, Tetrahedron: Asymmetry 11(2000), pp. 2733-2739.*
Koji Arimitsu et al. "Sensitivity Enhancement of Chemical-Amplification-Type Photoimaging Materials by Acetoacetic Acid Derivatives", Journal of Photopolymer Science and Technology, 1995, 43-46, vol. 8 Issue 1.
Koji Arimitsu et al."Effect of Phenolic Hydroxyl Residues on the Improvement of Acid-Proliferation-Type Photoimaging Materials", Journal of Photopolymer Science and Technology, 1996, 29-30, vol. 9 Issue 1.
M. Maenhoudt et al. "Double Patterning Scheme for Sub-0.25 k1 Single Damascene Structures at NA=0.75, λ=193nm", Proceedings of SPIE, p. 1508, vol. 5754.
Masato Shibuya et al. "Performance of Resolution Enhancement Technique Using Both Multiple Exposure and Nonlinear Resist", Japanese Journal of Applied Physics, Dec. 1994, p. 6874-77, vol. 33, Part 1, No. 12B.

(Continued)

*Primary Examiner* — Anca Eoff
(74) *Attorney, Agent, or Firm* — Westerman, Hattori, Daniels & Adrian, LLP

(57) ABSTRACT

An acid-labile ester monomer of spirocyclic structure has formula (1) wherein Z is a monovalent group having a polymerizable double bond, X is a divalent group which forms a cyclopentane, cyclohexane or norbornane ring, $R^2$ is H or monovalent hydrocarbon, $R^3$ and $R^4$ are H or monovalent hydrocarbon, or $R^3$ and $R^4$, taken together, stand for a divalent group which forms a cyclopentane or cyclohexane ring, and n is 1 or 2. A polymer obtained from the acid-labile ester monomer has so high reactivity in acid-catalyzed elimination reaction that the polymer may be used to formulate a resist composition having high resolution.

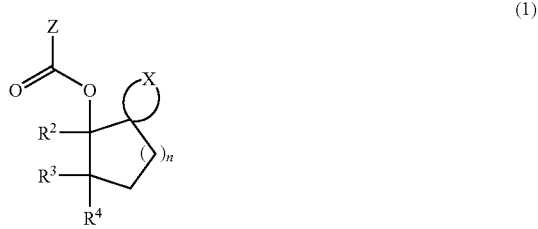

(1)

11 Claims, No Drawings

(56) References Cited

OTHER PUBLICATIONS

A. Paul Krapcho, "Synthesis of Carbocyclic Spiro Compounds via Intramolecular Alkylation Routes", Synthesis, Jun. 1974, 383-419.

Vinayak V. Kane et al. "Spiro[5.7] Trideca-1,4-Dien-3-One", Organic Syntheses, p. 472-75, Collective vol. 7.

Walter F. Gannon et al. "3-Ethoxy-2-Cyclohexenone", Organic Syntheses, p. 538-41, Collective vol. 5.

* cited by examiner

ACID-LABILE ESTER MONOMER HAVING SPIROCYCLIC STRUCTURE, POLYMER, RESIST COMPOSITION, AND PATTERNING PROCESS

CROSS REFERENCE TO RELATED APPLICATION

This application is an application filed under 35 U.S.C. 111(a) claiming benefit pursuant to 35 U.S.C §119(e)(i) of the filing date of the Provisional Application 61/181,084 filed on May 26, 2009 pursuant to 35 U.S.C. §111(b).

TECHNICAL FIELD

This invention relates to novel acid-labile ester monomers having spirocyclic structure, useful as reactants for the synthesis of functional materials. The monomers are useful in preparing polymers which are used as a base resin to formulate a radiation-sensitive resist composition which has high transparency to radiation with a wavelength of up to 500 nm, especially up to 300 nm, e.g., KrF laser, ArF laser or $F_2$ laser light, and when processed by lithography, generates a carboxylic acid through elimination reaction in the presence of acid and exhibits good resolution and development characteristics. The invention also relates to polymers comprising recurring units derived from the acid-labile ester monomers having spirocyclic structure, photoresist compositions comprising the polymers, and pattern forming processes using the photoresist compositions.

BACKGROUND ART

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 µm or less. These lithography processes use resist materials comprising various alkali-soluble resins as the base resin.

For resist materials for use in the KrF laser lithography, in fact, polyhydroxystyrene resins become the standard. For ArF resist materials, studies are made on poly(meth)acrylate resins utilizing carboxyl groups as the alkali soluble group and polymers of cycloaliphatic olefins such as norbornene. Of these, poly(meth)acrylate resins are practically used because of ease of polymerization.

As for the poly(meth)acrylate, JP-A 9-90637 proposes a combination of methyladamantyl(meth)acrylate as acid labile group-containing recurring units (or acid labile units) with lactone ring-containing (meth)acrylate as adhesive group-containing recurring units. JP-A 9-73173 discloses an acid labile group having a tertiary alkyl radical of alkylcycloalkyl form. JP-A 2000-327633 discloses an acid labile group having an exo-isomer of a tertiary alkyl group of alkylbicyclo[2.2.1]heptanol form. This acid labile group is easily acid eliminatable, requires only low activation energy for acid elimination, and provides for a high resolution and less PEB dependence. As the adhesive groups with enhanced etching resistance, JP-A 2000-26446 and JP-A 2000-159758 propose (meth)acrylate units having norbornane-lactone and oxanorbornane-lactone, respectively. These works resulted in ArF resist materials having significantly improved resolution. Also, JP-A 2003-113213 discloses a ternary polymer comprising acid labile units, lactone units, and hydroxyl-containing recurring units as derived from 3-hydroxy-1-adamantyl (meth)acrylate, for controlling the diffusion within a resist film of the acid generated by the photoacid generator upon exposure. This polymer is also used as a base resin in resist materials.

With respect to acid-catalyzed elimination reaction within the resist film, if acid labile units have high elimination reactivity, elimination reaction can take place even at low temperature. This allows for a lower PEB temperature, restraining thermal diffusion of acid during the PEB process. If the acid labile units are endowed with an appropriate fat solubility, the dose-dependent contrast of dissolution rate in developer may be increased. The low acid diffusion and high contrast contribute to an improvement in resolution, that is, enhancements of various process margins such as exposure latitude (EL), depth of focus (DOF), and mask fidelity in forming a fine size pattern. They are also effective for minimizing the pattern roughness (i.e., line edge roughness (LER) or line width roughness (LWR) in the case of line-and-space patterns or circularity in the case of hole patterns). Acid labile units having high elimination reactivity are expected to reduce the PEB temperature dependency of pattern size and to minimize dimensional variations caused by a slight difference of thermal history between different positions on the wafer surface. For these reasons, there is a need for acid labile units having an appropriate fat solubility as well as high elimination reactivity.

CITATION LIST

Patent Document 1: JP-A H09-90637
Patent Document 2: JP-A H09-73173
Patent Document 3: JP-A 2000-327633 (U.S. Pat. No. 6,448,420)
Patent Document 4: JP-A 2000-26446
Patent Document 5: JP-A 2000-159758 (U.S. Pat. No. 6,280,898)
Patent Document 6: JP-A 2003-113213

SUMMARY OF INVENTION

The invention aims to establish a resist composition which features a high resolution and reduced PEB temperature dependence, when processed by photolithography using high-energy radiation such as ArF excimer laser light as the light source. An object of the invention is to provide an acid-labile ester monomer having spirocyclic structure which is useful in forming a polymer as the base resin, a polymer derived from the acid-labile ester monomer having spirocyclic structure, a resist composition comprising the polymer as the base resin, and a pattern forming process using the same.

The inventors have found that an acid-labile ester monomer having spirocyclic structure is useful in preparing a polymer which serves as a resist base resin. More particularly, the inventors have found that an acid-labile ester monomer having spirocyclic structure as represented by the general formula (1) can be readily prepared, that a polymer obtained from this monomer is a useful base resin to formulate a resist composition, and that the resulting resist composition has a high contrast and is advantageously used in precise micropatterning.

In a first aspect, the invention provides an acid-labile ester monomer having spirocyclic structure represented by the general formula (1) or formula (2) or (3).

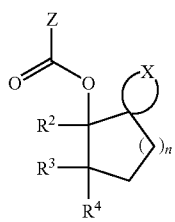
(1)

Herein Z is a monovalent group having a polymerizable double bond, X is a divalent group which forms a substituted or unsubstituted cyclopentane, cyclohexane or norbornane ring with the carbon atom to which it is attached, $R^2$ is hydrogen or a straight, branched or cyclic $C_1$-$C_{10}$ monovalent hydrocarbon group, $R^3$ and $R^4$ are each independently hydrogen or a straight, branched or cyclic $C_1$-$C_{10}$ monovalent hydrocarbon group, or $R^3$ and $R^4$, taken together, stand for a divalent group which forms a substituted or unsubstituted cyclopentane or cyclohexane ring with the carbon atom to which they are attached, and n is 1 or 2.

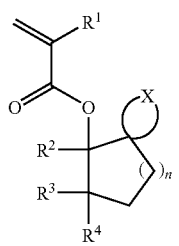
(2)

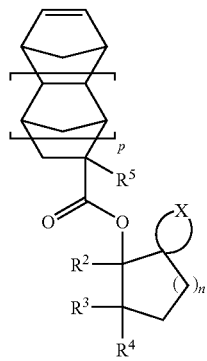
(3)

Herein X is a divalent group which forms a substituted or unsubstituted cyclopentane, cyclohexane or norbornane ring with the carbon atom to which it is attached, $R^1$ is hydrogen, fluorine, methyl or trifluoromethyl, $R^2$ is hydrogen or a straight, branched or cyclic $C_1$-$C_{10}$ monovalent hydrocarbon group, $R^3$ and $R^4$ are each independently hydrogen or a straight, branched or cyclic $C_1$-$C_{10}$ monovalent hydrocarbon group, or $R^3$ and $R^4$, taken together, stand for a divalent group which forms a substituted or unsubstituted cyclopentane or cyclohexane ring with the carbon atom to which they are attached, $R^5$ is hydrogen or methyl, n is 1 or 2, and p is 0 or 1.

In a second aspect, the invention provides a polymer comprising recurring units having the general formula (1a), (2a) or (3a), which are derived from the acid-labile ester monomer having a spirocyclic structure.

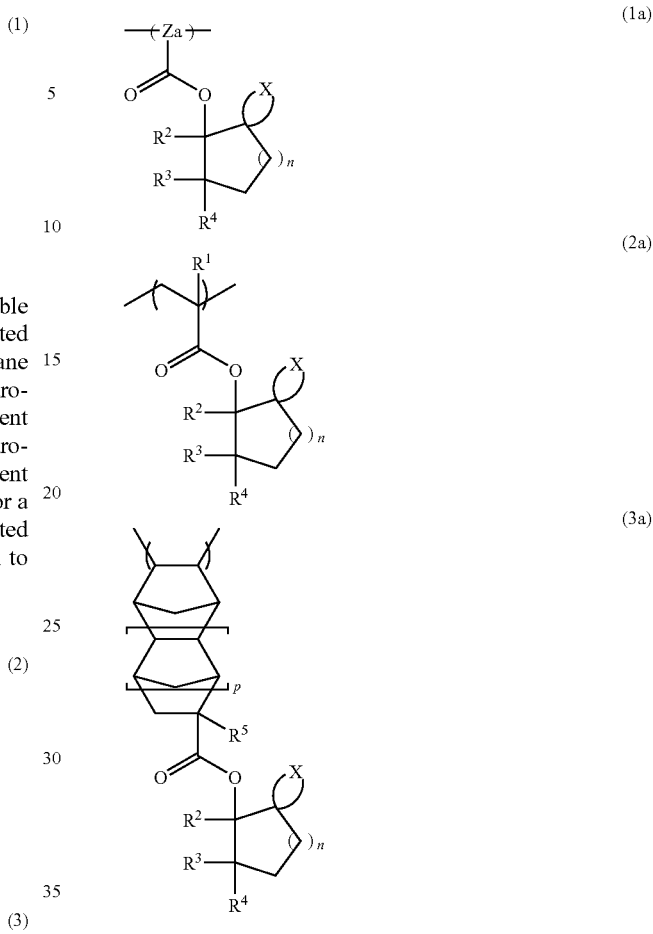

Herein Za is a trivalent group derived by polymerization from a monovalent group Z having a polymerizable double bond. X, $R^1$, $R^2$, $R^3$, $R^4$, $R^5$, n and p are as defined above.

In a third aspect, the invention provides a resist composition comprising the polymer defined above as a base resin and a compound capable of generating an acid in response to actinic light or radiation.

In a preferred embodiment, the compound capable of generating an acid in response to actinic light or radiation is a sulfonium salt compound having the general formula (4).

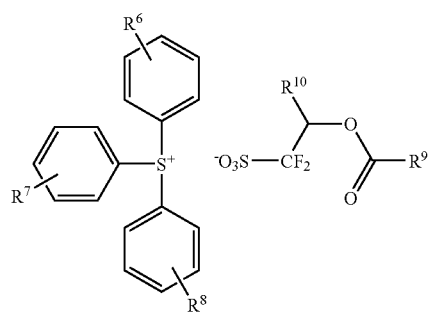
(4)

Herein $R^6$, $R^7$, and $R^8$ are each independently hydrogen, a straight, branched or cyclic $C_1$-$C_{20}$ monovalent hydrocarbon group which may contain a heteroatom, $C_1$-$C_{10}$ alkoxy group or halogen, $R^9$ is a straight, branched or cyclic $C_1$-$C_{30}$ monovalent hydrocarbon group which may contain a heteroatom, and $R^{10}$ is hydrogen or trifluoromethyl.

In a fourth aspect, the invention provides a process for forming a pattern, comprising the steps of applying the resist composition defined above onto a substrate, heat treating, exposing to high-energy radiation or electron beam through a photomask, optionally heat treating, and developing with a developer.

Advantageous Effect of Invention

The acid-labile ester monomers having spirocyclic structure are useful as reactants for the synthesis of functional materials, typically polymers which have high transparency to radiation with a wavelength of up to 500 nm, especially up to 300 nm, and very high reactivity in acid-catalyzed elimination reaction so that the polymers may be used as a base resin to formulate a radiation-sensitive resist composition having a high resolution. The polymers are useful base resins in radiation-sensitive resist compositions. The resist compositions have many advantages including a high resolution, excellent properties of exposure latitude, depth of focus, and mask fidelity, and minimized roughness. The PEB temperature dependence of pattern size is reduced. All these contribute to an improvement in the yield of actual production.

DESCRIPTION OF EMBODIMENTS

The singular forms "a," "an" and "the" include plural referents unless the context clearly dictates otherwise. "Optional" or "optionally" means that the subsequently described event or circumstance may or may not occur, and that the description includes instances where the event occurs and instances where it does not. As used herein, the notation ($C_n$-$C_m$) means a group containing from n to m carbon atoms per group. The term "monomer" refers to a polymerizable compound.

The abbreviations and acronyms have the following meaning.
  Mw: weight average molecular weight
  Mn: number average molecular weight
  Mw/Mn: molecular weight distribution or dispersity
  GPC: gel permeation chromatography
  PEB: post-exposure baking
  TMAH: tetramethylammonium hydroxide
  PGMEA: propylene glycol monomethyl ether acetate It is understood that for many structures represented by chemical formulae, there can exist enantiomers and diastereomers. Unless otherwise stated, a single formula collectively represents all such stereoisomers. The stereoisomers may be used alone or in admixture.

Monomer

The acid-labile ester monomer having a spirocyclic structure of the invention has the general formula (1).

Herein Z is a monovalent group having a polymerizable double bond. X is a divalent group which forms a substituted or unsubstituted cyclopentane, cyclohexane or norbornane ring with the carbon atom to which it is attached. $R^2$ is hydrogen or a straight, branched or cyclic $C_1$-$C_{10}$ monovalent hydrocarbon group. $R^3$ and $R^4$ are each independently hydrogen or a straight, branched or cyclic $C_1$-$C_{10}$ monovalent hydrocarbon group, or $R^3$ and $R^4$, taken together, stand for a divalent group which forms a substituted or unsubstituted cyclopentane or cyclohexane ring with the carbon atom to which they are attached. The subscript n is 1 or 2.

Specifically, Z is a monovalent group having a polymerizable double bond. Examples include groups containing a multiple bond such as vinyl, ethynyl, 1-propenyl, isopropenyl, 3,3,3-trifluoro-2-propenyl, allyl, 1,3-butadienyl, 2-methyl-1-propenyl, 5-norbornen-2-yl, and tetracyclo[4.4.0.1$^{2,5}$.1$^{7,10}$]dodec-8-en-3-yl; or groups containing an acrylic acid ester, methacrylic acid ester, α-trifluoromethylacrylic acid ester, vinyl ether, allyl ether, norbornene, tricyclo[5.2.1.0$^{2,6}$]decene, or tetracyclo[4.4.0.1$^{2,5}$.1$^{7,10}$]dodecene as a partial structure, such as acryloyloxymethyl, methacryloyloxymethyl, α-trifluoromethylacryloylmethyl, 1-(acryloyloxy)ethyl, 1-(methacryloyloxy)ethyl, 1-(α-trifluoromethylacryloyloxy)ethyl, 2-(acryloyloxy)ethyl, 2-(methacryloyloxy)ethyl, 2-(α-trifluoromethylacryloyloxy)ethyl, 3-(acryloyloxy)propyl, 3-(methacryloyloxy)propyl, 3-(α-trifluoromethylacryloyloxy)propyl, 4-(acryloyloxy)butyl, 4-(methacryloyloxy)butyl, 3-(α-trifluoromethylacryloyloxy)butyl, 2-vinyloxyethyl, 2-vinyloxypropyl, 3-vinyloxypropyl, 2-allyloxyethyl, 2-allyloxypropyl, 3-allyloxypropyl, 5-norbornene-2-carbonyloxymethyl, 2-(5-norbornene-2-carbonyloxy)ethyl, 5-norbornen-2-ylmethyl, 2-(5-norbornen-2-yl)ethyl, 5-acryloyloxynorbornane-2-carbonyloxymethyl, 2-(5-acryloyloxynorbornane-2-carbonyloxy)ethyl, 5-acryloyloxynorbornan-2-ylmethyl, 2-(5-acryloyloxynorbornan-2-yl)ethyl, 5-methacryloyloxynorbornane-2-carbonyloxymethyl, 2-(5-methacryloyloxynorbornane-2-carbonyloxy)ethyl, 5-methacryloyloxynorbornan-2-ylmethyl, 2-(5-methacryloyloxynorbornan-2-yl)ethyl, 5-(α-trifluoromethylacryloyloxy)norbornane-2-carbonyloxymethyl, 2-(5-(α-trifluoromethylacryloyloxy)norbornane-2-carbonyloxy)-ethyl, 5-(α-trifluoromethylacryloyloxy)norbornan-2-ylmethyl, 2-(5-(α-trifluoromethylacryloyloxy)norbornan-2-yl)ethyl, (tricyclo[5.2.1.0$^{2,6}$]dec-8-ene-4-carbonyloxy)methyl, 2-(tricyclo[5.2.1.0$^{2,6}$]dec-8-ene-4-carbonyloxy)ethyl, (tetracyclo[4.4.0.1$^{2,5}$.1$^{7,10}$]dodec-8-ene-3-carbonyloxy)methyl, and 2-(tetracyclo[4.4.0.1$^{2,5}$.1$^{7,10}$]dodec-8-ene-3-carbonyloxy)-ethyl.

Of these, preferred are vinyl, isopropenyl, 3,3,3-trifluoro-2-propenyl, 5-norbornen-2-yl, and tetracyclo[4.4.0.1$^{2,5}$.1$^{7,10}$]dodec-8-en-3-yl. In these cases, the acid-labile ester monomers having a spirocyclic structure of the invention are represented by the general formulae (2) and (3).

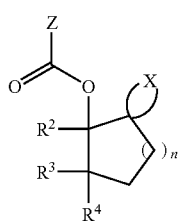

(1)

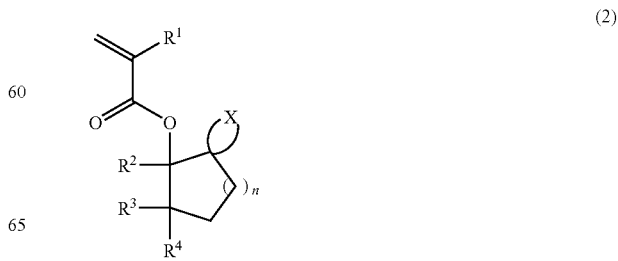

(2)

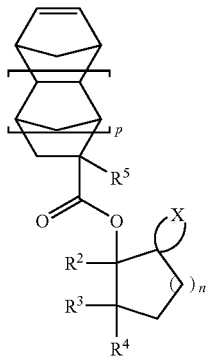

(3)

Herein X is a divalent group which forms a substituted or unsubstituted cyclopentane, cyclohexane or norbornane ring with the carbon atom to which it is attached. $R^1$ is hydrogen, fluorine, methyl or trifluoromethyl. $R^2$ is hydrogen or a straight, branched or cyclic $C_1$-$C_{10}$ monovalent hydrocarbon group. $R^3$ and $R^4$ are each independently hydrogen or a straight, branched or cyclic $C_1$-$C_{10}$ monovalent hydrocarbon group, or $R^3$ and $R^4$, taken together, stand for a divalent group which forms a substituted or unsubstituted cyclopentane or cyclohexane ring with the carbon atom to which they are attached. $R^5$ is hydrogen or methyl. The subscript n is 1 or 2, and p is 0 or 1.

Specifically, X is a divalent group which forms a substituted or unsubstituted cyclopentane, cyclohexane or norbornane ring with the carbon atom to which it is attached. Namely, the partial structure:

(wherein the broken line designates a valence bond) stands for a substituted or unsubstituted cyclopentane, cyclohexane or norbornane ring, i.e., a cyclic structure represented by the partial structure:

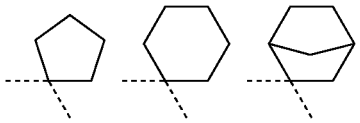

(wherein the broken line designates a valence bond), or a fused ring containing the foregoing. One or more hydrogen atom in these structures may be replaced by $C_1$-$C_3$ alkyl, hydroxyl (—OH) or halogen atom, and one or more methylene moiety (—CH$_2$—) may be replaced by a carbonyl group (—(C=O)—) or heteroatom such as oxygen (—O—).

$R^2$ is hydrogen or a straight, branched or cyclic $C_1$-$C_{10}$ monovalent hydrocarbon group. Examples of the monovalent hydrocarbon group include, but are not limited to, methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, ethyltetracyclo[4.4.0.1$^{2,5}$.1$^{7,10}$]dodecylethyl, phenyl, tolyl and naphthyl. These groups may contain an unsaturated bond. Of these monovalent hydrocarbon groups $R^2$, methyl, ethyl, propyl, isopropyl and n-butyl are preferred.

$R^3$ and $R^4$ are each independently hydrogen or a straight, branched or cyclic $C_1$-$C_{10}$ monovalent hydrocarbon group. Examples of the straight, branched or cyclic $C_1$-$C_{10}$ monovalent hydrocarbon groups represented by $R^3$ and $R^4$ are as exemplified for $R^2$. Preferably $R^3$ and $R^4$ are hydrogen or methyl. Alternatively, $R^3$ and $R^4$, taken together, may form a substituted or unsubstituted cyclopentane or cyclohexane ring with the carbon atom to which they are attached, or a fused ring containing such a ring. In these structures, one or more hydrogen atom may be replaced by $C_1$-$C_3$ alkyl, hydroxyl (—OH) or halogen atom, and one or more methylene moiety (—CH$_2$—) may be replaced by a carbonyl group or heteroatom such as oxygen (—O—).

Examples of the acid-labile ester monomer having a spirocyclic structure of the invention are given below, but not limited thereto.

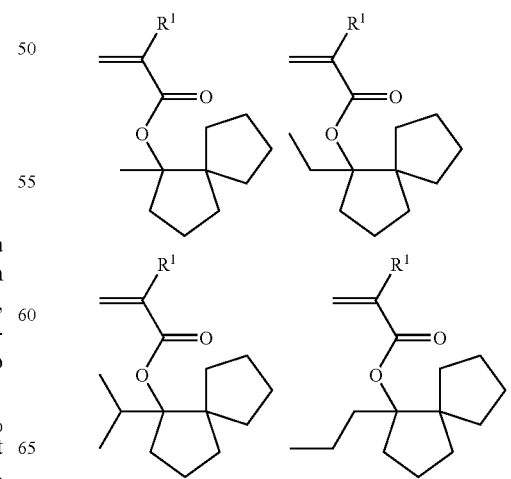

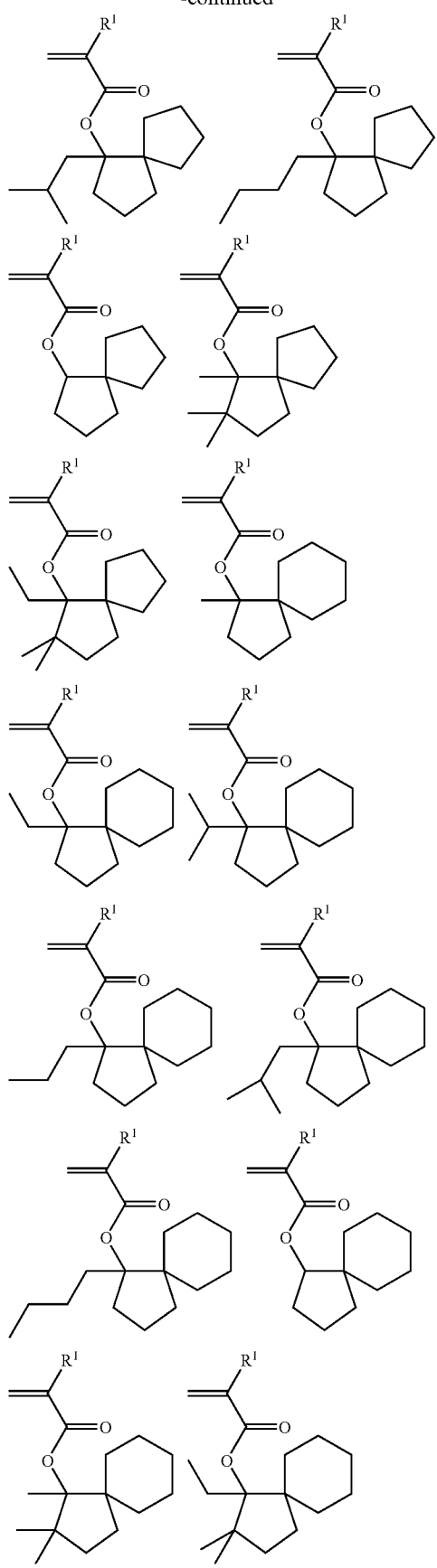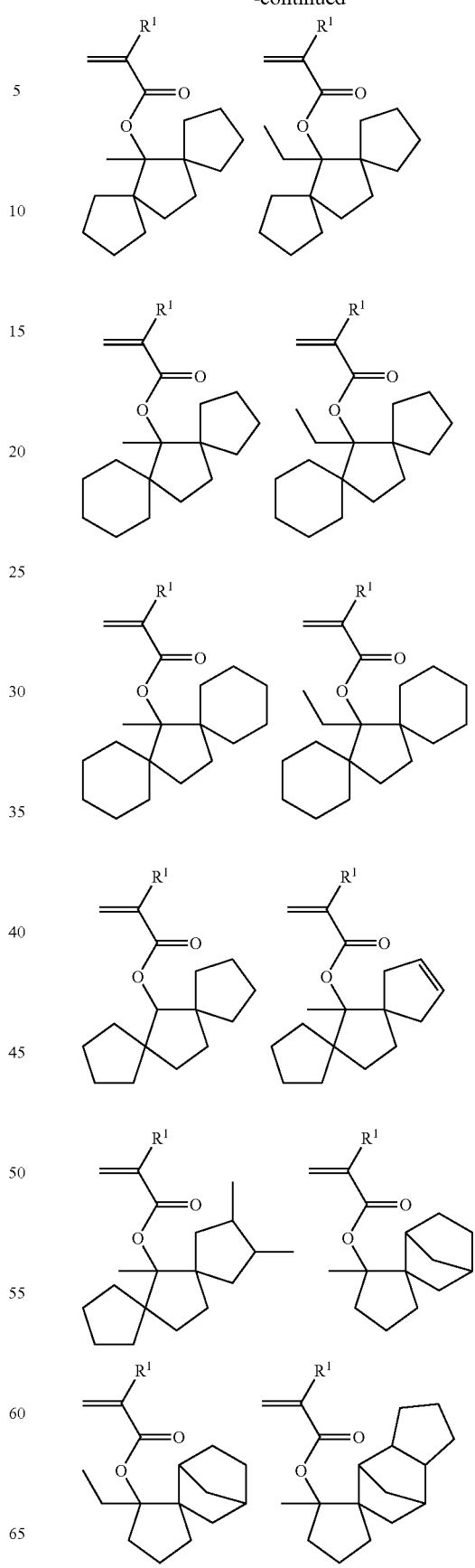

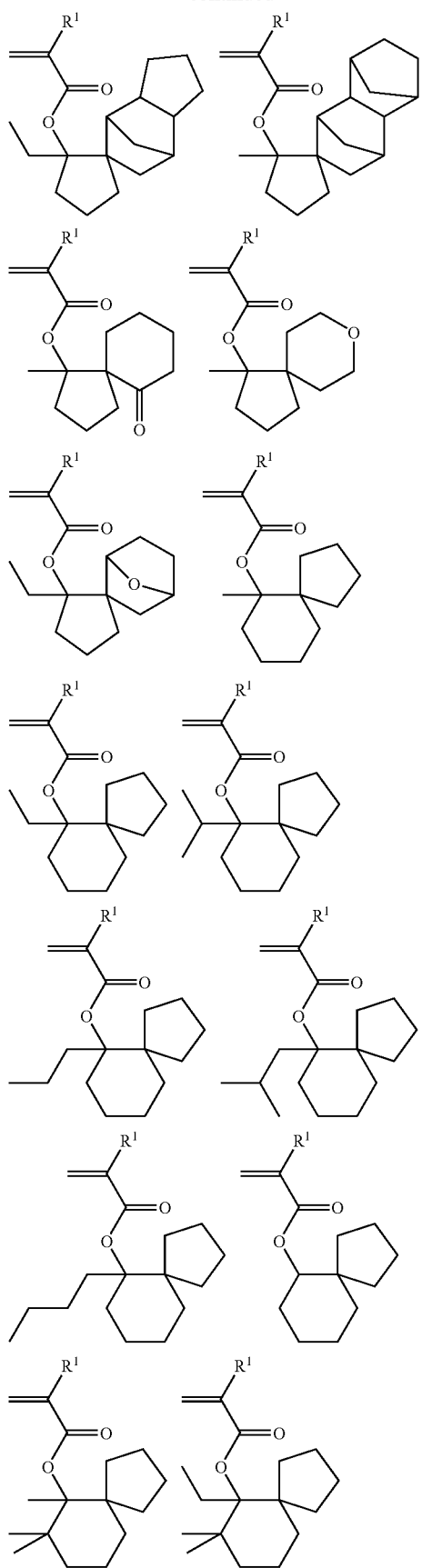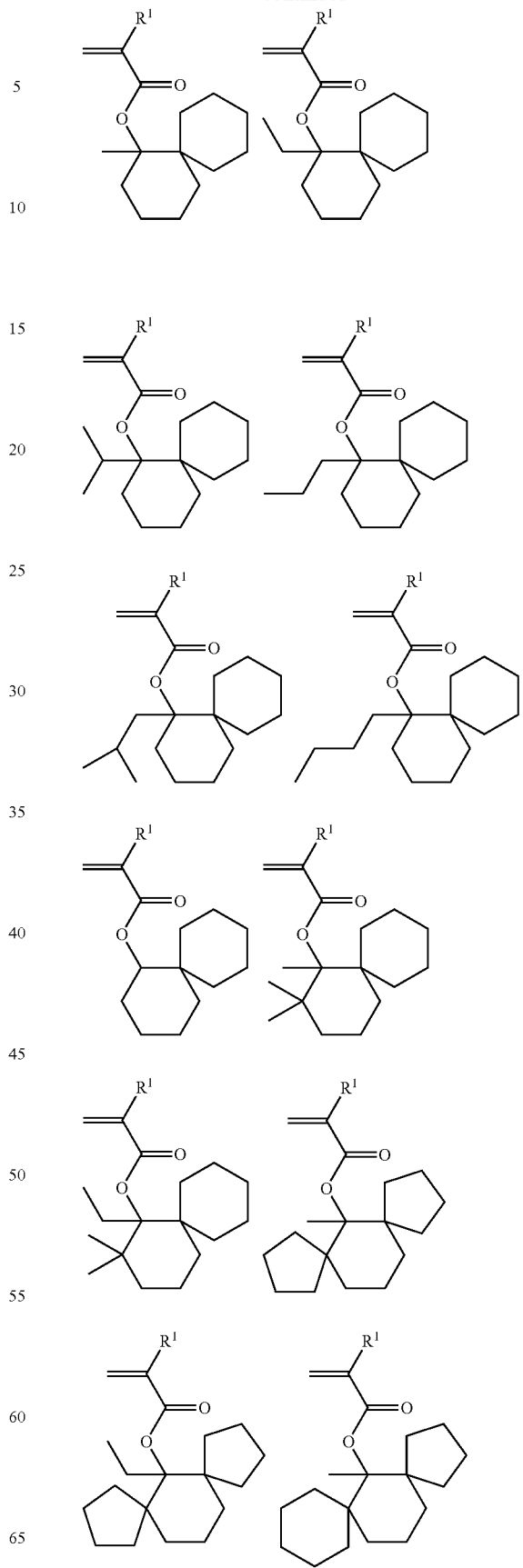

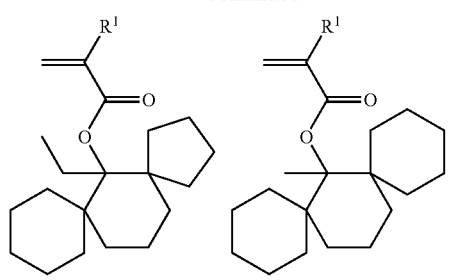
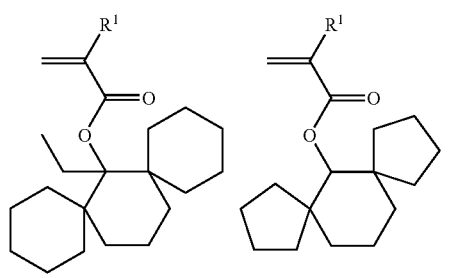
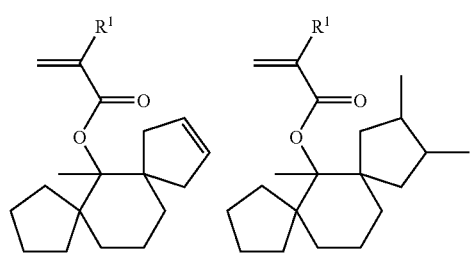
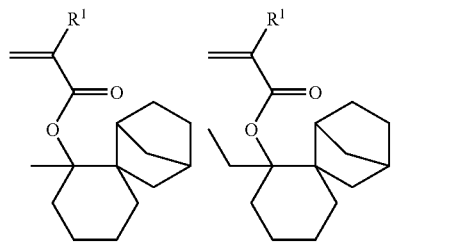
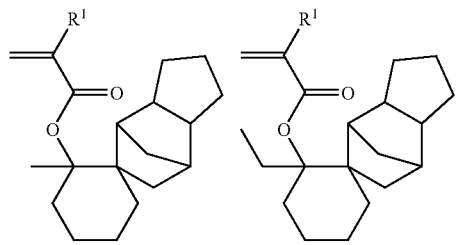
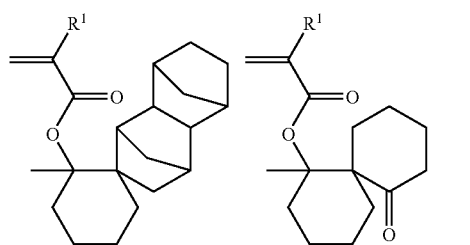
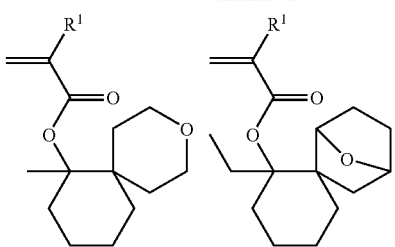
Herein R¹ is hydrogen, fluorine, methyl or trifluoromethyl.
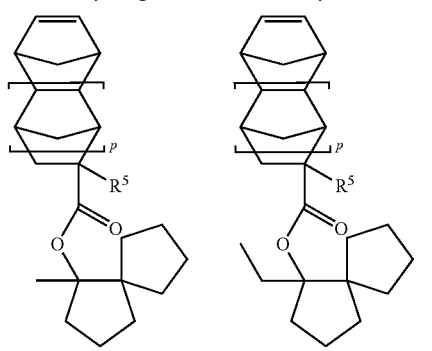
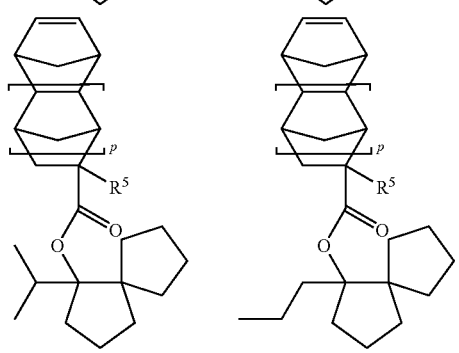
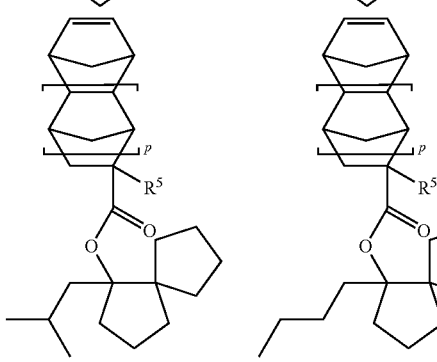
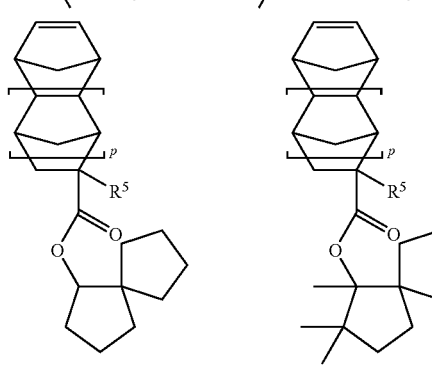

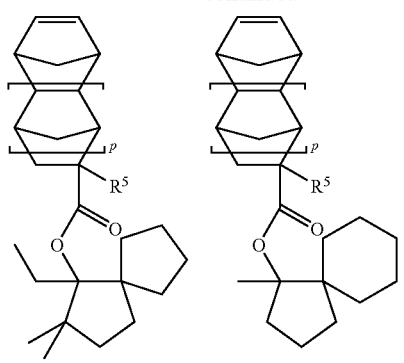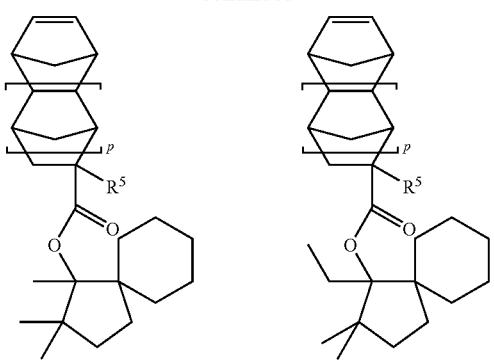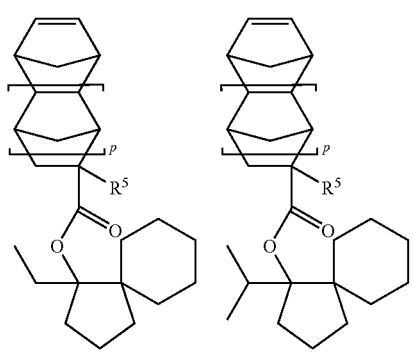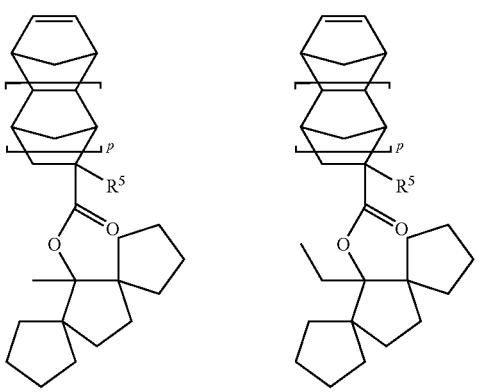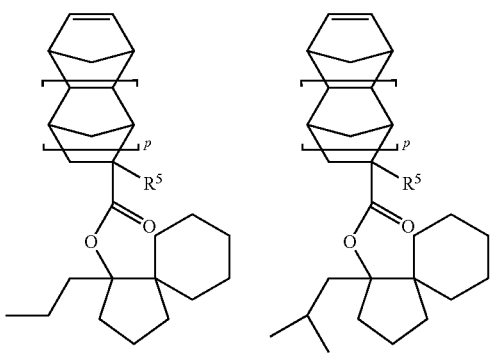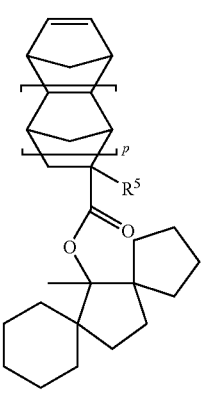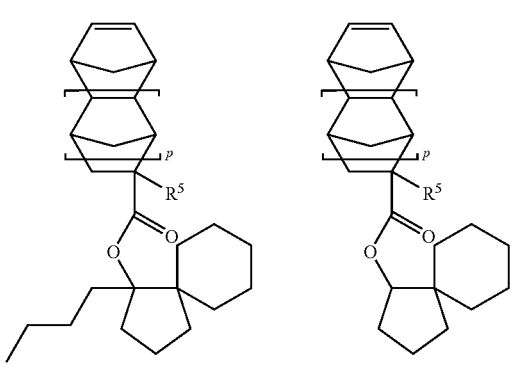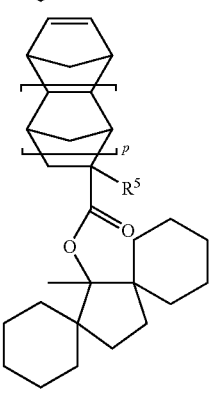

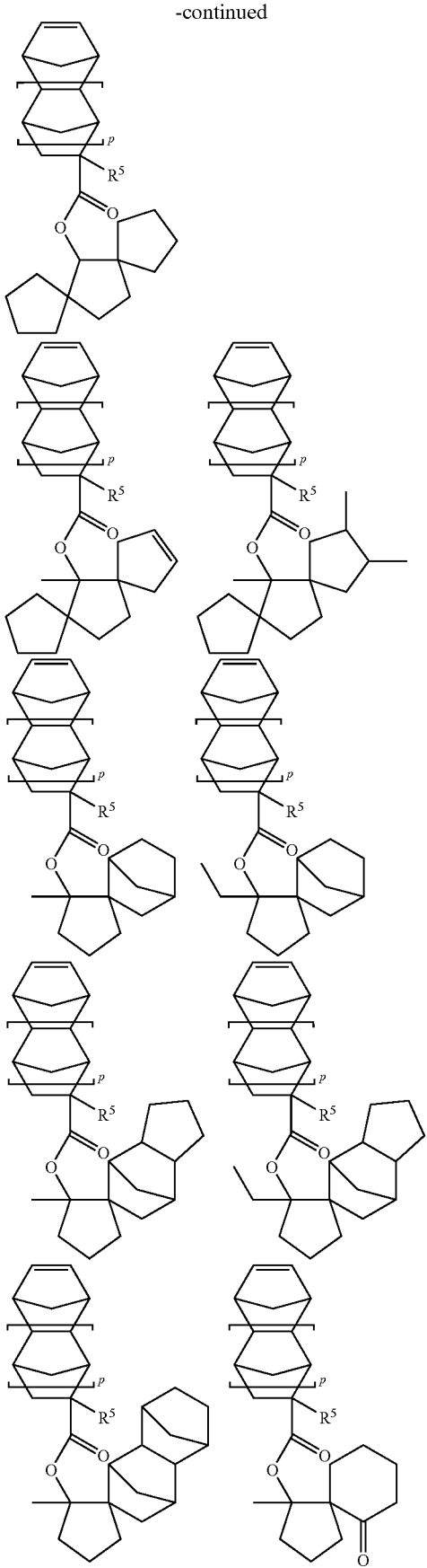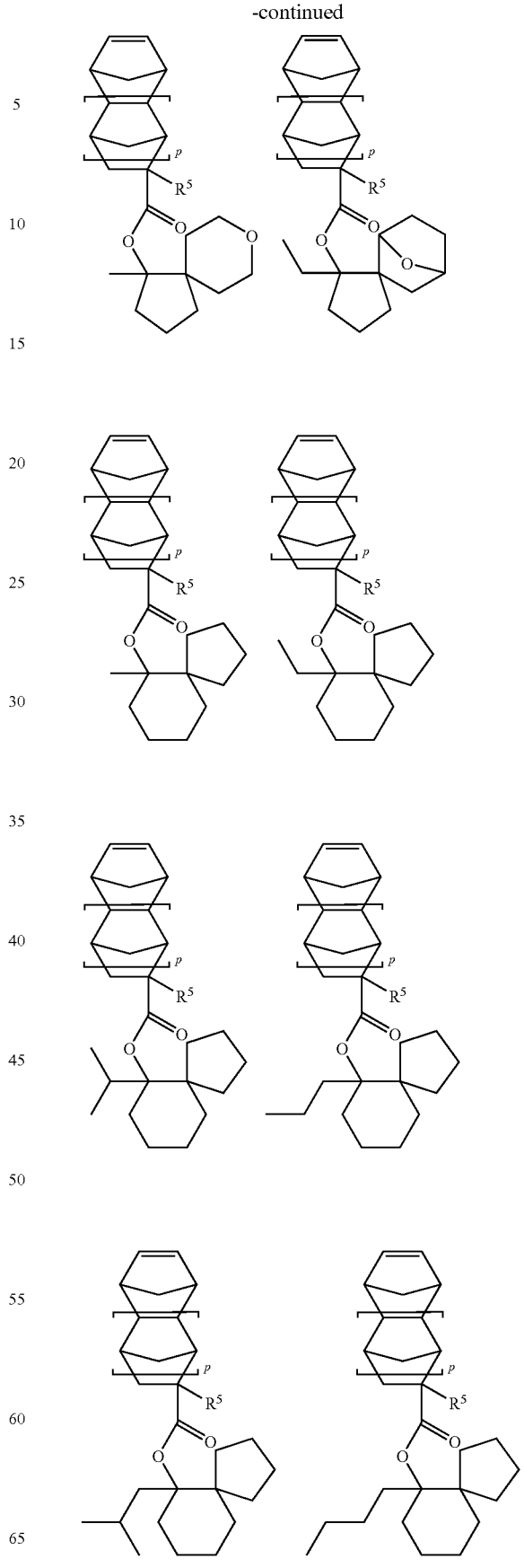

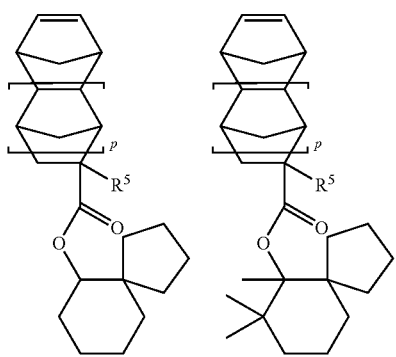
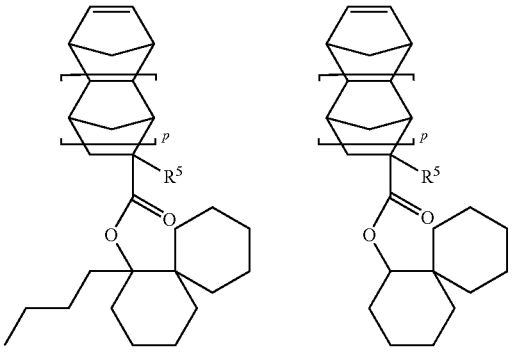
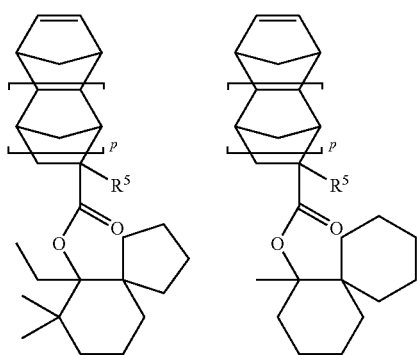
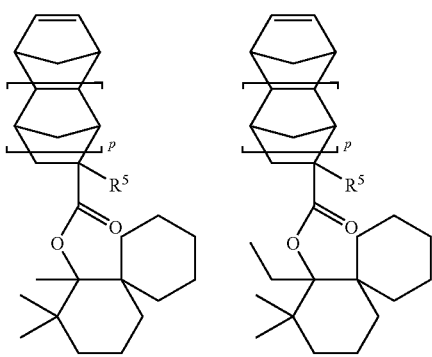
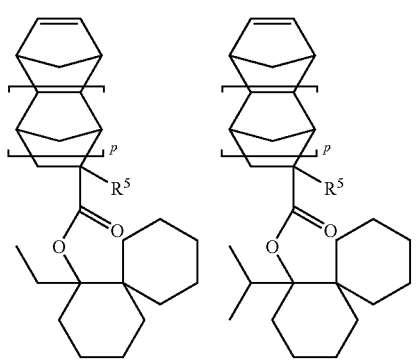
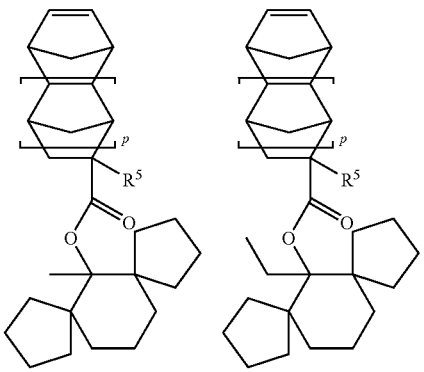
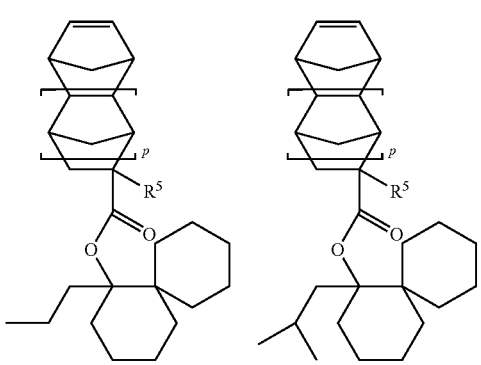
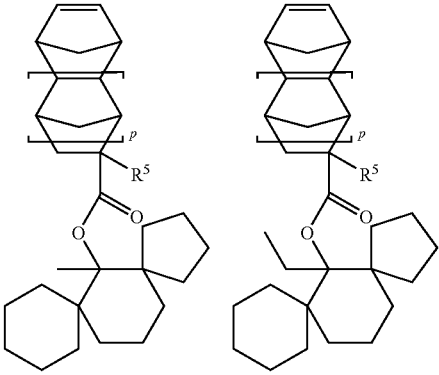

-continued

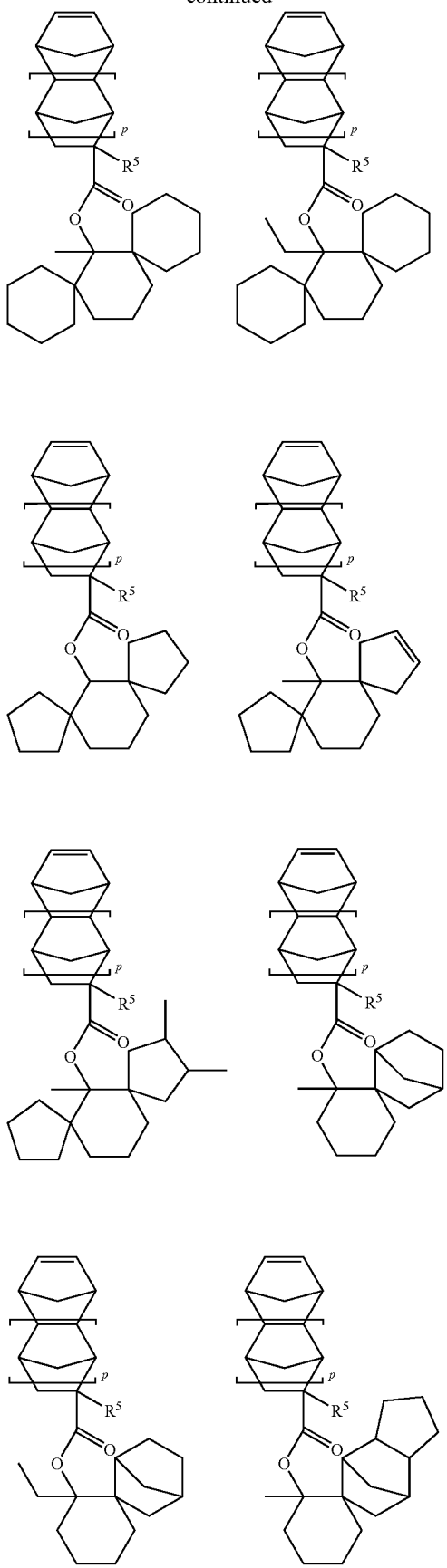

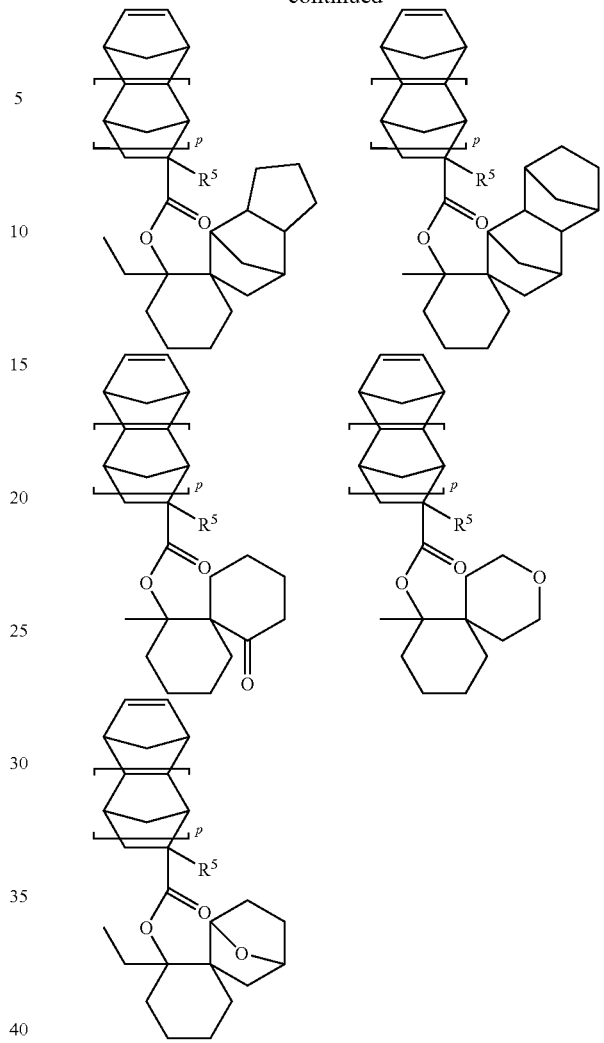

Herein $R^5$ is hydrogen or methyl, and p is 0 or 1.

Described below is the design concept of the acid-labile ester monomer having a spirocyclic structure represented by formula (1) according to the invention. The acid-labile ester monomer having a spirocyclic structure is a useful monomer from which recurring units of a polymer are derived, which polymer is used as a base resin in a radiation-sensitive resist composition to be described later. With respect to the acid-catalyzed elimination reaction within the resist film, the acid catalyzes elimination reaction of an acid labile ester to eliminate an olefin and to form a carboxylic acid, which incurs a change of solubility in developer to establish a dissolution contrast for the resist. JP-A H09-73173 discloses an acid labile group having a tertiary alkyl group of alkylcycloalkyl form and illustrates a spirocyclic structure as an example, but refers nowhere to its substitution site or form. The acid-labile ester monomer having a spirocyclic structure represented by formula (1), (2) or (3) according to the invention is designed to exert a high reactivity in acid-catalyzed elimination reaction by introducing a structural component necessary for the desired performance improvement into the spirocyclic structure at a specific site.

In the acid-catalyzed elimination reaction within the resist film, a carbocation forms on the carbon atom to which a polymerizable ester bonds, and elimination of proton from the carbocation forms an olefin. As the carbocation formed in this reaction is stabler, the activation energy of acid-catalyzed elimination reaction becomes lower, indicating a higher reactivity. The acid-labile ester monomer having a spirocyclic structure is characterized in that the carbon atom to which the polymerizable ester bonds is directly bonded to the quaternary carbon atom of spirocycle. The following three considerations account for a high reactivity.

1) An alkyl (such as cyclopentane, cyclohexane or norbornane ring) substitutes on a carbon atom adjoining the carbon atom to which the polymerizable ester bonds (referred to as "position-1 carbon atom"), that is, quaternary carbon atom to which X bonds (i.e., spiro carbon atom, referred to as "position-2 carbon atom"). The alkyl group exerts an electron donating effect, by which the cation on the position-1 carbon atom is stabilized. Also an alkyl group may substitute on the carbon atom which adjoins the position-1 carbon atom and to which $R^3$ and $R^4$ bond (referred to as "position-2' carbon atom"). In this case, further stabilization of the cation on the position-1 carbon atom is expected.

2) The alkyl substitution on the position-2 carbon atom (inclusive of position-2' carbon atom if any at position-2') provides a sterically hindered state around the position-1 carbon atom. Cation formation and subsequent olefin formation dissolve this steric hindrance, and the formed system becomes stabler in energy, allowing for easier progress of reaction. The magnitude of steric hindrance is demonstrated by a signal broadening in $^{13}$C-NMR being observed due to restrained equilibration between conformations at room temperature, as will be exemplified later in Examples.

3) In the carbocation intermediate formed on position-1 carbon atom, rearrangement reaction of alkyl group at position-2 (or position-2'), that is, 1,2-alkyl shift may occur so that a further stable carbocation may form. Equilibrium between the carbocations is believed to contribute to stabilization of cations, reducing the activation energy of reaction. This is embodied, in the case of 6-methylspiro[4.5]decyl ester compound, for example, by rearrangement of cation and resultant formation of plural olefins as shown in the following chemical reaction scheme.

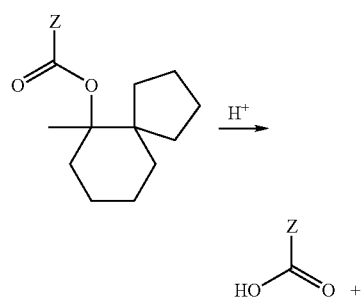

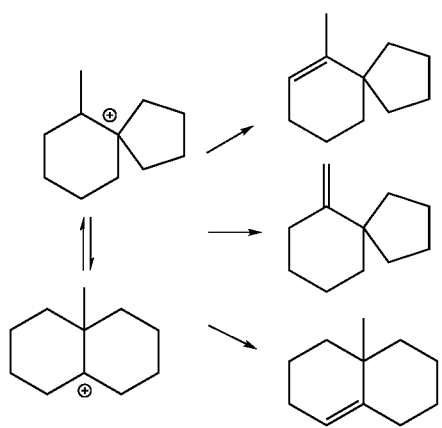

Of the acid-labile ester monomers of spirocyclic structure having formula (1), an appropriate structure may be selected for adjustment of elimination reactivity. For example, by a choice of the number of alicyclics to which the polymerizable ester bonds (whether n is 1 or 2) and the type of substituent $R^2$ bonded to position-1 carbon atom (whether it is hydrogen or a monovalent hydrocarbon group, or the type of monovalent hydrocarbon group in the latter case), the elimination reactivity in the resist film may be adjusted as appropriate. Also by a choice of the structure of alicyclic moiety bonding to position-2 spiro-carbon atom and the type of $R^3$ and $R^4$, the acid diffusion distance within the resist film may be adjusted as appropriate.

Now the method for preparing the acid-labile ester monomers of spirocyclic structure having formula (1), (2) or (3) is described.

In one typical non-limiting example, the acid-labile ester monomers of spirocyclic structure having formula (1), (2) or (3) may be synthesized by acylation reaction of a corresponding alcohol compound, which may, in turn, be synthesized by alkylation of a ketone compound (or reduction where $R^2$ is hydrogen).

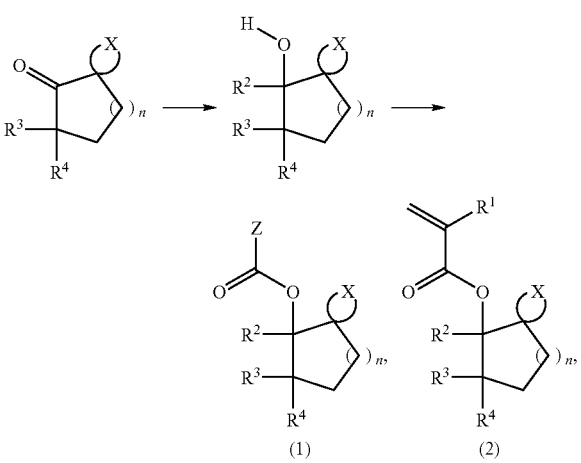

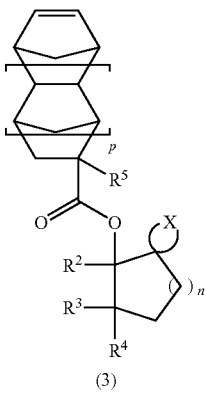

(3)

Herein Z is a monovalent group having a polymerizable double bond. X is a divalent group which forms a substituted or unsubstituted cyclopentane, cyclohexane or norbornane ring with the carbon atom to which it is attached. $R^1$ is hydrogen, fluorine, methyl or trifluoromethyl. $R^2$ is hydrogen or a straight, branched or cyclic $C_1$-$C_{10}$ monovalent hydrocarbon group. $R^3$ and $R^4$ are each independently hydrogen or a straight, branched or cyclic $C_1$-$C_{10}$ monovalent hydrocarbon group, or $R^3$ and $R^4$, taken together, stand for a divalent group which forms a substituted or unsubstituted cyclopentane or cyclohexane ring with the carbon atom to which they are attached. $R^5$ is hydrogen or methyl. The subscript n is 1 or 2, and p is 0 or 1.

For the esterification reaction, any well-known procedures for ester production including reaction with acylating agents, reaction with carboxylic acid, and ester exchange reaction may be applied. As for the reaction with acylating agents, a starting alcohol compound, an acylating agent, and a base are successively or simultaneously added to a solvent whereupon reaction takes place. Exemplary solvents include chlorine-based solvents such as methylene chloride, chloroform and trichloroethylene, hydrocarbons such as hexane, heptane, benzene, toluene, xylene and cumene, ethers such as dibutyl ether, diethylene glycol diethyl ether, diethylene glycol dimethyl ether, tetrahydrofuran, and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide and hexamethylphosphoric triamide, and mixtures comprising two or more thereof. Exemplary acylating agents include acid halides such as acrylic chloride, methacrylic chloride, acrylic bromide, methacrylic bromide, α-trifluoromethylacrylic chloride, bicyclo[2.2.1]hept-5-ene-2-carboxylic chloride, bicyclo[2.2.1]hept-5-ene-2-methyl-2-carboxylic chloride, tetracyclo[4.4.0.1$^{2,5}$.1$^{7,10}$]dodec-8-ene-3-carboxylic chloride, and tetracyclo[4.4.0.1$^{2,5}$.1$^{7,10}$]dodec-8-ene-3-methyl-3-carboxylic chloride; and acid anhydrides such as acrylic anhydride, methacrylic anhydride, α-trifluoromethylacrylic anhydride, bicyclo[2.2.1]hept-5-ene-2-carboxylic anhydride, bicyclo[2.2.1]hept-5-ene-2-methyl-2-carboxylic anhydride, tetracyclo[4.4.0.1$^{2,5}$.1$^{7,10}$]dodec-8-ene-3-carboxylic anhydride, tetracyclo[4.4.0.1$^{2,5}$.1$^{7,10}$]dodec-8-ene-3-methyl-3-carboxylic anhydride,
mixed acrylic/trifluoroacetic anhydride,
mixed methacrylic/trifluoroacetic anhydride,
mixed α-trifluoromethylacrylic/trifluoroacetic anhydride,
mixed bicyclo[2.2.1]hept-5-ene-2-carboxylic/trifluoroacetic anhydride,
mixed bicyclo[2.2.1]hept-5-ene-2-methyl-2-carboxylic/trifluoroacetic anhydride,
mixed tetracyclo[4.4.0.1$^{2,5}$.1$^{7,10}$]dodec-8-ene-3-carboxylic/trifluoroacetic anhydride,
mixed tetracyclo[4.4.0.1$^{2,5}$.1$^{7,10}$]dodec-8-ene-3-methyl-3-carboxylic/trifluoroacetic anhydride,
mixed acrylic/pivalic anhydride,
mixed methacrylic/pivalic anhydride,
mixed α-trifluoromethylacrylic/pivalic anhydride,
mixed bicyclo[2.2.1]hept-5-ene-2-carboxylic/pivalic anhydride,
mixed bicyclo[2.2.1]hept-5-ene-2-methyl-2-carboxylic/pivalic anhydride,
mixed tetracyclo[4.4.0.1$^{2,5}$.1$^{7,10}$]dodec-8-ene-3-carboxylic/pivalic anhydride,
mixed tetracyclo[4.4.0.1$^{2,5}$.1$^{7,10}$]dodec-8-ene-3-methyl-3-carboxylic/pivalic anhydride,
mixed acrylic/p-nitrobenzoic anhydride,
mixed methacrylic/p-nitrobenzoic anhydride,
mixed ethyl acrylate/carbonic anhydride,
mixed ethyl methacrylate/carbonic anhydride,
acrylic acid/p-nitrophenyl, methacrylic acid/p-nitrophenyl, α-trifluoromethylacrylic acid/p-nitrophenyl,
mixed acrylic/p-toluenesulfonic anhydride,
mixed methacrylic/p-toluenesulfonic anhydride,
mixed α-trifluoromethylacrylic/p-toluenesulfonic anhydride,
mixed bicyclo[2.2.1]hept-5-ene-2-carboxylic/p-toluenesulfonic anhydride,
mixed bicyclo[2.2.1]hept-5-ene-2-methyl-2-carboxylic/p-toluenesulfonic anhydride,
mixed tetracyclo[4.4.0.1$^{2,5}$.1$^{7,10}$]dodec-8-ene-3-carboxylic/p-toluenesulfonic anhydride, and
mixed tetracyclo[4.4.0.1$^{2,5}$.1$^{7,10}$]dodec-8-ene-3-methyl-3-carboxylic/p-toluenesulfonic anhydride. Exemplary bases include triethylamine, diisopropylethylamine, N,N-dimethylaniline, pyridine, and 4-dimethylaminopyridine. When acid anhydrides are used as the acylating agent, the reaction may be carried out in the presence of an acid catalyst instead of the base, the acid catalyst being selected from mineral acids such as hydrochloric acid, hydrobromic acid, sulfuric acid and nitric acid and organic acids such as oxalic acid, trifluoroacetic acid, methanesulfonic acid, benzenesulfonic acid, and p-toluenesulfonic acid. For the acylation reaction, an appropriate reaction temperature may be selected in accordance with the type of acylating agent and reaction conditions. The reaction temperature generally ranges from −50° C. to around the boiling point of the solvent, and preferably from −20° C. to room temperature. The amount of acylating agent used varies depending on its structure and is usually 1 to 40 moles, and preferably 1 to 5 moles per mole of the starting alcohol compound.

The reaction with carboxylic acid is dehydration reaction between a corresponding carboxylic acid (i.e., acrylic acid, methacrylic acid, α-trifluoromethylacrylic acid, bicyclo[2.2.1]hept-5-ene-2-carboxylic acid, bicyclo[2.2.1]hept-5-ene-2-methyl-2-carboxylic acid, tetracyclo[4.4.0.1$^{2,5}$.1$^{7,10}$]dodec-8-ene-3-carboxylic acid, or tetracyclo[4.4.0.1$^{2,5}$.1$^{7,10}$]dodec-8-ene-3-methyl-3-carboxylic acid) and the starting alcohol compound, which is generally carried out in the presence of an acid catalyst. The amount of carboxylic acid used varies depending on its structure and is usually 1 to 40 moles, and preferably 1 to 5 moles per mole of the starting alcohol compound. Suitable acid catalysts include mineral acids such as hydrochloric acid, hydrobromic acid, sulfuric acid and nitric acid and organic acids such as oxalic acid, trifluoroacetic acid, methanesulfonic acid, benzenesulfonic acid, and p-toluenesulfonic acid, which may be used alone or in admixture. The acid catalyst may be used in an amount of 0.001 to 1 mole, and preferably 0.01 to 0.05 mole per mole of the starting alcohol compound. The solvent may be the same as exemplified for the reaction with esterifying agents. Often, the reaction temperature preferably ranges from −50° C. to around the boiling point of the solvent. It is acceptable to carry out the reaction in a solvent containing a hydrocarbon such as hexane, heptane, benzene, toluene, xylene or cumene while azeotroping off the water generated during the reaction. In this embodiment, water may be distilled off while refluxing at the boiling point of the solvent under atmospheric pressure. Water may also be distilled off at a temperature below the boiling point under reduced pressure.

As for the ester exchange reaction, an ester of a corresponding carboxylic acid (i.e., acrylate, methacrylate, α-trifluoromethylacrylate, bicyclo[2.2.1]hept-5-ene-2-carboxylate, bicyclo[2.2.1]hept-5-ene-2-methyl-2-carboxylate, tetracyclo[4.4.0.1$^{2,5}$.1$^{7,10}$]dodec-8-ene-3-carboxylate, or tetracyclo[4.4.0.1$^{2,5}$.1$^{7,10}$]dodec-8-ene-3-methyl-3-carboxylate) and the starting alcohol compound are reacted in the presence of a catalyst while the alcohol generated during the reaction is removed from the system. The carboxylates used herein are preferably primary alkyl esters, of which methyl, ethyl and n-propyl esters are preferred for cost and fast progress of reaction. The amount of carboxylate used varies depending on its structure and is usually 1 to 40 moles, and preferably 1 to 5 moles per mole of the starting alcohol compound. Suitable catalysts include mineral acids such as hydrochloric acid, hydrobromic acid, sulfuric acid and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide, which may be used alone or in admixture. The catalyst may be used in an amount of 0.001 to 20 moles, and preferably 0.01 to 0.05 mole per mole of the starting alcohol compound. The reaction may be carried out in a solventless system (one reactant, carboxylate itself may serve as the solvent), which is preferred because extra steps such as concentration and solvent recovery are unnecessary. In certain cases, however, a solvent may be used in an auxiliary manner for the purposes of preventing the end compound or reactants from polymerization. The solvent used herein is preferably selected from hydrocarbons such as hexane, heptane, benzene, toluene, xylene and cumene, and ethers such as dibutyl ether, diethylene glycol diethyl ether, diethylene glycol dimethyl ether, tetrahydrofuran and 1,4-dioxane, alone or in admixture. An appropriate reaction temperature may be selected in accordance with the type of carboxylate used and reaction conditions. The reaction is often carried out at an elevated temperature, typically near the boiling point of a low-boiling alcohol resulting from ester exchange reaction, such as methanol, ethanol or 1-propanol while distilling off the alcohol being generated. The alcohol may be distilled off at a temperature below the boiling point under reduced pressure.

The reactant to be acylated, alcohol compound may be synthesized by addition reaction of an organometallic reagent to a corresponding ketone compound or reduction reaction of a corresponding ketone compound. Suitable organometallic reagents used in addition reaction include organolithium reagents, organosodium reagents, organopotassium reagents, organomagnesium reagents (e.g., Grignard reagents), organozinc reagents, organotin reagents, organoboron reagents, and organosilicon reagents. Of these, organolithium reagents and Grignard reagents are most preferred. The reaction may be effected in a solvent, for example, ethers such as dibutyl ether, diethylene glycol diethyl ether, diethylene glycol dimethyl ether, tetrahydrofuran and 1,4-dioxane, and hydrocarbons such as hexane, heptane, benzene, toluene, xylene and cumene. Suitable reducing reagents used in the reduction reaction include metal hydrides such as sodium hydride, potassium hydride, calcium hydride, aluminum hydride, borane, and diisobutyl aluminum hydride, metal hydrogen complexes such as sodium borohydride and lithium aluminum hydride, and alkyl and alkoxy derivatives thereof. The reduction reaction may also be effected in a solvent, examples of which include those exemplified for the addition reaction with organometallic reagents, and water, and alcohols such as methanol, ethanol, and isopropyl alcohol, alone or in admixture of two or more.

The monomer and any synthesis intermediate thereof may be purified prior to use by any standard techniques including distillation, crystallization, recrystallization, and chromatography.

Polymer

The polymer of the invention is characterized by comprising recurring units having the general formula (1a), (2a) or (3a), which are derived from the acid-labile ester monomer having a spirocyclic structure.

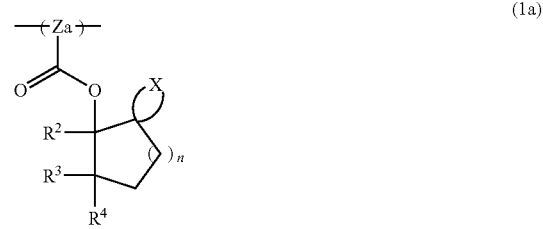

(1a)

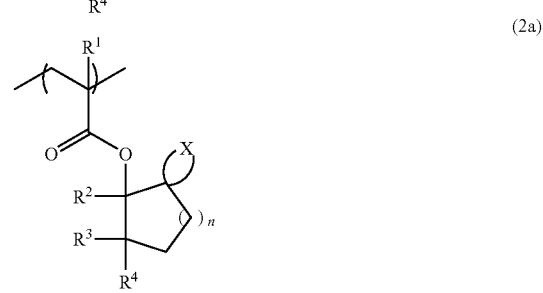

(2a)

-continued (3a)

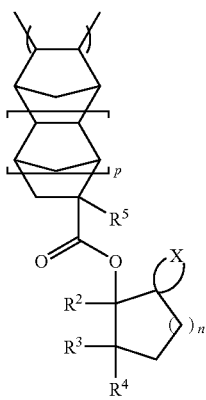

Herein Za is a trivalent group derived by polymerization from a monovalent group Z having a polymerizable double bond. X is a divalent group which forms a substituted or unsubstituted cyclopentane, cyclohexane or norbornane ring with the carbon atom to which it is attached. $R^1$ is hydrogen, fluorine, methyl or trifluoromethyl. $R^2$ is hydrogen or a straight, branched or cyclic $C_1$-$C_{10}$ monovalent hydrocarbon group. $R^3$ and $R^4$ are each independently hydrogen or a straight, branched or cyclic $C_1$-$C_{10}$ monovalent hydrocarbon group, or $R^3$ and $R^4$, taken together, stand for a divalent group which forms a substituted or unsubstituted cyclopentane or cyclohexane ring with the carbon atom to which they are attached. $R^5$ is hydrogen or methyl. The subscript n is 1 or 2, and p is 0 or 1. Examples of X, $R^2$, $R^3$ and $R^4$ are as described above.

In addition to the above recurring units, the inventive polymer may further comprise recurring units of at least one type selected from the following general formulae (5a) to (8a).

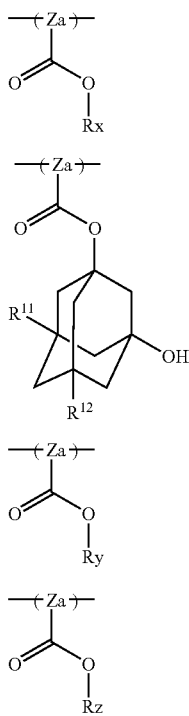

Herein Za is as defined above, $R^{11}$ and $R^{12}$ are each independently hydrogen or hydroxyl, Rx denotes an acid labile group, Ry denotes a substituent group having lactone structure, and Rz denotes hydrogen, a $C_1$-$C_{15}$ fluoroalkyl group or a $C_1$-$C_{15}$ fluoroalcohol-containing substituent group.

Za is a trivalent group derived from a monovalent group Z having a polymerizable double bond while Z is as defined and exemplified above. Preferably Z is vinyl, isopropenyl, 3,3,3-trifluoro-2-propenyl, 5-norbornen-2-yl, or tetracyclo[4.4.0.1$^{2,5}$.1$^{7,10}$]dodec-8-en-3-yl. Accordingly, examples of the formula:

are those of the following formulae:

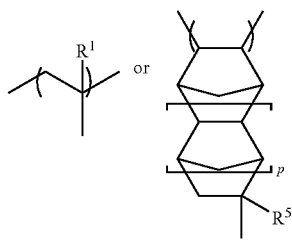

wherein $R^1$, $R^5$ and p are as defined above.

A polymer comprising recurring units of formula (5a) is decomposable under the action of an acid to generate a carboxylic acid so that the polymer may become alkali soluble. The acid labile groups represented by Rx may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

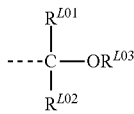  (L1)

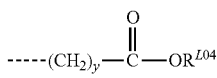  (L2)

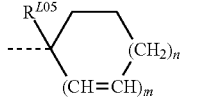  (L3)

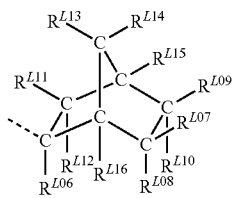  (L4)

The broken line denotes a valence bond. In formula (L1), $R^{L01}$ and $R^{L02}$ are hydrogen or straight, branched or cyclic alkyl groups of 1 to 18 carbon atoms, preferably 1 to 10 carbon atoms, examples of which include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of these groups in which some hydrogen atoms are replaced by hydroxyl, alkoxy, oxo, amino, alkylamino or the like. Examples of suitable substituted alkyl groups are shown below.

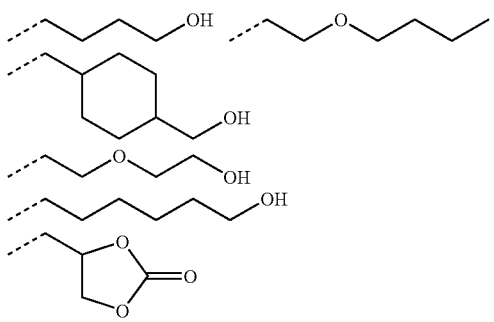

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl, and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary optionally substituted aryl groups are phenyl, methylphenyl, naphthyl, anthryl, phenanthryl, and pyrenyl. In formula (L3), m is 0 or 1, n is 0, 1, 2 or 3, and 2m+n is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. Examples of these groups are the same as exemplified for $R^{L05}$. $R^{L07}$ to $R^{L16}$ independently denote hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair). Each participant of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

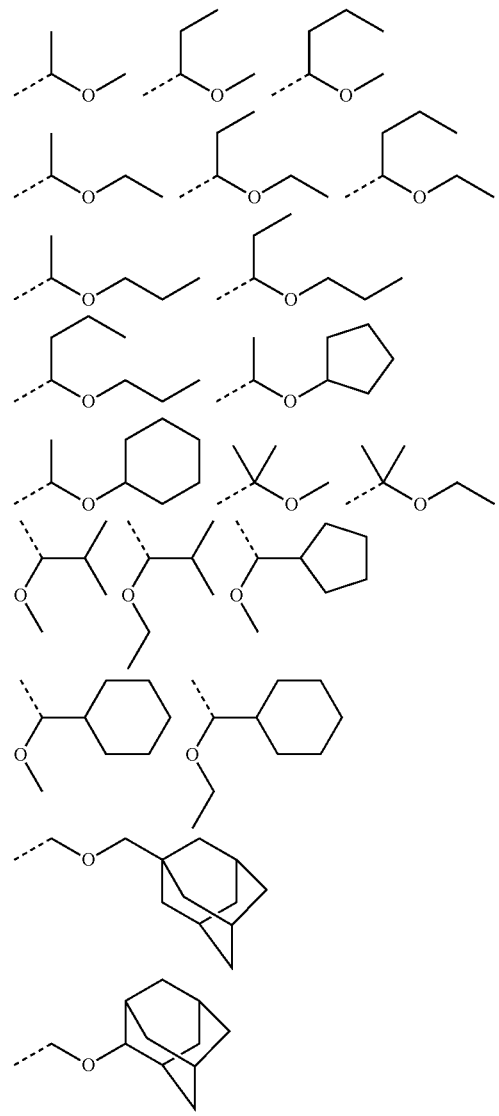

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

The acid labile group of formula (L4) is preferably selected from groups of the following formulae (L4-1) to (L4-4).

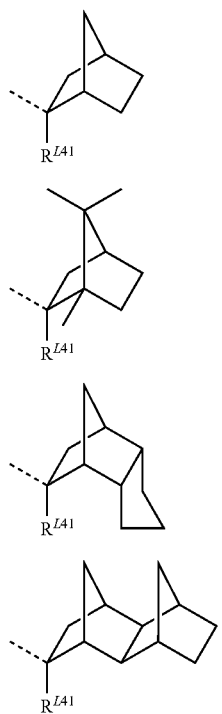

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

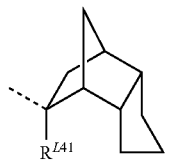

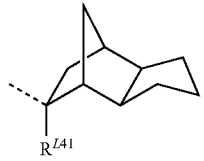

$R^{L41}$ is as defined above.

Similarly, the general formula (L4-4) represents one or a mixture of two or more selected from groups having the following general formulas (L4-4-1) to (L4-4-4).

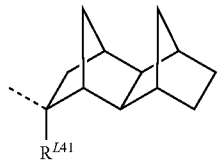

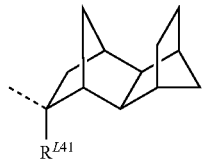

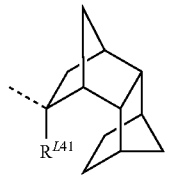

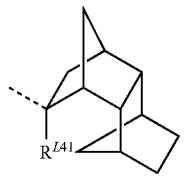

$R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid-catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

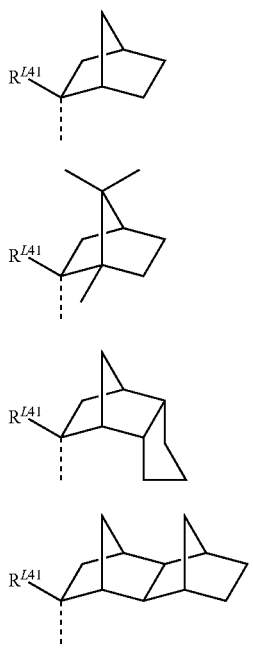

(L4-1-endo)

(L4-2-endo)

(L4-3-endo)

(L4-4-endo)

$R^{L41}$ is as defined above.

Illustrative examples of the acid labile group of formula (L4) are given below, but not limited thereto.

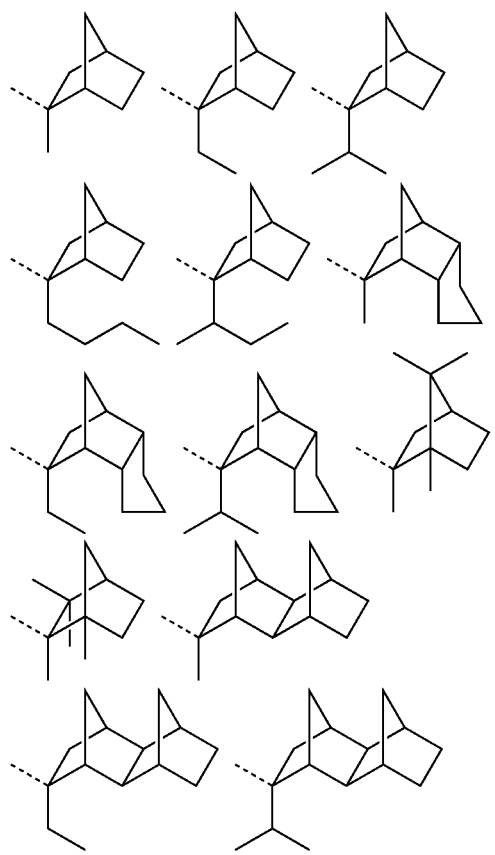

Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.

Illustrative, non-limiting examples of partial structure O-Rx in the recurring units of formula (5a) are given below.

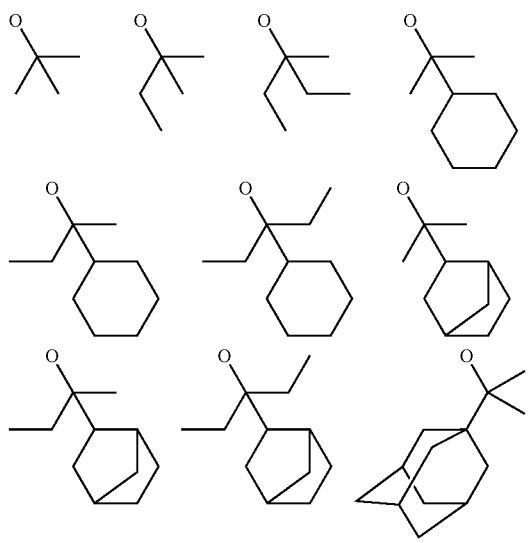

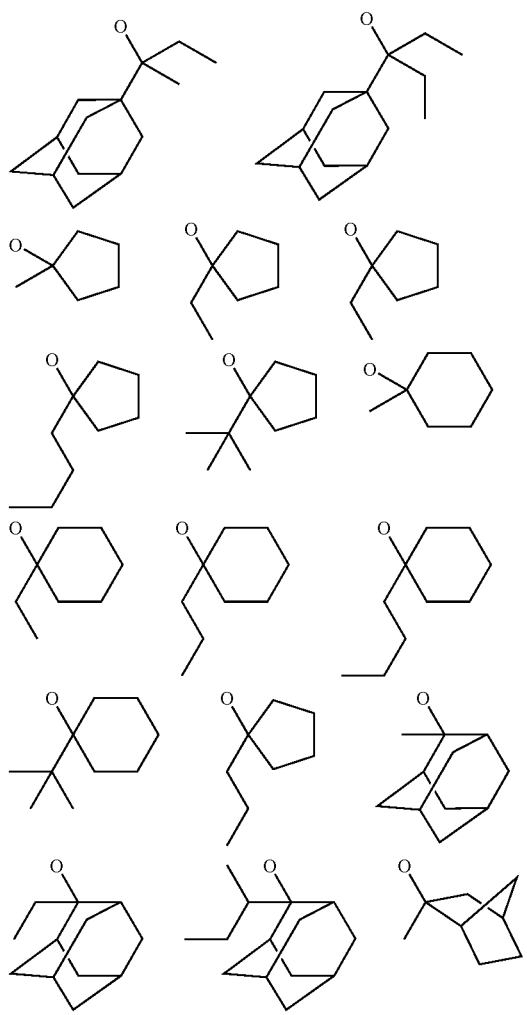

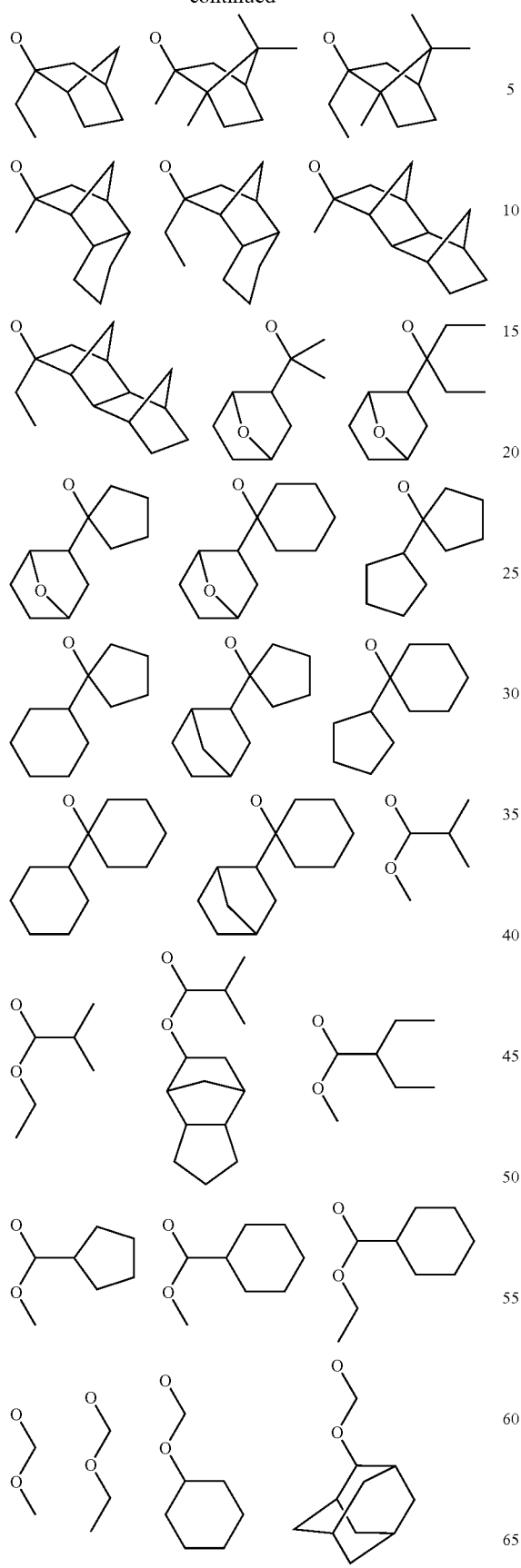
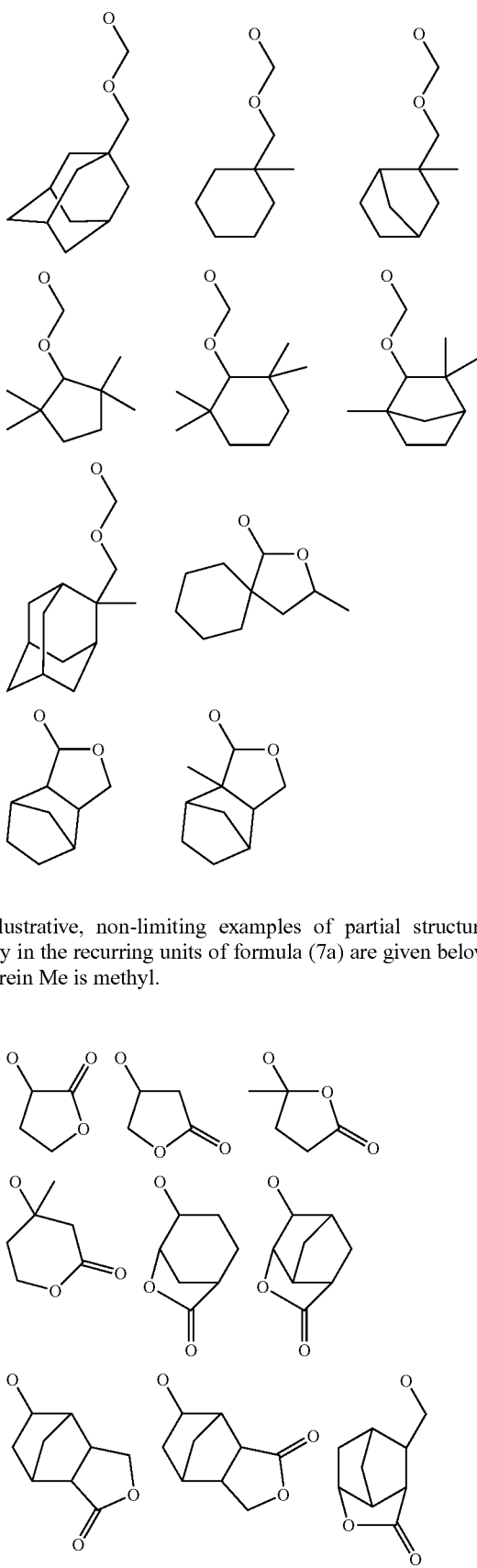
Illustrative, non-limiting examples of partial structure O-Ry in the recurring units of formula (7a) are given below wherein Me is methyl.
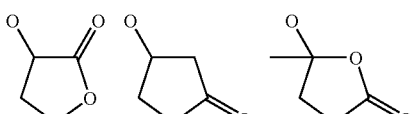
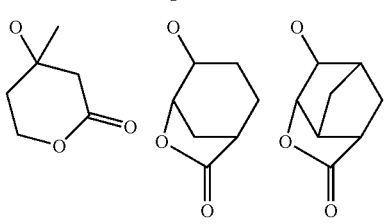
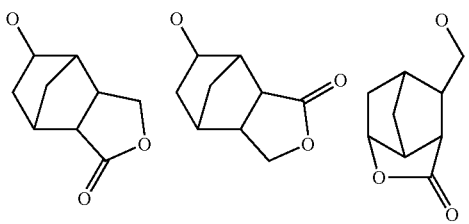

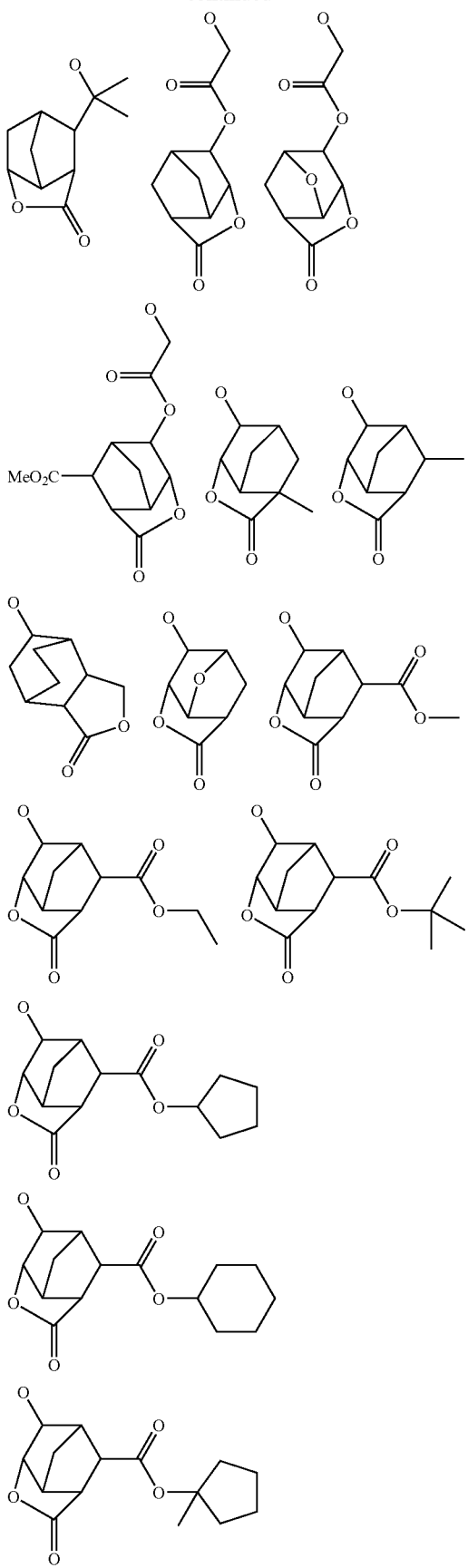
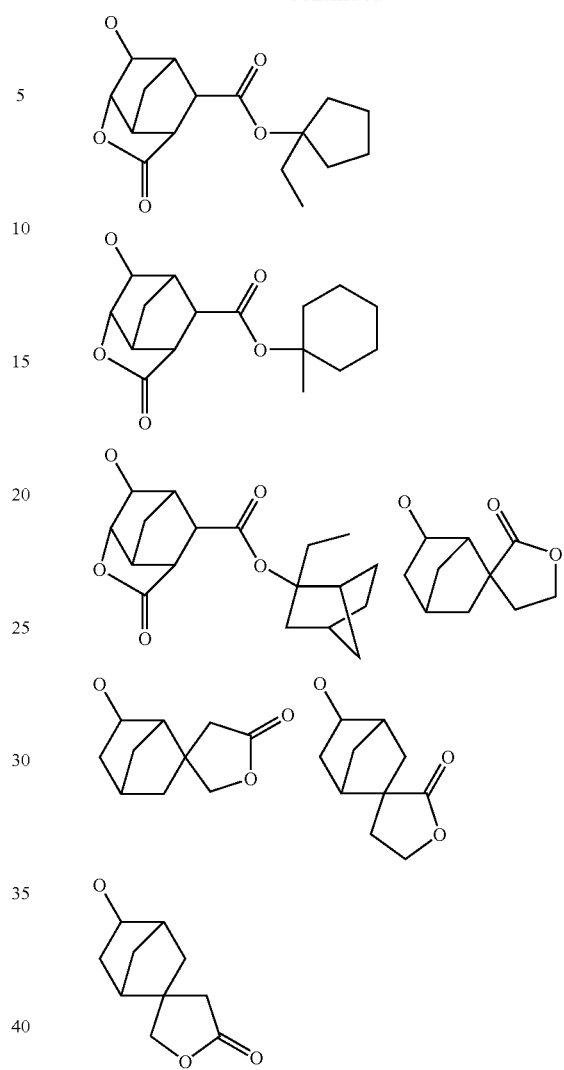
Illustrative, non-limiting examples of partial structure O—Rz in the recurring units of formula (8a) are given below.
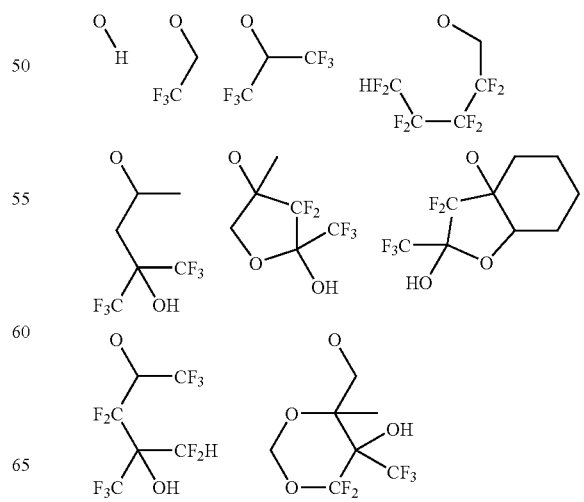

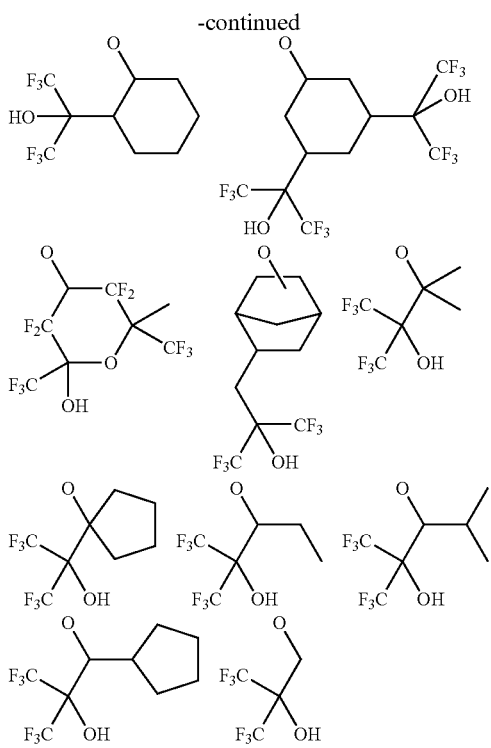

The polymer of the invention may further comprise recurring units derived from another monomer having a carbon-to-carbon double bond other than the foregoing. Examples of the additional monomer include substituted acrylic acid esters such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, imides, and other monomers.

The polymers have a weight average molecular weight (Mw) of 1,000 to 500,000, and preferably 3,000 to 100,000, as measured by GPC versus polystyrene standards. Outside the range, a polymer may suffer an extreme drop of etching resistance or a reduced resolution due to a failure to provide a difference in dissolution rate before and after exposure.

In the inventive polymer, the preferred proportion of respective recurring units derived from discrete monomers may fall, for example, in the range (mol %) shown below, but is not limited thereto. The polymer may consist essentially of:

(I) from more than 0 mol % to 100 mol %, preferably 2 to 70 mol %, and more preferably 5 to 50 mol % of constituent units having formula (1a) derived from monomer having formula (1) (or formula (2a) or (3a) derived from monomer having formula (2) or (3));

(II) from 0 mol % to less than 100 mol %, preferably 1 to 95 mol %, and more preferably 20 to 80 mol % of constituent units of one or more type having formulae (5a) to (8a); and optionally, (III) from 0 mol % to 80 mol %, preferably 0 to 70 mol %, and more preferably 0 to 50 mol % of constituent units of one or more type derived from the additional monomer(s).

Preferably, the polymer contains 1 to 95 mol %, especially 20 to 80 mol % of recurring units having formulae (1a) (alternatively (2a) or (3a)) and (5a) combined; 0 to 95 mol %, especially 0 to 50 mol % of recurring units having formula (6a); 0 to 95 mol %, especially 20 to 80 mol % of recurring units having formula (7a); and 0 to 95 mol %, especially 0 to 50 mol % of recurring units having formula (8a).

The polymer of the invention may be prepared through copolymerization reaction using the compound having formula (1), (2) or (3) as a first monomer and one or more compounds having a polymerizable double bond as second and subsequent monomers. Each of the compound having formula (1), (2) or (3) as a first monomer and second and subsequent monomers which are used in the copolymerization process may contain oligomeric and polymeric fractions which are preferably present in an amount of up to 10 mol %, more preferably up to 3 mol %, and even more preferably up to 1 mol % based on the monomer reactant.

Various modes of copolymerization reaction may be used for the preparation of the inventive polymer. The preferred modes are radical polymerization, anionic polymerization and coordination polymerization.

For radical polymerization, preferred reaction conditions include (a) a solvent selected from hydrocarbons such as benzene, ethers such as tetrahydrofuran, alcohols such as ethanol, and ketones such as methyl isobutyl ketone; (b) a polymerization initiator selected from azo compounds such as 2,2'-azobisisobutyronitrile, and peroxides such as benzoyl peroxide and lauroyl peroxide; (c) a reaction temperature in the range of about 0° C. to about 100° C.; and (d) a reaction time in the range of about 0.5 to about 48 hours. Reaction parameters outside these ranges need not be excluded.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 hour to about 48 hours, and (e) a stopper selected from among proton-donative compounds such as methanol, halides such as methyl iodide, and electrophilic compounds. Reaction parameters outside these ranges need not be excluded.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction parameters outside these ranges need not be excluded.

Resist Composition

The polymer of the invention is advantageously used as a base resin in a resist composition, and specifically a chemically amplified positive resist composition. Thus the invention provides a resist composition comprising the polymer, and especially a chemically amplified positive resist composition comprising the polymer. The resist composition preferably comprises:

(A) a base resin comprising the inventive polymer,
(B) an acid generator,
(C) an organic solvent, and optionally,
(D) an organic nitrogen-containing compound, and
(E) a surfactant.

For the resist composition, the base resin as component (A) may comprise another resin having a dissolution rate in an alkaline developer that increases under the action of an acid, if desired, as well as the inventive polymer. Exemplary other resins include, but are not limited to, (i) poly(meth)acrylic acid derivatives, (ii) norbornene derivative/maleic anhydride copolymers, (iii) hydrogenated products of ring-opening metathesis polymers (ROMP), and (iv) vinyl ether/maleic anhydride/(meth)acrylic acid derivative copolymers.

The hydrogenated products of ROMP (iii) are synthesized by the method illustrated in Examples of JP-A 2003-66612. Illustrative examples of such hydrogenated polymers include those polymers having the recurring units shown below, but are not limited thereto.

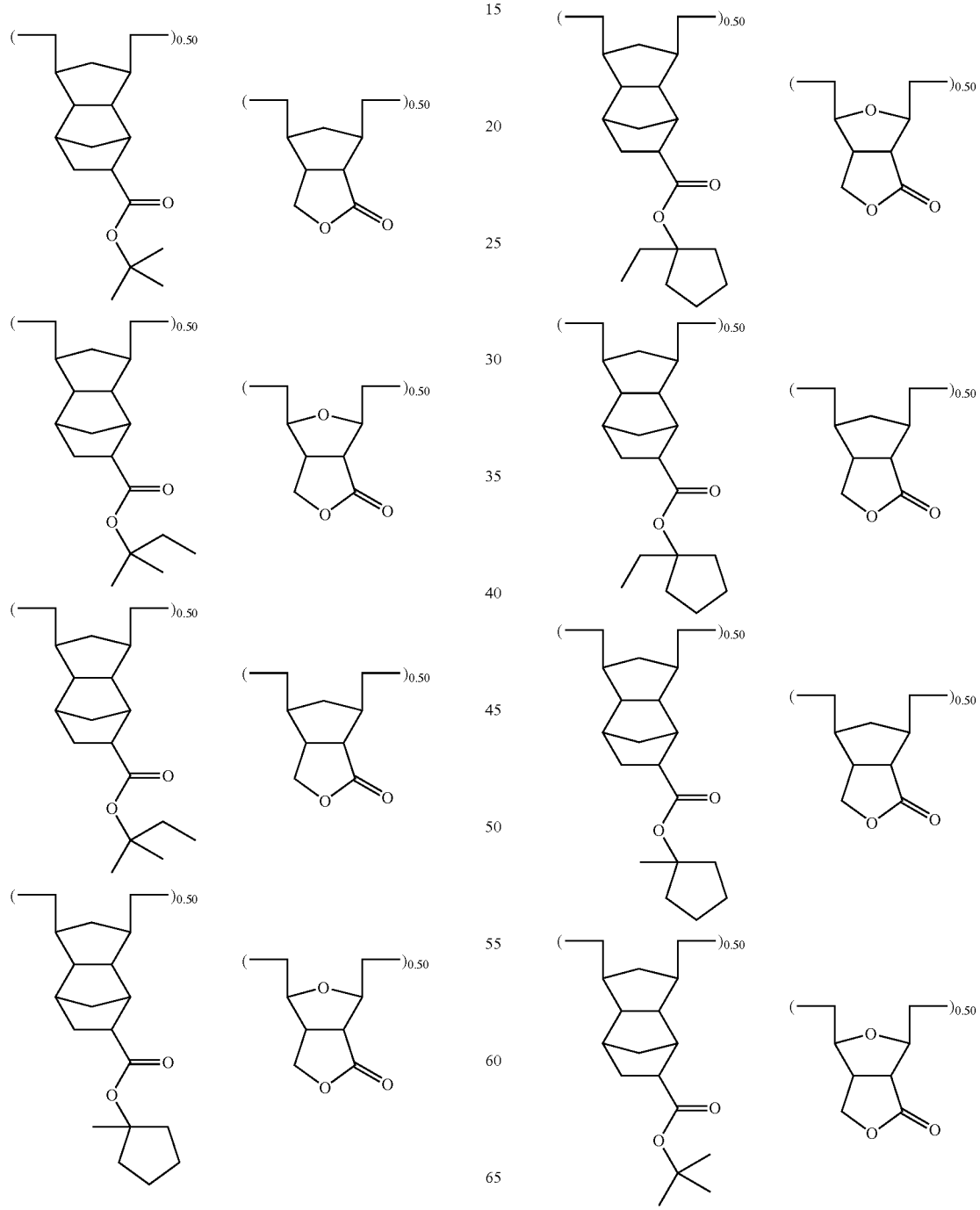
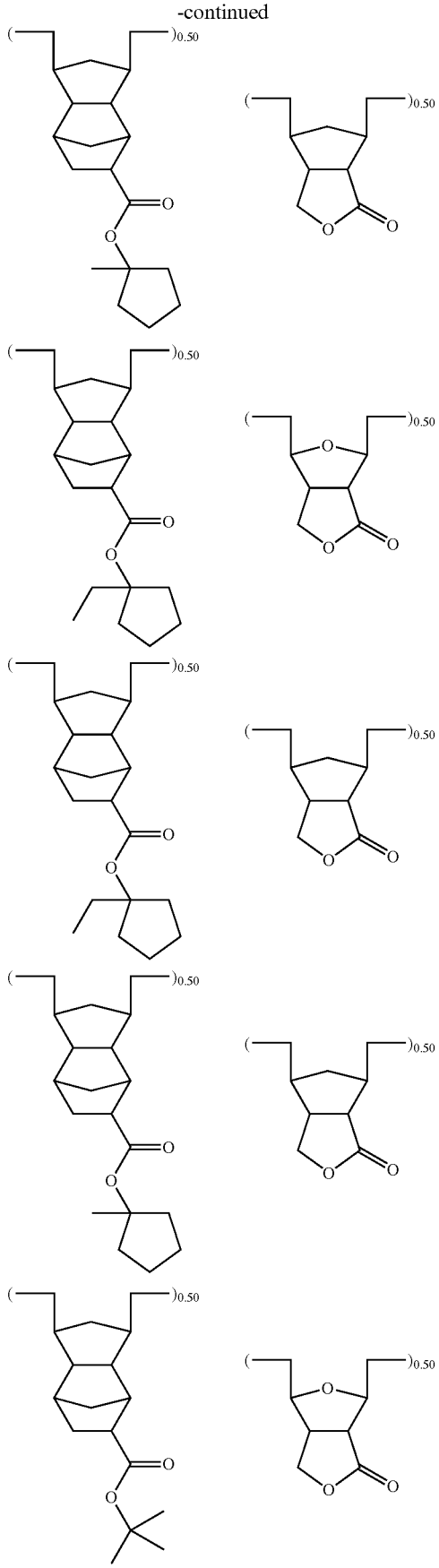

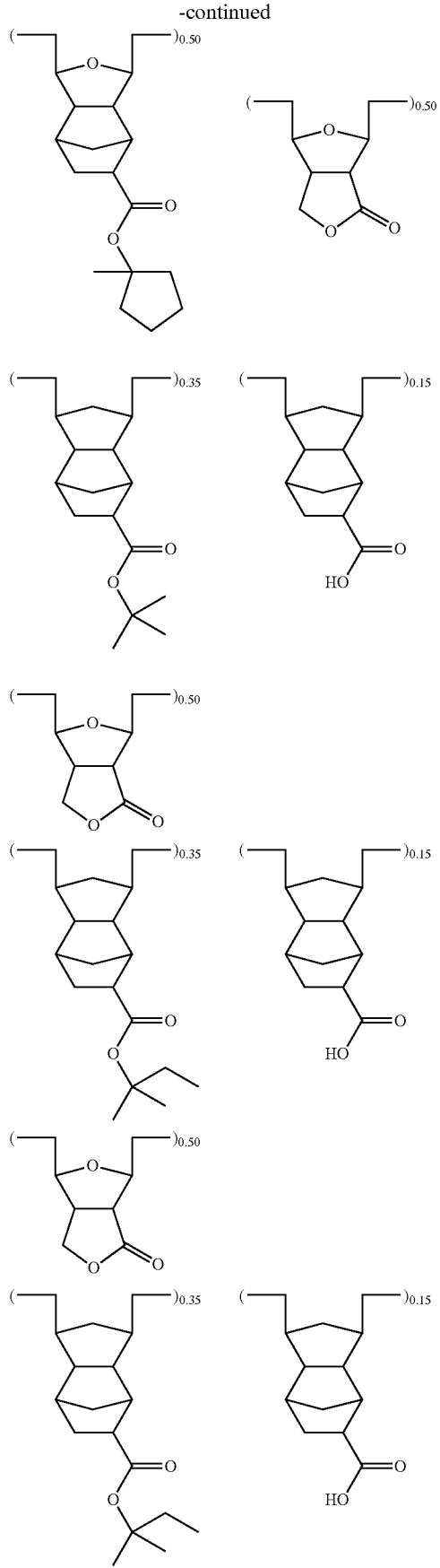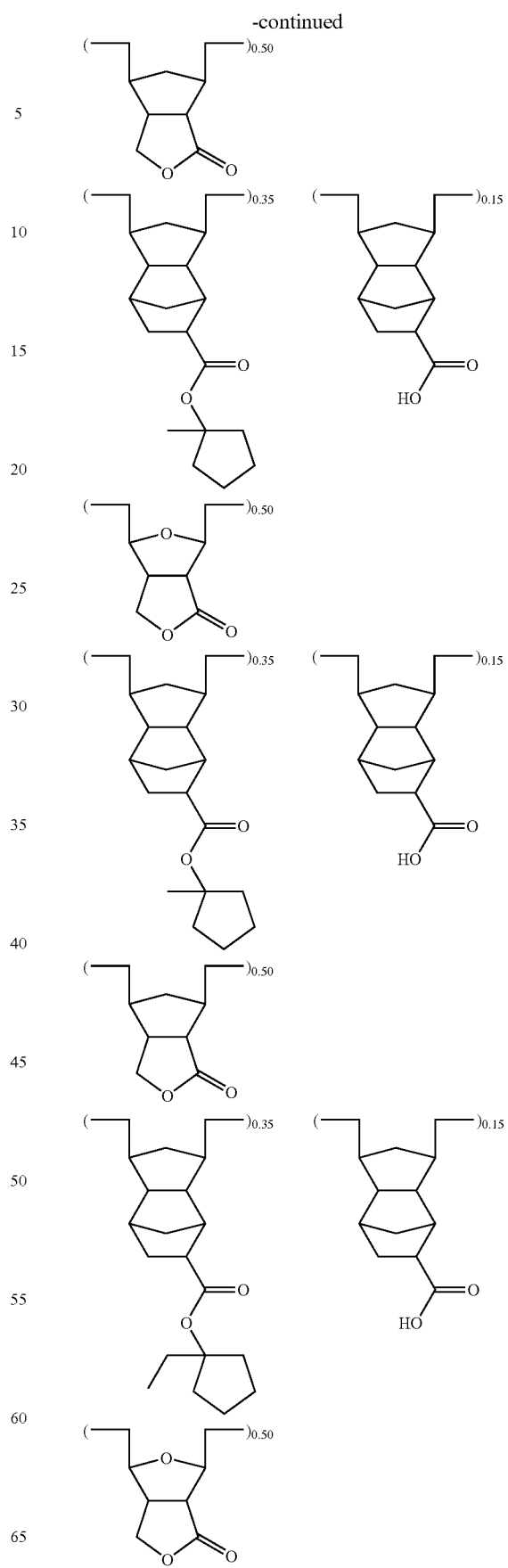

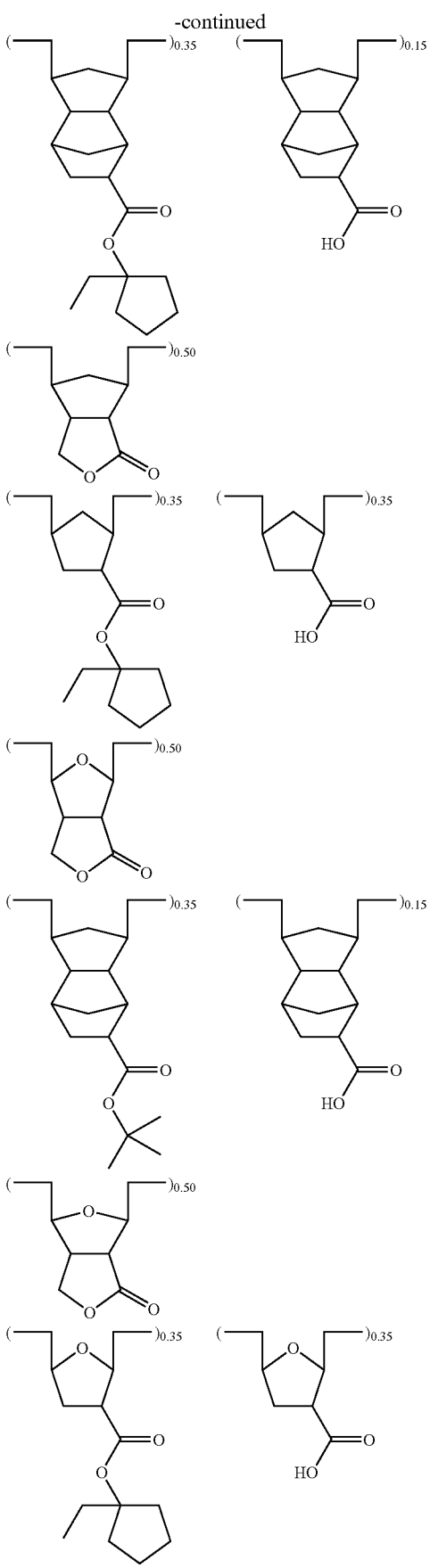
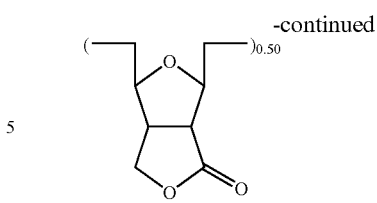

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer. The polymer is not limited to one type and a mixture of two or more polymers may be added. The use of plural polymers allows for easy adjustment of resist properties.

Acid Generator

In the resist composition of the invention, an acid generator is generally included. A typical acid generator is a photoacid generator (PAG) which may be any compound capable of generating an acid in response to high-energy radiation. Suitable photoacid generators include sulfonium salts, iodonium salts, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides.

Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium.

Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl) ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl) difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide.

A typical tris(substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations include diphenyliodonium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl) difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Iodonium salts based on combination of the foregoing examples are included.

N-sulfonyloxydicarboxylmide photoacid generators include combinations of imide skeletons with sulfonates. Exemplary imide skeletons are succinimide, naphthalenedicarboxylmide, phthalimide, cyclohexyldicarboxylmide, 5-norbornene-2,3-dicarboxylmide, and 7-oxabicyclo[2.2.1]-5-heptene-2,3-dicarboxylmide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy) naphthalene-2-sulfonate, 4-(p-toluenesulfonyloxy) naphthalene-1-sulfonate, 5-(p-toluenesulfonyloxy) naphthalene-1-sulfonate, 8-(p-toluenesulfonyloxy) naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl) difluoromethanesulfonate, and 4-oxo-1-adamantyloxycarbonyldifluoromethanesulfonate.

Suitable oxime sulfonate photoacid generators in the form of O-arylsulfonyloxime and O-alkylsulfonyloxime compounds include oxime sulfonates having an electron withdrawing group such as trifluoromethyl incorporated for increased stability, as represented by the formula (Ox-1).

(Ox-1)

Herein $R^{401}$ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is substituted or unsubstituted aromatic or hetero-aromatic group.

Examples include 2-[2,2,3,3,4,4,5,5-octafluoro-1-(nonafluorobutylsulfonyloxy-imino)pentyl]fluorene, 2-[2,2,3,3,4,4-pentafluoro-1-(nonafluorobutylsulfonyloxy-imino)butyl]fluorene, 2-[2,2,3,3,4,4,5,5,6,6-decafluoro-1-(nonafluorobutylsulfonyl-oxyimino)hexyl]fluorene, 2-[2,2,3,3,4,4,5,5-octafluoro-1-(nonafluorobutylsulfonyloxy-imino)pentyl]-4-biphenyl, 2-[2,2,3,3,4,4-pentafluoro-1-(nonafluorobutylsulfonyloxy-imino)butyl]-4-biphenyl, and 2-[2,2,3,3,4,4,5,5,6,6-decafluoro-1-(nonafluorobutylsulfonyl-oxyimino)hexyl]-4-biphenyl. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Among others, acid generators having, the general formula (4) are preferred.

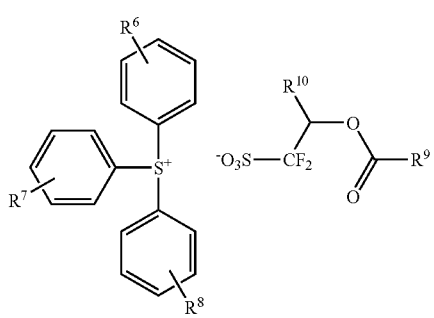

(4)

Herein $R^6$, $R^7$, and $R^8$ are each independently hydrogen or a straight, branched or cyclic, monovalent $C_1$-$C_{20}$ hydrocarbon group which may contain a heteroatom, $C_1$-$C_{10}$ alkoxy group or halogen. $R^9$ is a straight, branched or cyclic, monovalent $C_1$-$C_{30}$ hydrocarbon group which may contain a heteroatom. $R^{10}$ is hydrogen or trifluoromethyl.

$R^6$, $R^7$, and $R^8$ are each independently hydrogen or a straight, branched or cyclic, monovalent $C_1$-$C_{20}$ hydrocarbon group which may contain a heteroatom, $C_1$-$C_{10}$ alkoxy group or halogen. Examples of the hydrocarbon group optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^9$ is a straight, branched or cyclic, monovalent $C_1$-$C_{30}$ hydrocarbon group which may contain a heteroatom, examples of which are exemplified below, but are not limited thereto.

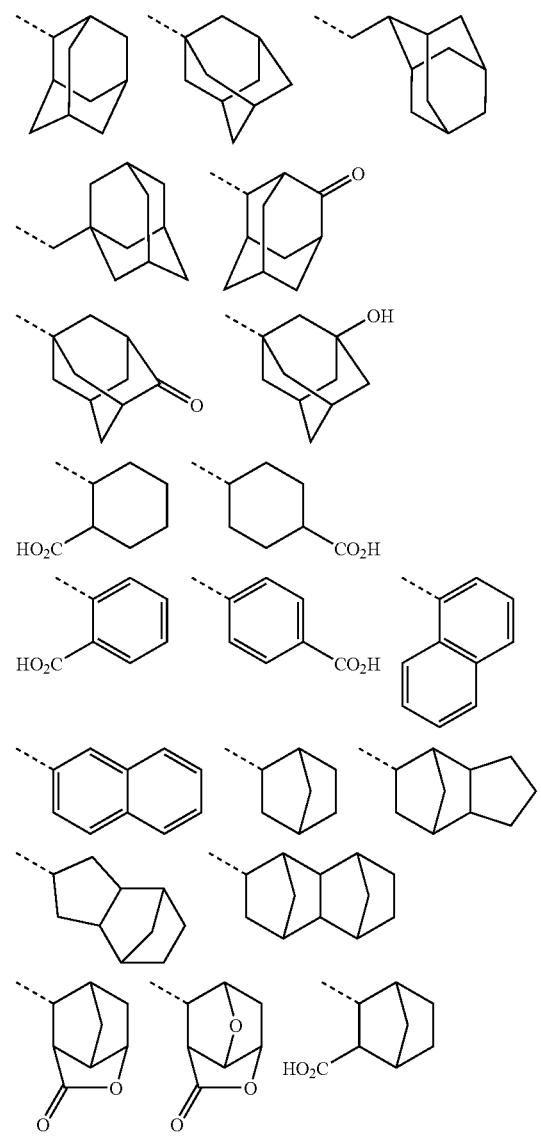

53
-continued
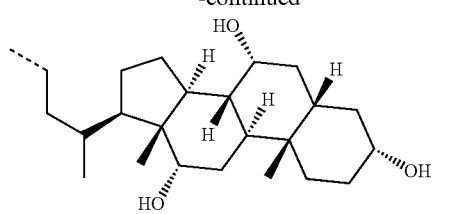
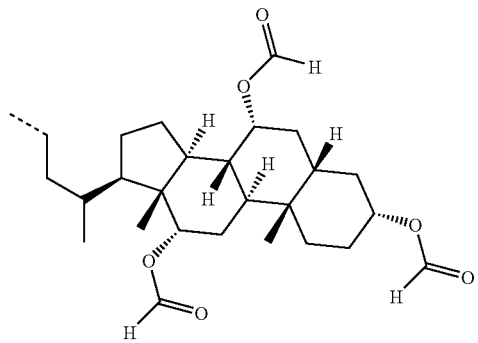
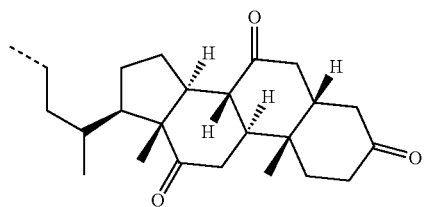
Illustrative examples of the acid generator having formula (4) are shown below.
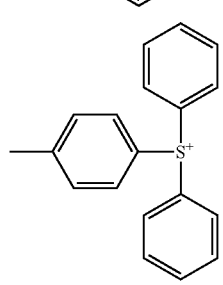
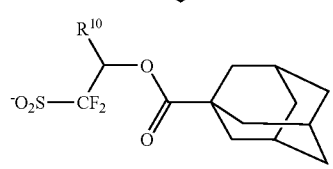
54
-continued
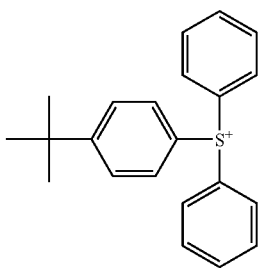
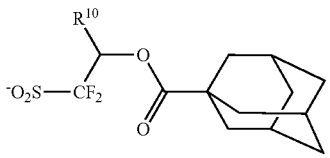
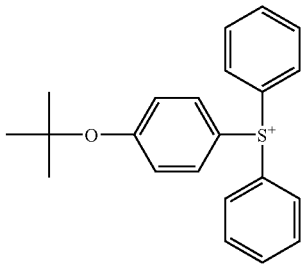
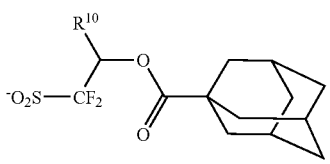
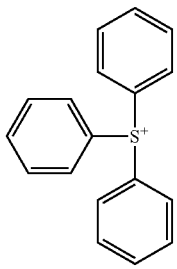 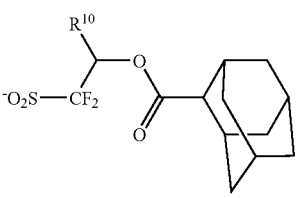
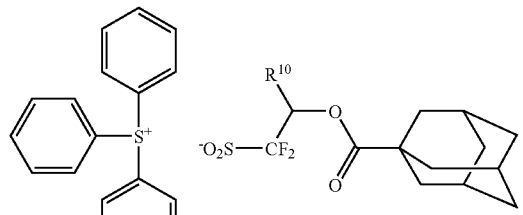

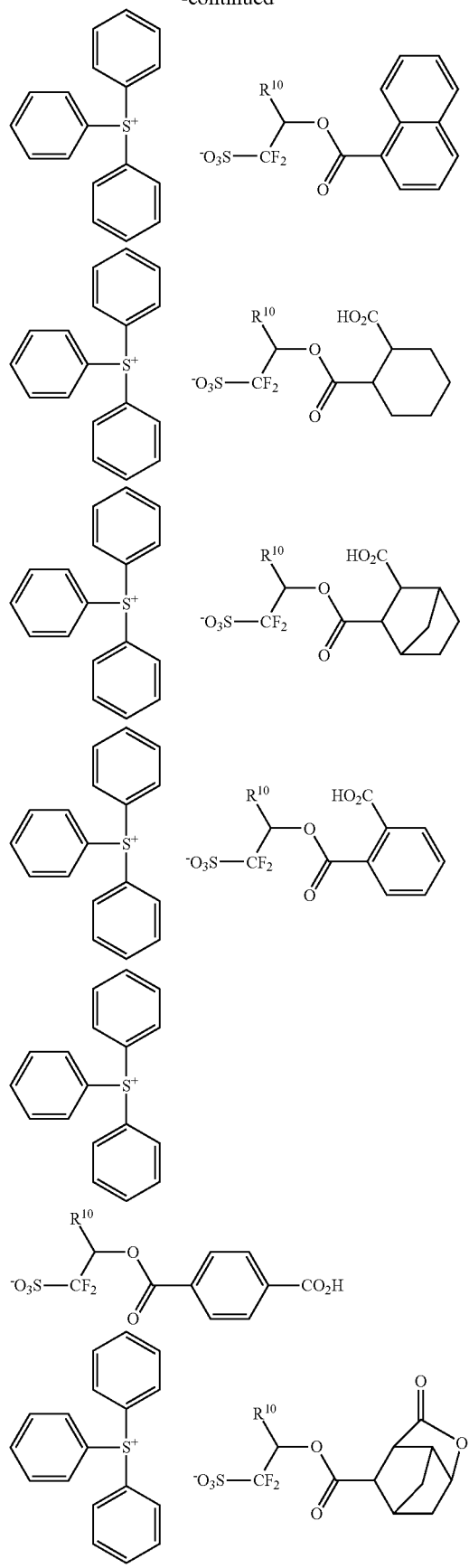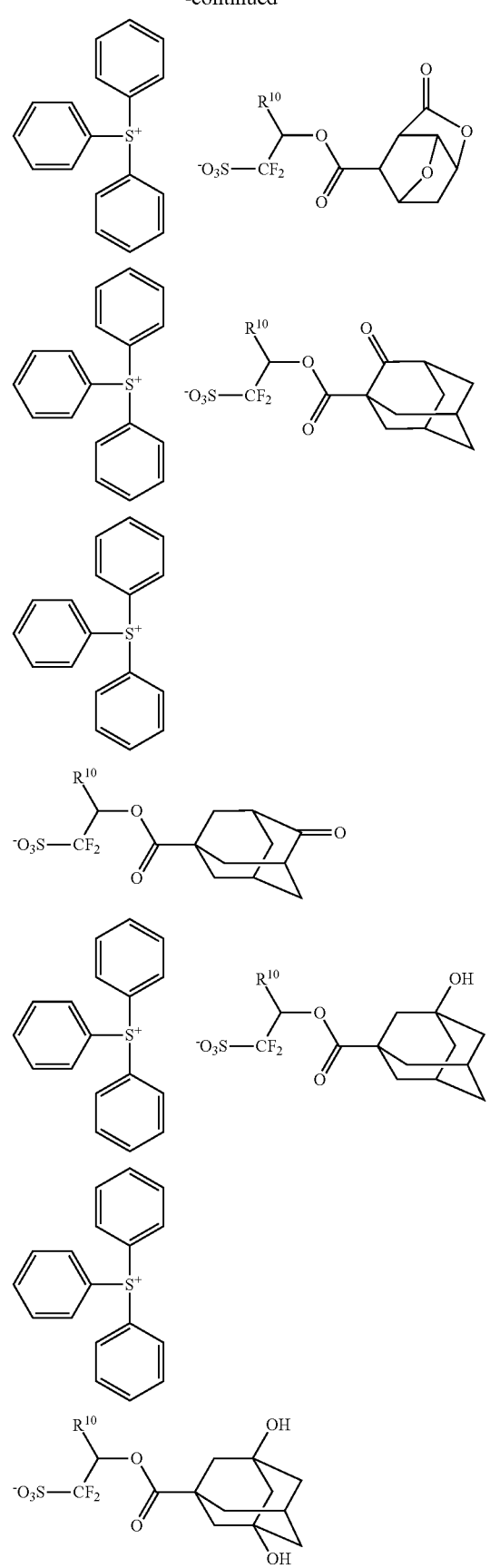

-continued

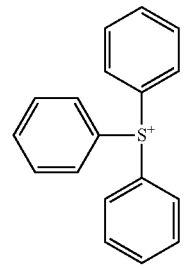

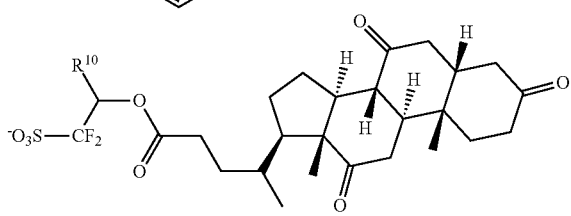

Herein $R^{10}$ is hydrogen or trifluoromethyl.

Since the anion moiety in the acid generator having formula (4) has an ester site, it is easy to introduce less bulky and bulky acyl groups, benzoyl, naphthoyl and anthracenecarbonyl groups. The acid generator having formula (4) has a wide spectrum of molecular design and makes it easy to adjust solvent solubility and transmittance and to control the diffusion of the acid generated therefrom. While the sulfonic acid generated from the acid generator having formula (4) has a strong acidity comparable to perfluoroalkanesulfonic acids, it is highly compatible with and well dispersible in the base resin because of a low fluorine content, from which a reduction of roughness is expectable. It has been found that roughness is minimized particularly when the acid generator having formula (4) is combined with a resist base resin comprising recurring units derived from the acid-labile ester monomer of specific spirocyclic structure. The acid generator having formula (4) raises no problems when used in the device fabrication process including coating, prebaking, exposure, PEB, and development steps. When used in the ArF immersion lithography, it is least leached out in water and least affected by water remaining on the wafer, inhibiting defect formation. In the disposal of resist-containing waste liquid after the device fabrication, the acid generator having formula (4) can be transformed into less accumulative compounds of lower molecular weight since its ester site is hydrolyzable under basic conditions. In the disposal by combustion, the acid generator is more combustible because of a low degree of fluorine substitution, with a low environmental load being expectable.

In the chemically amplified resist composition, the PAG (B) may be added in any desired amount as long as the objects of the invention are not compromised. An appropriate amount of PAG is 0.1 to 40 parts, and more preferably 2 to 30 parts by weight per 100 parts by weight of the base resin in the composition. Too high a proportion of PAG may give rise to problems of degraded resolution and foreign matter upon development and resist film peeling. The PAG may be used alone or in admixture of two or more. The transmittance of the resist film can be controlled by using a PAG having a low transmittance at the exposure wavelength and adjusting the amount of the PAG added.

It is noted that an acid diffusion controlling function may be provided when two or more PAG's are used in admixture provided that one PAG is an onium salt capable of generating a weak acid. Specifically, in a system using a mixture of a PAG capable of generating a strong acid (e.g., fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid is used, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts (0 to 2 pbw), and especially up to 1 part by weight (0 to 1 pbw) per 100 parts by weight of the base resin. Excessive amounts of the acid amplifier compound may make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, PGMEA, and mixtures thereof because the acid generator is most soluble therein.

An appropriate amount of the organic solvent used is 200 to 5,000 parts, especially 400 to 3,000 parts by weight per 100 parts by weight of the base resin.

N-Containing Compound

In the resist composition, an organic nitrogen-containing compound or compounds may be compounded as component (D). The organic nitrogen-containing compound used herein is preferably a compound capable of suppressing the rate of diffusion when the acid generated by the acid generator diffuses within the resist film. The inclusion of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

Suitable organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives.

Examples of suitable primary aliphatic amines include methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

In addition, organic nitrogen-containing compounds of the following general formula (B)-1 may also be included alone or in admixture.

$$N(X)_n(Y)_{3-n} \tag{B)-1}$$

In the formula, n is equal to 1, 2 or 3; side chain Y is independently hydrogen or a straight, branched or cyclic $C_1$-$C_{20}$ alkyl group which may contain an ether or hydroxyl group; and side chain X is independently selected from groups of the following general formulas (X)-1 to (X)-3, and two or three X's may bond together to form a ring.

$$\text{—[ R}^{300}\text{—O—R}^{301}\text{ ]} \tag{X-1}$$

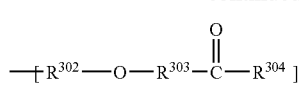  (X-2)

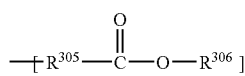  (X-3)

In the formulas, $R^{300}$, $R^{302}$ and $R^{305}$ are independently straight or branched $C_1$-$C_4$ alkylene groups; $R^{301}$ and $R^{304}$ are independently hydrogen or a straight, branched or cyclic $C_1$-$C_{20}$ alkyl group which may contain one or more hydroxyl, ether, ester groups or lactone rings; $R^{303}$ is a single bond or a straight or branched $C_1$-$C_4$ alkylene group; and $R^{306}$ is a straight, branched or cyclic $C_1$-$C_{20}$ alkyl group which may contain one or more hydroxyl, ether, ester groups or lactone rings.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more organic nitrogen-containing compounds having cyclic structure represented by the following general formula (B)-2.

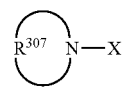  (B)-2

Herein X is as defined above, and $R^{307}$ is a straight or branched $C_2$-$C_{20}$ alkylene group which may contain one or more carbonyl, ether, ester or sulfide groups.

Illustrative examples of the organic nitrogen-containing compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Also, one or more organic nitrogen-containing compounds having cyano group represented by the following general formulae (B)-3 to (B)-6 may be blended.

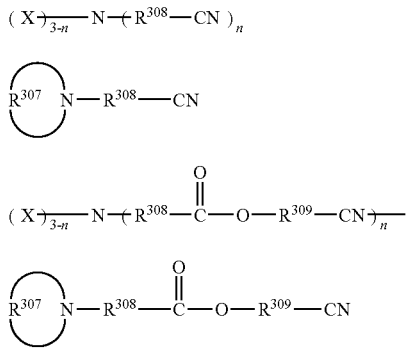

Herein, X, $R^{307}$ and n are as defined above, and $R^{308}$ and $R^{308}$ are each independently a straight or branched $C_1$-$C_4$ alkylene group.

Illustrative examples of the organic nitrogen-containing compounds having cyano represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds of imidazole structure having a polar functional group, represented by the general formula (B)-7.

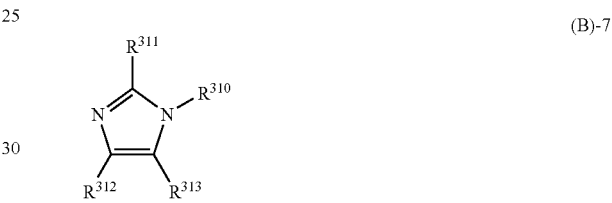

Herein, $R^{310}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{311}$, $R^{312}$ and $R^{313}$ are each independently hydrogen, a straight, branched or cyclic $C_1$-$C_{10}$ alkyl group, aryl group or aralkyl group.

Also included are organic nitrogen-containing compounds of benzimidazole structure having a polar functional group, represented by the general formula (B)-8.

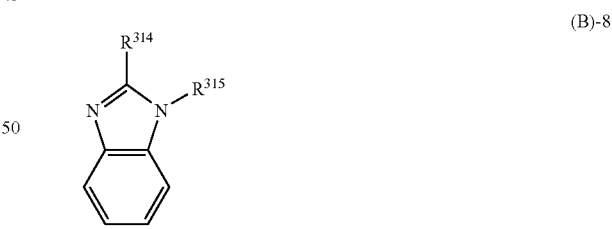

Herein, $R^{314}$ is hydrogen, a straight, branched or cyclic $C_1$-$C_{10}$ alkyl group, aryl group or aralkyl group. $R^{315}$ is a polar functional group-bearing, straight, branched or cyclic $C_1$-$C_{20}$ alkyl group, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

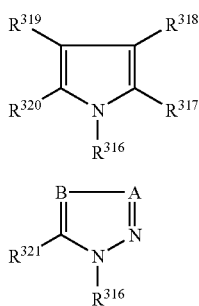

(B)-9

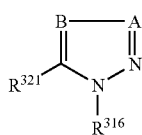

(B)-10

Herein, A is a nitrogen atom or $=$C—$R^{322}$, B is a nitrogen atom or $=$C—$R^{323}$, $R^{316}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently hydrogen, a straight, branched or cyclic $C_1$-$C_{10}$ alkyl group or aryl group, or a pair of $R^{317}$ and $R^{318}$ and a pair of $R^{319}$ and $R^{320}$, taken together, may form a benzene, naphthalene or pyridine ring with the carbon atoms to which they are attached; $R^{321}$ is hydrogen, a straight, branched or cyclic $C_1$-$C_{10}$ alkyl group or aryl group; $R^{322}$ and $R^{323}$ each are hydrogen, a straight, branched or cyclic $C_1$-$C_{10}$ alkyl group or aryl group, or a pair of $R^{321}$ and $R^{323}$, taken together, may form a benzene or naphthalene ring with the carbon atoms to which they are attached.

Also included are organic nitrogen-containing compounds of aromatic carboxylic ester structure having the general formulae (B)-11 to (B)-14.

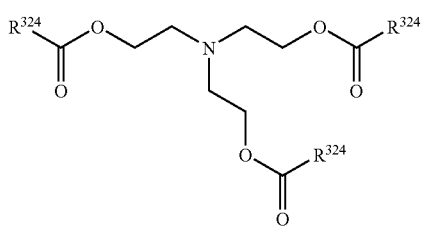

(B)-11

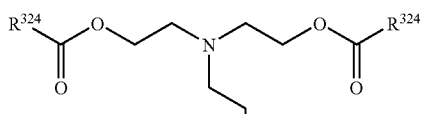

(B)-12

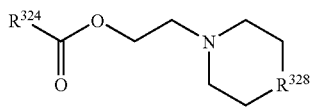

(B)-13

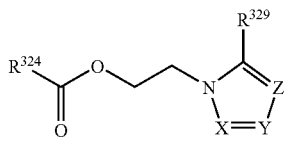

(B)-14

Herein $R^{324}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{329}$ is a single bond, methylene, ethylene, sulfur atom or —$O(CH_2CH_2O)_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring with the carbon atoms to which they are attached.

Further included are organic nitrogen-containing compounds of 7-oxanorbornane-2-carboxylic ester structure having the general formula (B)-15.

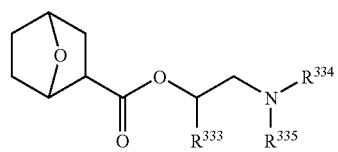

(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms with the nitrogen atom to which they are attached.

The organic nitrogen-containing compounds may be used alone or in admixture of two or more. The organic nitrogen-containing compound is preferably formulated in an amount of 0.001 to 20 parts, and especially 0.01 to 10 parts by weight, per 100 parts by weight of the base resin (B). Less than 0.001 pbw of the nitrogen-containing compound fails to achieve the desired addition effect whereas more than 20 pbw may lead to too low sensitivity.

The resist composition of the invention may include optional ingredients, for example, (E) a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from DIC Corp., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

In the resist composition, an additive polymer may be added as another optional ingredient. This additive polymer tends to segregate in the sub-surface region of the resist film and has the functions of tailoring the hydrophilic/hydrophobic balance of the surface, enhancing water repellency, and/or preventing low-molecular-weight fractions from flowing into or out of the resist film when the resist film is in contact with water or another liquid. Such a segregating polymer may be added in conventional amounts as long as the objects of the invention are not compromised and preferably in an amount of up to 15 parts, and more preferably up to 10 parts by weight per 100 parts by weight of the base resin. The lower limit above which the segregating polymer can exert its effect is preferably 1 part.

The segregating polymer is preferably selected from homopolymers and copolymers comprising fluorine-containing units of one or more types, and copolymers comprising fluorine-containing units and other units. Exemplary fluorine-containing units and other units are illustrated below, but not limited thereto.

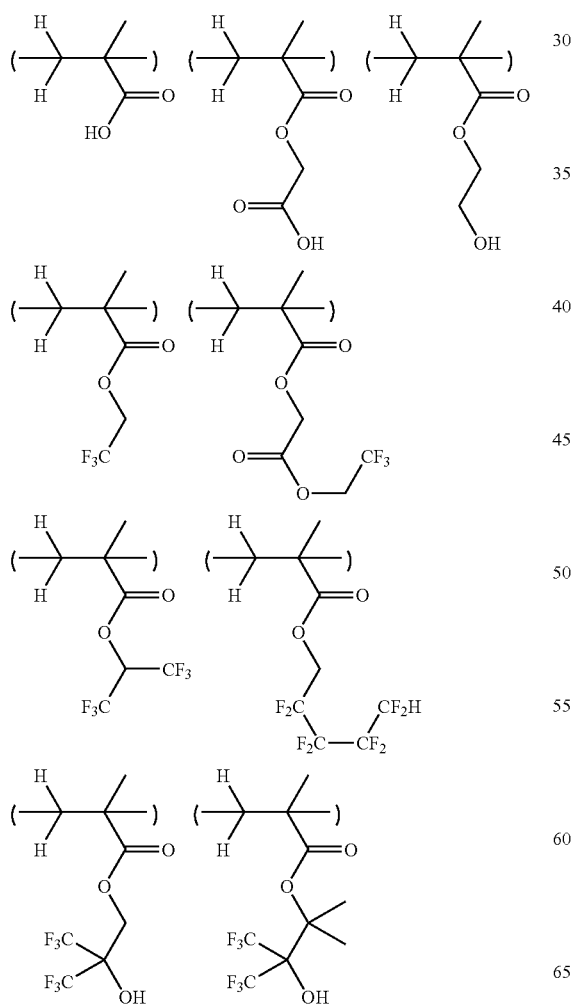
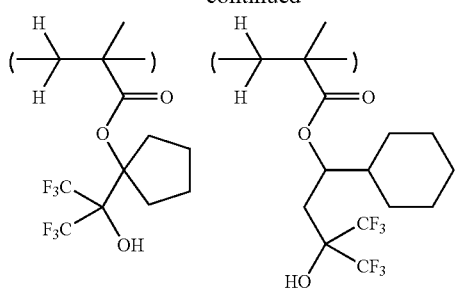
-continued
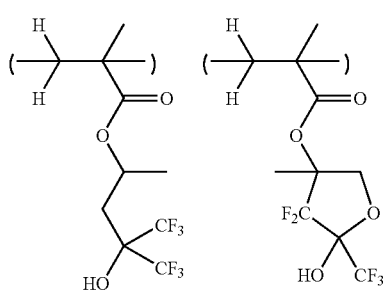
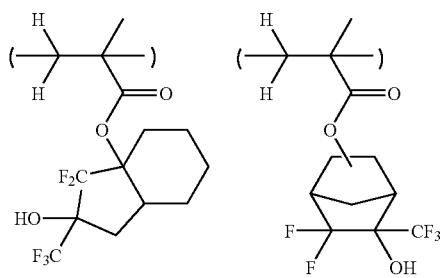
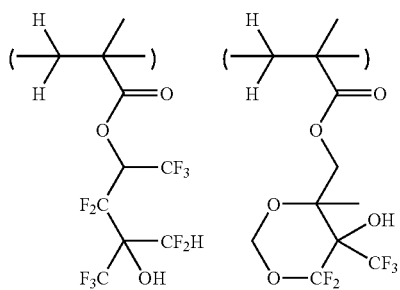
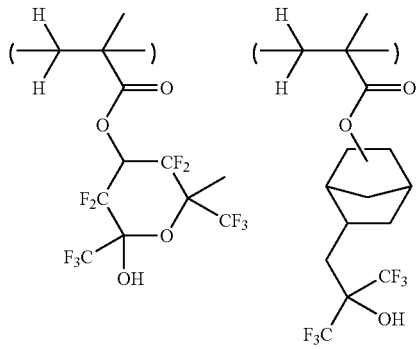

-continued

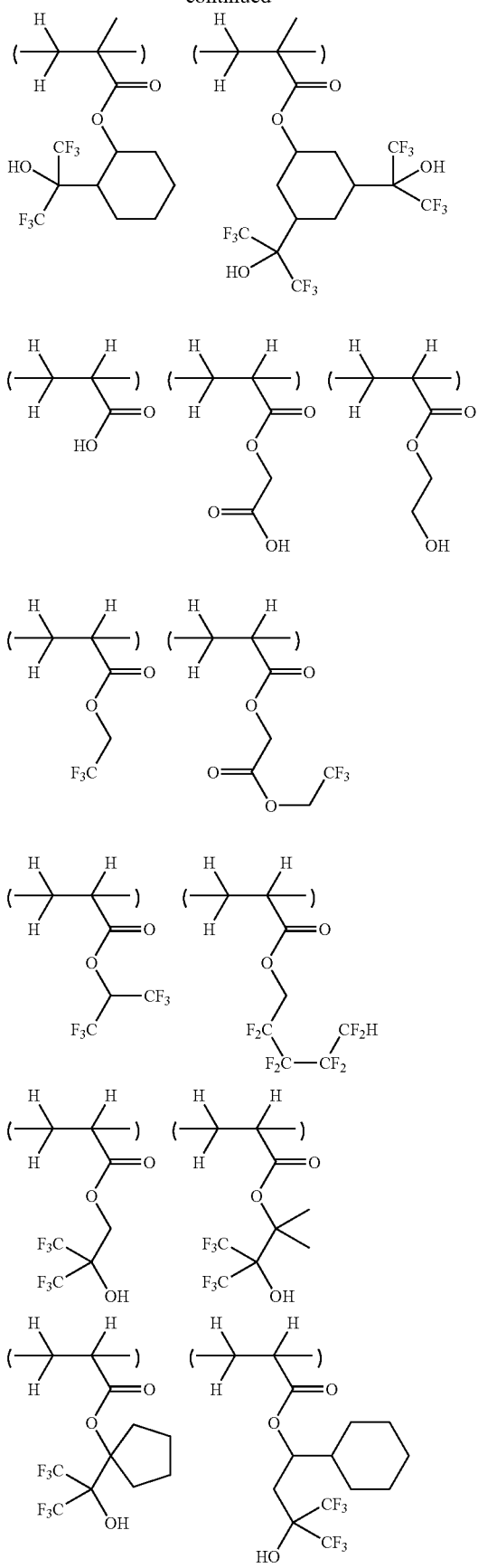
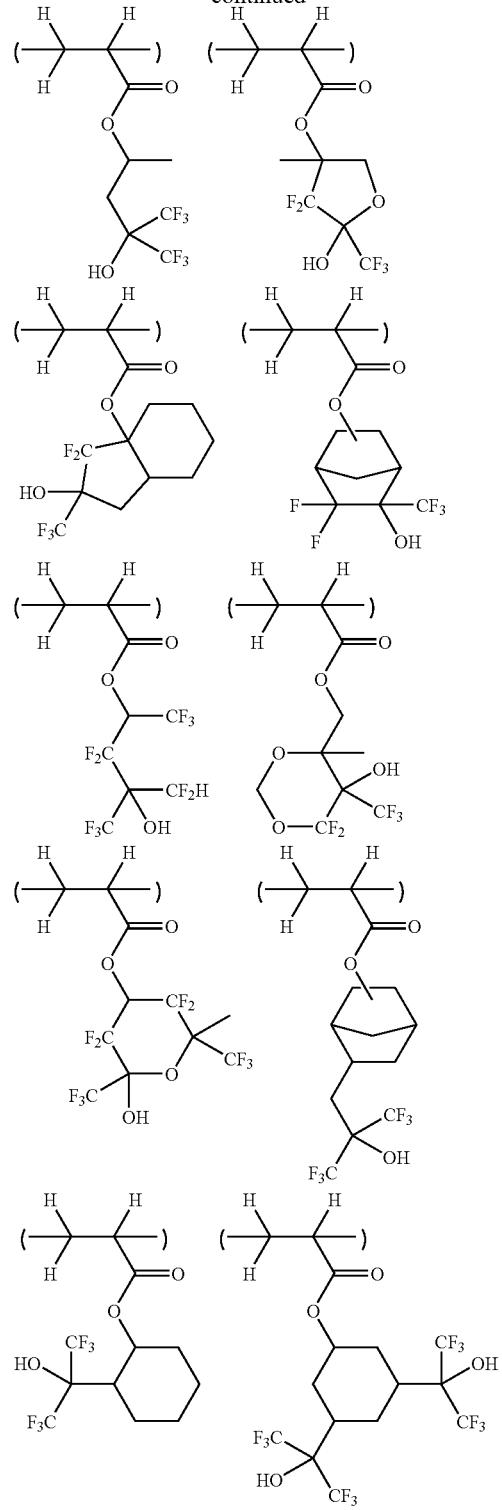

Preferably the segregating polymer has a weight average molecular weight of 1,000 to 50,000, and more preferably 2,000 to 20,000, as measured by GPC versus polystyrene standards. Outside the range, the surface modifying effect may be insufficient or development defects may form.

While the resist composition of the invention typically comprises a polymer or base resin, acid generator, organic solvent and nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be performed by well-known lithography processes. The process generally involves coating, heat treatment (or prebaking), exposure, heat treatment (post-exposure baking, PEB), and development. If necessary, any additional steps may be added.

For pattern formation, the resist composition is first applied onto a substrate (on which an integrated circuit is to be formed, e.g., Si, $SiO_2$, SiN, SiON, TiN, WSi, BPSG, SOG, organic antireflective coating, Cr, CrO, CrON, MoSi, etc.) by a suitable coating technique such as spin coating, roll coating, flow coating, dip coating, spray coating or doctor coating. The coating is prebaked on a hot plate at a temperature of 50 to 150° C. for 1 to 10 minutes, preferably 60 to 140° C. for 1 to 5 minutes. The resulting resist film is generally 0.01 to 2.0 µm thick.

A relationship of a reduced thickness of resist film to an etch selectivity ratio between resist film and processable substrate imposes severer limits on the process. Under consideration is the tri-layer process in which a resist layer, a silicon-containing intermediate layer, an undercoat layer having a high carbon density and high etch resistance, and a processable substrate are laminated in sequence from top to bottom. On etching with oxygen gas, hydrogen gas, ammonia gas or the like, a high etch selectivity ratio is available between the silicon-containing intermediate layer and the undercoat layer, which allows for thickness reduction of the silicon-containing intermediate layer. A relatively high etch selectivity ratio is also available between the monolayer resist and the silicon-containing intermediate layer, which allows for thickness reduction of the monolayer resist. The method for forming the undercoat layer in this case includes a coating and baking method and a CVD method. In the case of coating, novolac resins and resins obtained by polymerization of fused ring-containing olefins are used. In the CVD film formation, reactant gases such as butane, ethane, propane, ethylene and acetylene are used. For the silicon-containing intermediate layer, either a coating method or a CVD method may be employed. The coating method uses silsesquioxane, polyhedral oligomeric silsesquioxane (POSS) and the like while the CVD method uses silane gases as the reactant. The silicon-containing intermediate layer may have an antireflection function with a light absorbing ability and have photo-absorptive groups like phenyl groups, or it may be a SiON film. An organic film may be formed between the silicon-containing intermediate layer and the photoresist, and the organic film in this case may be an organic antireflective coating. After the photoresist film is formed, deionized water rinsing (or post-soaking) may be carried out for extracting the photoacid generator and the like from the film surface or washing away particles, or a protective film may be coated.

With a mask having a desired pattern placed above the resist film, the resist film is then exposed to radiation such as UV, deep-UV, electron beam, x-ray, excimer laser light, γ-ray and synchrotron radiation. The exposure dose is preferably about 1 to 200 $mJ/cm^2$, more preferably about 10 to 100 $mJ/cm^2$. The film is further baked on a hot plate at 60 to 150° C. for 1 to 5 minutes, preferably 80 to 120° C. for 1 to 3 minutes (PEB). Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate. It is appreciated that the resist composition of the invention is suited for nano-scale patterning using such high-energy radiation as deep UV with a wavelength of 254 to 193 nm, vacuum UV with a wavelength of 157 nm, electron beam, soft x-ray, x-ray, excimer laser light, γ-ray and synchrotron radiation, and best suited for nano-scale patterning using high-energy radiation in the wavelength range of 180 to 200 nm.

Immersion lithography can be applied to the resist composition of the invention. The ArF immersion lithography uses a liquid having a refractive index of at least 1 and highly transparent at the exposure wavelength such as deionized water or alkanes as the immersion solvent. The immersion lithography involves prebaking a resist film and exposing the resist film to light through a projection lens, with deionized water or similar liquid interposed between the resist film and the projection lens. Since this allows projection lenses to be designed to a numerical aperture (NA) of 1.0 or higher, formation of finer size patterns is possible. The immersion lithography is important for the ArF lithography to survive to the 45-nm node, with a further development thereof being accelerated. In the case of immersion lithography, deionized water rinsing (or post-soaking) may be carried out after exposure for removing water droplets left on the resist film, or a protective coating may be applied onto the resist film after pre-baking, for preventing any leach-out from the resist and improving water slip on the film surface. The resist protective coating used in the immersion lithography is preferably formed from a solution of a polymer having 1,1,1,3,3,3-hexafluoro-2-propanol residue which is insoluble in water, but soluble in an alkaline developer liquid, in a solvent selected from alcohols of at least 4 carbon atoms, ethers of 8 to 12 carbon atoms, and mixtures thereof.

The water immersion lithography using a NA 1.35 lens achieves an ultimate resolution of 40 to 38 nm at the maximum NA, but cannot reach 32 nm. Efforts have been made to develop higher refractive index materials in order to further increase NA. It is the minimum refractive index among projection lens, liquid, and resist film that determines the NA limit of lenses. In the case of water immersion, the refractive index of water is the lowest in comparison with the projection lens (refractive index 1.5 for synthetic quartz) and the resist film (refractive index 1.7 for prior art methacrylate-based film). Thus the NA of projection lens is determined by the refractive index of water. Recent efforts succeeded in developing a highly transparent liquid having a refractive index of 1.65. In this situation, the refractive index of projection lens made of synthetic quartz is the lowest, suggesting a need to develop a projection lens material with a higher refractive index. LuAG (lutetium aluminum garnet $Lu_3Al_5O_{12}$) having a refractive index of at least 2 is the most promising material.

The resist composition of the invention is applicable to immersion lithography using a high refractive index liquid.

The process that now draws attention as the technology for extending the life of the ArF lithography is a double patterning process involving a first set of exposure and development to form a first pattern and a second set of exposure and development to form a second pattern between features of the first pattern. See Proc. SPIE Vol. 5754, p 1508 (2005). A number of double patterning processes have been proposed. One exemplary process involves a first set of exposure and development to form a photoresist pattern having lines and spaces at intervals of 1:3, processing the underlying layer of hard mask by dry etching, applying another layer of hard mask thereon, a second set of exposure and development of a photoresist film to form a line pattern in the spaces of the first exposure, and processing the hard mask by dry etching, thereby forming a line-and-space pattern at a half pitch of the first pattern. An alternative process involves a first set of exposure and development to form a photoresist pattern having spaces and lines at intervals of 1:3, processing the underlying layer of hard mask by dry etching, applying a photoresist layer thereon, a second set of exposure and development to form a second space pattern on the remaining hard mask portion, and processing the hard mask by dry etching. In either process, the hard mask is processed by two dry etchings.

While the former process requires two applications of hard mask, the latter process uses only one layer of hard mask, but requires to form a trench pattern which is difficult to resolve as compared with the line pattern. The latter process includes the use of a negative resist material in forming the trench pattern. This allows for use of high contrast light as in the formation of lines as a positive pattern. However, since the negative resist material has a lower dissolution contrast than the positive resist material, a comparison of the formation of lines from the positive resist material with the formation of a trench pattern of the same size from the negative resist material reveals that the resolution achieved with the negative resist material is lower. After a wide trench pattern is formed from the positive resist material by the latter process, there may be applied a thermal flow method of heating the substrate for shrinkage of the trench pattern, or a RELACS method of coating a water-soluble film on the trench pattern as developed and heating to induce crosslinking at the resist film surface for achieving shrinkage of the trench pattern. These have the drawbacks that the proximity bias is degraded and the process is further complicated, leading to reduced throughputs.

Both the former and latter processes require two etchings for substrate processing, leaving the issues of a reduced throughput and deformation and misregistration of the pattern by two etchings. One method that proceeds with a single etching is by using a negative resist material in a first exposure and a positive resist material in a second exposure. Another method is by using a positive resist material in a first exposure and a negative resist material in a higher alcohol of 4 or more carbon atoms, in which the positive resist material is not dissolvable, in a second exposure. However, these methods using negative resist materials with low resolution entail degradation of resolution.

If first exposure is followed by second exposure at a half-pitch shifted position, the optical energy of second exposure offsets the optical energy of first exposure so that the contrast becomes zero. If a contrast enhancement layer (CEL) is formed on the resist film, the incident light to the resist film becomes nonlinear so that the first and second exposures do not offset each other. Thus an image having a half pitch is formed. See Jpn. J. Appl. Phy. Vol. 33 (1994) p 6874-6877. It is expected that similar effects are produced by using an acid generator capable of two photon absorption to provide a nonlinear contrast.

The critical issue associated with double patterning is an overlay accuracy between first and second patterns. Since the magnitude of misregistration is reflected by a variation of line size, an attempt to form 32-nm lines at an accuracy of 10%, for example, requires an overlay accuracy within 3.2 nm. Since currently available scanners have an overlay accuracy of the order of 8 nm, a significant improvement in accuracy is necessary.

Now under investigation is the resist pattern freezing technology involving forming a first resist pattern on a substrate, taking any suitable means for insolubilizing the resist pattern with respect to the resist solvent and alkaline developer, applying a second resist thereon, and forming a second resist pattern in space portions of the first resist pattern. With this freezing technology, etching of the substrate is required only once, leading to improved throughputs and avoiding the problem of misregistration due to stress relaxation of the hard mask during etching. In the freezing technology, development efforts are focused on the step of forming a resist film on the first resist pattern and the optical or thermal step of insolubilizing the resist pattern. The resist composition of the invention is also applicable to such a process. Examples of light used for the freezing purpose include preferably light with a wavelength of up to 300 nm, more preferably up to 200 nm, specifically ArF excimer light of wavelength 193 nm, $Xe_2$ excimer light of 172 nm, $F_2$ excimer light of 157 nm, $Kr_2$ excimer light of 146 nm, and $Ar_2$ excimer light of 126 nm, and the exposure dose in the case of light is preferably in the range of 10 $mJ/cm^2$ to 10 $J/cm^2$. Irradiation from an excimer laser of sub-200 nm wavelength, especially 193 nm, 172 nm, 157 nm, 146 nm, and 122 nm, or an excimer lamp not only causes the photoacid generator to generate an acid, but also promotes photo-induced crosslinking reaction. In a further example where a thermal acid generator in the form of an ammonium salt is added to a photoresist composition, specifically in an amount of 0.001 to 20 parts, more specifically 0.01 to 10 parts by weight per 100 parts by weight of the base resin, an acid can be generated by heating. In this case, acid generation and crosslinking reaction proceed simultaneously. The preferred heating conditions include a temperature of 100 to 300° C., and especially 130 to 250° C., and a time of 10 to 300 seconds. As a result, a crosslinked resist film is formed which is insoluble in solvents and alkaline developers.

EXAMPLE

Examples of the invention are given below by way of illustration and not by way of limitation. All parts (pbw) and percents (%) are by weight unless otherwise stated. The abbreviation "Mw" is a weight average molecular weight as measured by GPC using polystyrene standards. Me stands for methyl.

Monomers within the scope of the invention were synthesized according to the following formulation.

Synthesis Example 1

Synthesis of 6-methyl-6-spiro[4.5]decyl methacrylate (Monomer 1)

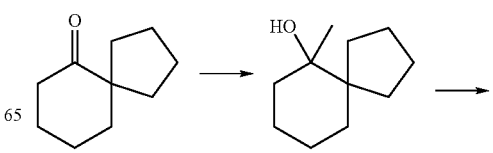

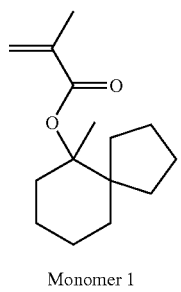

Monomer 1

With stirring under nitrogen atmosphere at room temperature, a mixture of 100 g of spiro[4.5]decan-6-one (which had been synthesized from cyclohexanone by a method as described in A. P. Krapcho, Synthesis, 1974, p 383 and references cited therein) and 200 ml of tetrahydrofuran was added dropwise to a tetrahydrofuran solution of 1.28 mol methylmagnesium chloride (which had been prepared from 31.1 g of metallic magnesium, 400 ml of tetrahydrofuran and chloromethane), during which time the temperature was kept below 60° C. The reaction mixture was refluxed for 30 minutes, after which a saturated ammonium chloride aqueous solution was added to stop the reaction. Through ordinary work-up of extraction, washing and drying, and subsequent vacuum distillation, there was obtained 93.3 g (yield 87%) of the target compound, 6-methylspiro[4.5]decan-6-ol.

6-methylspiro[4.5]decan-6-ol colorless liquid
boiling point: 55° C./6.7 Pa
IR (film): ν=3614, 3480, 2937, 2862, 1464, 1447, 1375, 1335, 1321, 1260, 1202, 1173, 1153, 1111, 1084, 1002, 925, 878 cm$^{-1}$
$^1$H-NMR (600 MHz in DMSO-$d_6$):
δ=1.03 (3H, s), 1.09-1.21 (3H, m), 1.26-1.62 (12H, m), 1.85 (1H, app dt, J=7, 13 Hz), 3.83 (1H, OH, s) ppm
$^{13}$C-NMR (150 MHz in DMSO-$d_6$):
δ=21.91, 22.24, 24.20, 25.55, 25.79, 32.39 (br), 33.84, 35.20, 37.97, 49.62, 71.77 ppm
GC-MS (EI): (m/z)$^+$=71, 108, 121, 135, 150, 168 (M$^+$)

With stirring under nitrogen atmosphere at 40° C., a mixture of 142.4 g of methacryloyl chloride and 300 ml of acetonitrile was added dropwise to a mixture of 156.82 g of 6-methylspiro[4.5]decan-6-ol, 183.8 g of triethylamine, 11 g of 4-dimethylaminopyridine, and 500 ml of acetonitrile. The reaction mixture was stirred for 4 hours at 40° C., for 20 hours at 50° C., and for 5 hours at 60° C., after which a saturated sodium hydrogencarbonate aqueous solution was added to stop the reaction. Through ordinary work-up of extraction, washing and drying, and subsequent vacuum distillation, there was obtained 163 g (yield 74%) of the target compound, 6-methyl-6-spiro[4.5]decyl methacrylate.

6-methyl-6-spiro[4.5]decyl methacrylate colorless liquid
boiling point: 77° C./10.6 Pa
IR (film): ν=2936, 2864, 1712, 1637, 1452, 1399, 1377, 1328, 1305, 1186, 1164, 1147, 1101, 1009, 935, 905, 813 cm$^{-1}$
$^1$H-NMR (600 MHz in DMSO-$d_6$):
δ=1.23-1.30 (2H, m), 1.32-1.46 (5H, m), 1.43 (3H, s), 1.47-1.59 (6H, m), 1.74 (1H, br), 1.85 (3H, br. s), 1.91 (1H, app dt, J=7, 13 Hz), 2.21 (1H, br), 5.58 (1H, app quint, J=2 Hz), 5.93 (1H, app s) ppm
$^{13}$C-NMR (150 MHz in DMSO-$d_6$):
δ=18.20, 19.34, 21.42, 21.48, 25.60, 25.80, 31.93, 33.11 (br), 34.15 (br), 34.96, 50.13, 86.57, 124.43, 137.67, 165.52 ppm In the $^{13}$C-NMR spectrum, a broadening was observed in the signal of some carbon atoms. In general, when equilibration between conformations is fast enough, a sharp peak appears at an average position corresponding to an abundance ratio of the respective conformations. This broadening indicates that equilibration between conformations is inhibited by steric hindrance.
GC-MS (EI): (m/z)$^+$=41, 69, 108, 135, 149, 236 (M$^+$)

To the NMR measurement sample was added a catalytic amount of trifluoromethanesulfonic acid. The sample was heated at 40° C. to facilitate elimination reaction. The structure of olefins resulting from elimination reaction was analyzed by $^1$H and $^{13}$C-NMR spectroscopy, identifying the following structures (mole percent in parentheses). Formation of a decalin-form olefin resulting from skeletal rearrangement due to 1,2-alkyl shift was observed.

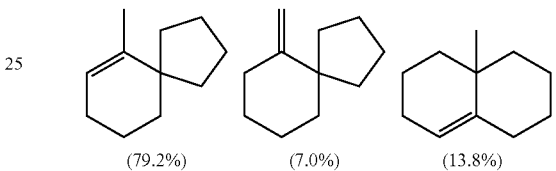

(79.2%)     (7.0%)     (13.8%)

Synthesis Example 2

Synthesis of 6-(6-ethylspiro[4.5]decyl)methacrylate (Monomer 2)

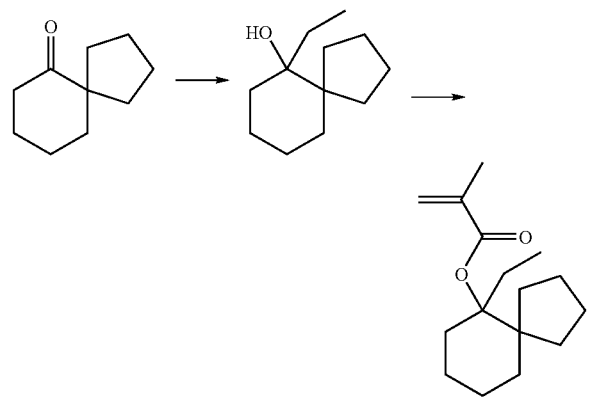

Monomer 2

With stirring under nitrogen atmosphere at −8° C., a mixture of 73.21 g of spiro[4.5]decan-6-one, 103.3 g of ethyl bromide and 500 g of tetrahydrofuran was added dropwise to a mixture of 13.16 g of metallic lithium and 270 g of tetrahydrofuran, during which time the temperature was kept below 0° C. Under ice cooling, a saturated ammonium chloride aqueous solution was added to the reaction mixture to stop the reaction. Through ordinary work-up of extraction, washing and drying, and subsequent vacuum distillation, there was obtained 71.1 g (yield 81%) of the target compound, 6-ethylspiro[4.5]decan-6-ol.

6-ethylspiro[4.5]decan-6-ol colorless liquid boiling point: 68° C./16 Pa

IR (film): ν=3613, 3481, 2938, 2863, 1456, 1370, 1335, 1270, 1152, 1135, 1111, 1027, 1000, 972, 957, 897, 854, 799, 776 cm$^{-1}$ $^1$H-NMR (600 MHz in DMSO-$d_6$):

δ=0.78 (3H, t, J=7.3 Hz), 1.60-1.12 (1H, m), 1.15-1.67 (16H, m), 1.85 (1H, app dt, J=7, 13 Hz), 3.64 (1H, OH, s) ppm $^{13}$C-NMR (150 MHz in DMSO-$d_6$):

δ=27.30, 21.69, 22.10, 25.12, 25.51, 25.78, 31.63 (br), 31.90, 33.40, 35.02, 50.67, 73.28 ppm GC-MS (EI): (m/z)$^+$=67, 85, 108, 121, 135, 153, 164, 182 (M$^+$)

With stirring under nitrogen atmosphere at room temperature, 172 ml of a n-hexane solution of 2.64M n-butyllithium was added dropwise to a mixture of 80.0 g of 6-ethylspiro[4.5]decan-6-ol and 300 g of tetrahydrofuran. The mixture was stirred for 2 hours at 50-60° C., then cooled below 10° C. A mixture of 55 g of methacryloyl chloride and 220 ml of tetrahydrofuran was added dropwise to the reaction mixture, which was stirred overnight at room temperature. Under ice cooling, a saturated ammonium chloride aqueous solution was added to the reaction mixture to stop the reaction. Through ordinary work-up of extraction, washing and drying, and subsequent vacuum distillation, there was obtained 80.2 g (yield 73%) of the target compound, 6-(6-ethylspiro[4.5]decyl)methacrylate.

6-(6-ethylspiro[4.5]decyl)methacrylate colorless liquid boiling point: 83° C./20 Pa IR (film): ν=2939, 2865, 1713, 1637, 1451, 1398, 1377, 1326, 1298, 1182, 1144, 1102, 1035, 1007, 934, 923, 891, 874, 813 cm$^{-1}$ $^1$H-NMR (600 MHz in DMSO-$d_6$):

δ=0.89 (3H, t, J=7.3 Hz), 1.26-1.32 (2H, m), 1.34-1.44 (5H, m), 1.46-1.64 (6H, m), 1.67-1.75 (1H, m), 1.84-2.00 (3H, m), 1.85 (3H, br, s), 2.20-2.26 (1H, m), 5.58 (1H, br, s), 5.94 (1H, br, s) ppm $^{13}$C-NMR (150 MHz in DMSO-$d_6$):

δ=9.57, 18.30, 21.16, 21.46, 25.06, 25.43, 26.52, 30.60, 33.00 (br), 34.08 (br), 35.33, 51.27, 88.93, 124.38, 137.59, 165.61 ppm GC-MS (EI): (m/z)$^+$=41, 69, 108, 135, 163, 221, 250 (M$^+$)

As in Synthesis Example 1, the structure of olefins resulting from elimination reaction was analyzed, identifying the following structures (mole percent in parenthesis).

(64.2%)   (23.3%)   (12.5%)

Synthesis Example 3

Synthesis of 1-(1-methylspiro[4.4]nonyl methacrylate (Monomer 3)

Monomer 3

With stirring under nitrogen atmosphere at 40° C., 1300 ml of toluene was added dropwise to a tetrahydrofuran solution of 1.6 mol methylmagnesium chloride (which had been prepared from 39 g of metallic magnesium, 1300 ml of tetrahydrofuran and chloromethane) and then a mixture of 111 g of spiro[4.4]nonan-1-one (which had been synthesized from cyclopentanone by a method as described in A. P. Krapcho, Synthesis, 1974, p 383 and references cited therein) and 1300 ml of toluene added. The reaction mixture was stirred for 1.5 hours at 70° C. and returned to room temperature, after which 20% hydrochloric acid was added to stop the reaction. Through ordinary work-up of extraction, washing and drying, and subsequent vacuum distillation, there was obtained 103 g (yield 83%) of the target compound, 1-methylspiro[4.4]nonan-1-ol.

1-methylspiro[4.4]nonan-1-ol colorless liquid boiling point: 57° C./180 Pa

IR (film): ν=3446, 2954, 2869, 1452, 1375, 1306, 1232, 1206, 1122, 1072, 1054, 1002, 969, 947, 934, 906, 853 cm$^{-1}$ $^1$H-NMR (600 MHz in DMSO-$d_6$):

δ=1.05 (3H, s), 1.10-1.23 (2H, m), 1.35-1.75 (12H, m), 3.94 (1H, OH, s) ppm $^{13}$C-NMR (150 MHz in DMSO-$d_6$):

δ=18.68, 22.94, 24.62, 24.96, 31.75, 34.02, 37.18, 39.09, 56.03, 79.47 ppm

With stirring under nitrogen atmosphere at 40° C., a mixture of 88 g of methacryloyl chloride and 200 ml of acetonitrile was added dropwise to a mixture of 88 g of 1-methylspiro[4.4]nonan-1-ol, 114 g of triethylamine, 6.9 g of 4-dimethylaminopyridine, and 300 ml of acetonitrile. The reaction mixture was stirred overnight at 50° C. and returned to room temperature, after which a saturated sodium hydrogencarbonate aqueous solution was added to stop the reaction. Through ordinary work-up of extraction, washing and drying, and subsequent vacuum distillation, there was obtained 105 g (yield 84%) of the target compound, 1-(1-methylspiro[4.4]nonyl)methacrylate.

1-(1-methylspiro[4.4]nonyl)methacrylate colorless liquid boiling point: 61° C./20 Pa IR (film): ν=2955, 2872, 1713, 1637, 1469, 1448, 1400, 1331, 1304, 1268, 1169, 1144, 1117, 1076, 1051, 1007, 934, 901, 870, 814 cm$^{-1}$ $^1$H-NMR (600 MHz in DMSO-d$_6$):

δ=1.23-1.28 (1H, m), 1.35-1.40 (1H, m), 1.40 (3H, s), 1.48-1.66 (9H, m), 1.76-1.82 (1H, m), 1.82 (3H, br, s), 1.86-1.92 (1H, m), 2.22-2.29 (1H, m), 5.56 (1H, app quint, J=1.5 Hz), 5.91 (1H, q, J=0.9 Hz) ppm $^{13}$C-NMR (150 MHz in DMSO-d$_6$):

δ=18.05, 18.09, 18.58, 24.57, 24.69, 32.19, 33.31, 34.41, 36.15, 57.02, 91.51, 124.51, 137.48, 165.71 ppm GC-MS (EI): (m/z)$^+$=41, 69, 95, 135, 153, 222 (M$^+$)

As in Synthesis Example 1, the structure of olefins resulting from elimination reaction was analyzed, identifying the following structures (mole percent in parenthesis).

(44.6%)   (7.5%)   (47.9%)

Synthesis Example 4

Synthesis of 1-(1-ethylspiro[4.4]nonyl)methacrylate (Monomer 4)

Monomer 4

With stirring under nitrogen atmosphere at −10° C. to 0° C., a mixture of 86.4 g of spiro[4.4]nonan-1-one, 102.2 g of ethyl bromide and 560 ml of tetrahydrofuran was added dropwise to a mixture of 13.01 g of metallic lithium and 340 ml of tetrahydrofuran, during which time the temperature was kept below 0° C. The reaction mixture was stirred overnight at room temperature and then ice cooled, after which a saturated ammonium chloride aqueous solution was added to stop the reaction. Through ordinary work-up of extraction, washing and drying, and subsequent purification by silica gel chromatography, there was obtained 53 g of the reactant, spiro[4.4]nonan-1-one and 34.3 g (yield 84% calculated on the basis of the reactant consumed) of the target compound, 1-ethylspiro[4.4]nonan-1-ol.

1-ethylspiro[4.4]nonan-1-ol colorless liquid

IR (film): ν=3484, 2955, 2870, 1462, 1450, 1376, 1311, 1266, 1199, 1128, 1076, 1040, 1028, 1009, 995, 971, 943, 920, 896, 866 cm$^{-1}$ $^1$H-NMR (600 MHz in DMSO-d$_6$):

δ=0.87 (3H, t, J=7.3 Hz), 1.17-1.12 (1H, m), 1.19-1.25 (1H, m), 1.35 (2H, q, J=7.3 Hz), 1.35-1.65 (10H, m), 1.65-1.74 (2H, m), 3.68 (1H, OH, s) ppm $^{13}$C-NMR (150 MHz in DMSO-d$_6$):

δ=8.64, 18.71, 24.45, 25.01, 27.08, 31.96, 33.64, 35.17, 37.64, 56.86, 81.87 ppm GC-MS (EI): (m/z)$^+$=67, 85, 121, 139, 150, 168 (M$^+$)

With stirring under nitrogen atmosphere at 40° C., a mixture of 21 g of methacryloyl chloride and 20 ml of acetonitrile was added dropwise to a mixture of 19.9 g of 1-ethylspiro[4.4]nonan-1-ol, 24 g of triethylamine, 1.44 g of 4-dimethylaminopyridine, and 50 ml of acetonitrile. The mixture was stirred overnight at 50° C. and returned to room temperature, after which a saturated sodium hydrogencarbonate aqueous solution was added to stop the reaction. Through ordinary work-up of extraction, washing and drying, and subsequent vacuum distillation, there was obtained 21.2 g (yield 76%) of the target compound, 1-(1-ethylspiro[4.4]nonyl) methacrylate.

1-(1-ethylspiro[4.4]nonyl)methacrylate colorless liquid boiling point: 68° C./10.6 Pa IR (film): ν=2955, 2873, 1713, 1451, 1328, 1301, 1169, 1116, 935, 814 cm$^{-1}$ $^1$H-NMR (600 MHz in DMSO-d$_6$):

δ=0.82 (3H, t, J=7.3 Hz), 1.21-1.29 (1H, m), 1.32-1.40 (1H, m), 1.49-1.66 (9H, m), 1.76-1.83 (1H, m), 1.84 (3H, br, s), 1.84-1.92 (2H, m), 2.40-2.12 (1H, m), 2.30-2.36 (1H, m), 5.56 (1H, app quint, J=1.5 Hz), 5.93 (1H, app s) ppm $^{13}$C-NMR (150 MHz in DMSO-d$_6$):

δ=8.97, 18.11, 18.75, 23.83, 24.20, 25.13, 33.08, 33.40, 34.66, 37.80, 57.53, 94.65, 124.40, 137.37, 165.59 ppm GC-MS (EI): (m/z)$^+$=41, 69, 95, 121, 149, 167, 179, 207, 236 (M$^+$)

Synthesis Example 5

Synthesis of 1-(1-methylspiro[4.5]decyl methacrylate (Monomer 5)

Monomer 5

With stirring under nitrogen atmosphere at 40° C., 500 ml of toluene was added dropwise to a tetrahydrofuran solution of 0.95 mol methylmagnesium chloride (which had been prepared from 23 g of metallic magnesium, 500 ml of tetrahydrofuran and chloromethane), and then a mixture of 73 g of spiro[4.5]decan-1-one (which had been synthesized from cyclopentanone by a method as described in A. P. Krapcho, Synthesis, 1974, p 383 and references cited therein) and 1300 ml of toluene added. The reaction mixture was stirred overnight at 70° C. and returned to room temperature, after which a saturated ammonium chloride aqueous solution was added to stop the reaction. Through ordinary work-up of extraction, washing and drying, and subsequent vacuum distillation, there was obtained 50.2 g (yield 63%) of the target compound, 1-methylspiro[4.5]decan-1-ol.

1-methylspiro[4.5]decan-1-ol colorless liquid
boiling point: 68° C./146 Pa
IR (D-ATR): ν=3446, 2925, 2853, 1450, 1375, 1235, 1142, 1120, 1089, 1050, 924, 899, 841 cm$^{-1}$
$^1$H-NMR (600 MHz in DMSO-d$_6$):
δ=0.97-1.63 (19H, m), 3.82 (1H, OH, s) ppm
$^{13}$C-NMR (150 MHz in DMSO-d$_6$):
δ=18.70, 22.11, 22.56, 23.07, 26.15, 29.95, 31.14, 31.28, 38.30, 47.20, 80.55 ppm
GC-MS (EI): (m/z)$^+$=43, 71, 94, 108, 121, 135, 153, 168 (M$^+$)

With stirring under nitrogen atmosphere at 40° C., a mixture of 34.5 g of methacryloyl chloride and 50 ml of acetonitrile was added dropwise to a mixture of 37 g of 1-methylspiro[4.5]decan-1-ol, 43.8 g of triethylamine, 2.6 g of 4-dimethylaminopyridine, and 100 ml of acetonitrile. The reaction mixture was stirred overnight at 50° C. and returned to room temperature, after which 5% hydrochloric acid was added to stop the reaction. Through ordinary work-up of extraction, washing and drying, and subsequent vacuum distillation, there was obtained 47.4 g (yield 94%) of the target compound, 1-(1-methylspiro[4.5]decyl)methacrylate.

1-(1-methylspiro[4.5]decyl)methacrylate colorless liquid
boiling point: 68° C./13 Pa
IR (D-ATR): ν=2927, 2856, 1709, 1637, 1449, 1376, 1328, 1303, 1169, 1148, 1135, 932, 812 cm$^{-1}$
$^1$H-NMR (600 MHz in DMSO-d$_6$):
δ=1.02-1.11 (1H, m), 1.16-1.38 (5H, m), 1.38 (3H, s), 1.48-1.63 (7H, m), 1.65-1.72 (1H, m), 1.83 (3H, br, s), 1.84-1.91 (1H, m), 2.30-2.36 (1H, m), 5.56 (1H, app t, J=1.8 Hz), 5.91 (1H, app s) ppm
$^{13}$C-NMR (150 MHz in DMSO-d$_6$):
δ=17.24, 18.19, 18.43, 22.29, 22.73, 25.89, 29.71, 30.07, 30.36, 33.18, 48.84, 92.77, 124.52, 137.66, 165.69 ppm
GC-MS (EI): (m/z)$^+$=41, 69, 107, 149, 167, 236 (M$^+$)

Synthesis Example 6

Synthesis of (1'-ethyl-5-norbornane-2-spiro-1'-cyclopentan-2'-yl methacrylate (Monomer 6)

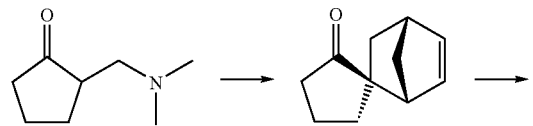

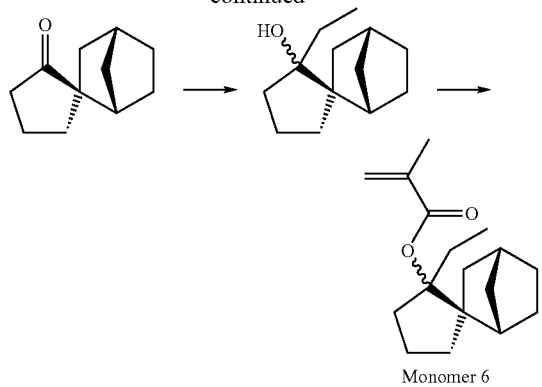

Monomer 6

A mixture of 63 g of 2-dimethylaminocyclopentanone and 40 g of cyclopentadiene was heated under reflux in an oil bath at 110° C. for 12 hours. Upon distillation of the reaction mixture, a fraction having a boiling point of up to 67° C./80 Pa was collected, which was purified by silica gel column chromatography. There were obtained 25.7 g (yield 39%) of the target compound, exo-5-norbornene-2-spiro-1'-cyclopentan-2'-one and a minor amount of the isomer, endo-5-norbornene-2-spiro-1'-cyclopentan-2'-one.

exo-5-norbornene-2-spiro-1'-cyclopentan-2'-one colorless liquid
IR (film): ν=2962, 2872, 1727, 1335, 1159, 933 cm$^{-1}$
$^1$H-NMR (400 MHz in CDCl$_3$):
δ=0.85 (1H, dd, J=2.9, 11.2 Hz), 1.24-1.31 (1H, m), 1.50-1.66 (1H, m), 1.70-1.95 (4H, m), 2.01 (1H, dd, J=3.6, 11.5 Hz), 2.14-2.42 (2H, m), 2.70 (br, s), 2.87 (br, s), 6.12 (1H, dd, J=2.9, 5.9 Hz), 6.26 (1H, dd, J=2.9, 5.4 Hz) ppm endo-5-norbornene-2-spiro-1'-cyclopentan-2'-one colorless liquid
IR (film): ν=2962, 2872, 1731, 1335, 1166, 1012 cm$^{-1}$
$^1$H-NMR (400 MHz in CDCl$_3$):
δ=1.42-2.38 (10H, m), 2.76 (br, s), 2.86 (br, s), 5.85 (1H, dd, J=2.9, 5.4 Hz), 6.24 (1H, dd, J=2.9, 5.4 Hz) ppm A mixture of 25.5 g of exo-5-norbornene-2-spiro-1'-cyclopentan-2'-one, 70 ml of tetrahydrofuran, and a catalytic amount of 5% palladium-on-carbon was hydrogenated at 15 kg/cm$^2$. After the catalyst was filtered off, the reaction mixture was concentrated under reduced pressure, obtaining 25.8 g (quantitative yield) of the target compound, exo-norbornane-2-spiro-1'-cyclopentan-2'-one.

exo-norbornane-2-spiro-1'-cyclopentan-2'-one colorless liquid
IR (film): ν=2951, 2872, 1732, 1317, 1155, 1041 cm$^{-1}$
$^1$H-NMR (400 MHz in CDCl$_3$):
δ=0.91 (1H, dd, J=2.9, 11.7 Hz), 1.05-1.22 (2H, m), 1.32-1.65 (3H, m), 1.67-2.35 (10H, m) ppm With stirring under nitrogen atmosphere at −35° C., a mixture of 26 g of exo-5-norbornane-2-spiro-1'-cyclopentan-2'-one (which had been synthesized by hydrogenation of the Diels-Alder adduct of 2-dimethylaminocyclopentanone with cyclopentadiene, the term "exo" denoting the steric position of ketone relative to norbornane ring) and 32.8 g of ethyl bromide was added dropwise to a mixture of 3.2 g of metallic lithium and 150 ml of tetrahydrofuran, during which time the temperature was kept below 0° C. The reaction mixture was stirred overnight at 5° C. and ice cooled, after which a saturated ammonium chloride aqueous solution was added to stop the reaction. Through ordinary work-up of extraction, washing and drying, and subsequent purification by silica gel chromatography, there was obtained 20.8 g (yield 68%) of the target compound, 1'-ethyl-5-norbornane-2-spiro-1'-cyclopentan-2'-ol.

exo-1'-ethyl-5-norbornan-2-spiro-1'-cyclopentan-2'-ol (diastereomer mixture)

IR (film): ν=3479, 2949, 2870, 1458, 1296, 1130, 1105, 968, 887 cm$^{-1}$
$^1$H-NMR (400 MHz in CDCl$_3$):
δ=0.81-0.90 (1H, m), 0.93-1.00 (3H, m), 1.08-1.21 (3H, m), 1.24-1.43 (2.3H, m), 1.44-1.65 (9.5H, m), 1.64-1.73 (1H, m), 1.80-1.87 (0.3H, m), 1.96-2.06 (1H, m), 2.17-2.22 (1.7H, m) ppm (H count is an approximate relative value provided that the total of integration values of signals of CH, of two isomers appearing at 0.93-1.00 is 3H)

With stirring under nitrogen atmosphere at 5° C., 21 ml of triethylamine was added dropwise to a mixture of 13.8 g of exo-1'-ethyl-5-norbornane-2-spiro-1'-cyclopentan-2'-ol (diastereomer mixture), 13 ml of methacryloyl chloride, a catalytic amount of 4-dimethylaminopyridine, and 120 ml of methylene chloride. The reaction mixture was stirred overnight at room temperature, after which a saturated ammonium chloride aqueous solution was added to stop the reaction. Through ordinary work-up of extraction, washing and drying, and subsequent concentration under reduced pressure, there was obtained the target compound, exo-(1'-ethyl-5-norbornane-2-spiro-1'-cyclopentan-2'-yl)methacrylate.

Synthesis Example 7

Synthesis of 6-methyl-6-dispiro[4.1.4.3]tetradecyl methacrylate (Monomer 7)

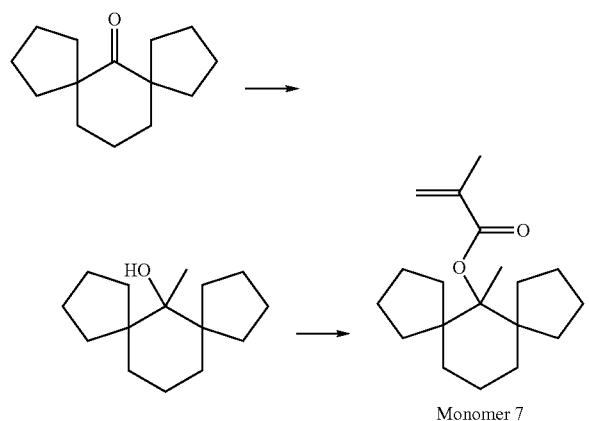

Monomer 7

With stirring under nitrogen atmosphere at 50° C., a mixture of 44.3 g of dispiro[4.1.4.3]tetradecan-6-one (which had been synthesized from spiro[4.5]decan-6-one by a method as described in A. P. Krapcho, Synthesis, 1974, p 383 and references cited therein) and 50 ml of tetrahydrofuran was added dropwise to a tetrahydrofuran solution of 0.43 mol methylmagnesium chloride (which had been prepared from 10.45 g of metallic magnesium, 150 ml of tetrahydrofuran and chloromethane), during which time the temperature was kept below 60° C. The reaction mixture was cooled to room temperature, after which a saturated ammonium chloride aqueous solution was added to stop the reaction. Through ordinary work-up of extraction, washing and drying, and subsequent vacuum distillation, there was obtained 46.3 g (yield 97%) of the target compound, 6-methyldispiro[4.1.4.3]-tetradecan-6-ol.

6-methyldispiro[4.1.4.3]tetradecan-6-ol colorless liquid
boiling point: 86° C./13 Pa
IR (film): ν=3625, 3520, 2948, 2866, 1444, 1377, 1305, 1111, 1090, 944, 902 cm$^{-1}$
$^1$H-NMR (600 MHz in DMSO-d$_6$):
δ=1.06 (3H, s), 1.14-1.23 (6H, m), 1.28-1.55 (12H, m), 1.62-1.73 (2H, br), 1.79-1.86 (2H, m), 3.72 (1H, OH, s) ppm
$^{13}$C-NMR (150 MHz in DMSO-d$_6$):
δ=18.69, 20.09 (CH$_3$, br), 23.41 (2C, br), 24.57 (2C), 30.12 (2C, br), 33.86 (2C), 34.83 (2C, br), 51.40 (2C), 74.68 ppm
GC-MS (EI): (m/z)$^+$=43, 67, 93, 108, 122, 135, 162, 189, 204, 222 (M$^+$)

With stirring under nitrogen atmosphere under ice cooling, 32.8 g of 6-methyldispiro[4.1.4.3]tetradecan-6-ol was added dropwise to a mixture of 57.5 ml of a n-hexane solution of 2.64M n-butyllithium and 60 ml of tetrahydrofuran, during which time the temperature was kept below 20° C. The reaction mixture was stirred for a further 2 hours at 50° C. and ice cooled again, whereupon a mixture of 27 g of mixed methacrylic/pivalic anhydride and 160 ml of tetrahydrofuran was added dropwise. The reaction mixture was stirred overnight at room temperature, after which a saturated sodium hydrogencarbonate aqueous solution was added to stop the reaction. Through ordinary work-up of extraction, washing and drying, and subsequent purification by silica gel column chromatography, there was obtained 18.8 g (yield 44%) of the target compound, 6-methyl-6-dispiro-[4.1.4.3]tetradecyl methacrylate.

6-methyl-6-dispiro[4.1.4.3]tetradecyl methacrylate colorless liquid
IR (D-ATR): ν=2939, 2866, 1709, 1637, 1455, 1385, 1320, 1297, 1170, 1145, 1124, 931, 807 cm$^{-1}$
$^1$H-NMR (600 MHz in DMSO-d$_6$):
δ=1.21-1.28 (2H, m), 1.30-1.60 (16H, m), 1.60-1.68 (2H, m), 1.66 (3H, s), 1.85 (3H, br, s), 1.90-1.97 (2H, m), 5.55 (1H, app quint, J=1.2 Hz), 5.91 (1H, app s) ppm
$^{13}$C-NMR (150 MHz in DMSO-d$_6$, 60° C.):
δ=16.52 (CH$_3$, br), 18.10, 18.22, 23.92 (4C, br), 33.78 (2C), 33.83 (2C, br), 34.19 (2C, br), 52.38 (2C), 93.01, 123.59, 138.05, 165.47 ppm In the $^{13}$C-NMR spectrum, since missing carbon due to peak broadening was observed upon measurement at room temperature, measurement was made at an elevated temperature of 60° C. Even at the elevated temperature, a signal broadening was observed which is believed to occur because equilibration between conformations is restrained by steric hindrance.

To the NMR measurement sample was added a catalytic amount of trifluoromethanesulfonic acid. The sample was heated at 40° C. to facilitate elimination reaction. The structure of olefins resulting from elimination reaction was analyzed by $^1$H and $^{13}$C-NMR spectroscopy, identifying the following structures (mole percent in parenthesis). Formation of a decalin-form olefin resulting from skeletal rearrangement due to 1,2-alkyl shift was observed.

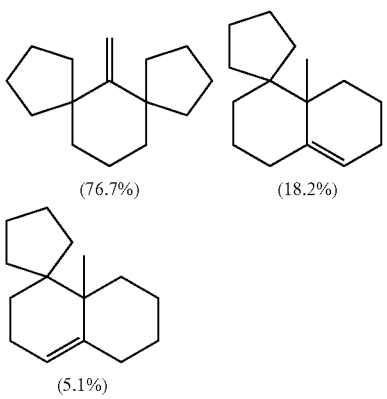

(76.7%)   (18.2%)

(5.1%)

Synthesis Example 8

Synthesis of 6-dispiro[4.1.4.3]tetradecyl methacrylate (Monomer 8)

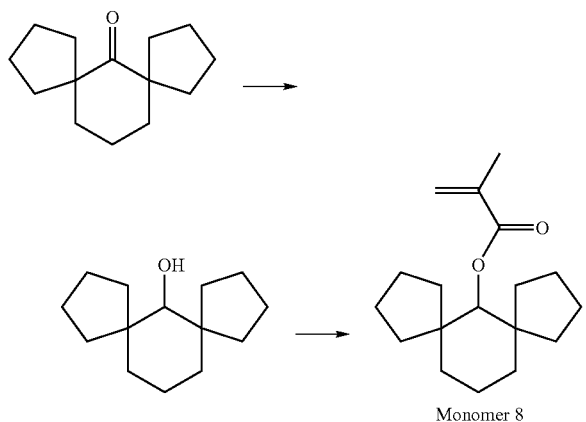

Monomer 8

With stirring under nitrogen atmosphere under ice cooling, 80 g of dispiro[4.1.4.3]tetradecan-6-one and 73 g of tetrahydrofuran were added to a mixture of 14.5 g of sodium borohydride, 145 g of methanol, 0.3 g of 25% sodium hydroxide aqueous solution, 8 g of water, and 73 g of tetrahydrofuran. The reaction mixture was stirred overnight at room temperature, and 300 ml of toluene was added thereto, whereupon the organic layer was separated. Through ordinary work-up of extraction, washing and drying, and subsequent concentration under reduced pressure, there was obtained 81.0 g (yield 99%) of the target compound, dispiro[4.1.4.3]-tetradecan-6-ol. This compound had a purity high enough to use in the subsequent step without further purification.

dispiro[4.1.4.3]tetradecan-6-ol colorless solid
IR (D-ATR): ν=3481, 2926, 2861, 1449, 1060 cm$^{-1}$
$^1$H-NMR (600 MHz in DMSO-d$_6$):
δ=0.99-1.07 (2H, m), 1.08-1.21 (4H, m), 1.25-1.35 (2H, m), 1.38-1.57 (10H, m), 1.57-1.63 (2H, m), 1.70-1.79 (2H, m), 3.11 (1H, d, J=5.9 Hz), 3.39 (1H, OH, d, J=5.9 Hz) ppm
$^{13}$C-NMR (150 MHz in DMSO-d$_6$):
δ=19.55, 23.96 (2C), 24.93 (2C), 30.19 (2C), 36.14 (2C), 38.06 (2C), 47.98, 77.92 (2C) ppm GC-MS (EI): (m/z)$^+$=41, 55, 67, 79, 94, 108, 121, 147, 190, 208 (M$^+$)

With stirring under nitrogen atmosphere at 40° C., a mixture of 3.72 g of methacryloyl chloride and 5 ml of acetonitrile was added dropwise to a mixture of 5.0 g of dispiro[4.1.4.3] tetradecan-6-ol, 4.80 g of triethylamine, 0.29 g of 4-dimethylaminopyridine, and 25 ml of acetonitrile. The reaction mixture was stirred overnight at 40° C., after which a saturated sodium hydrogencarbonate aqueous solution was added to stop the reaction. Through ordinary work-up of extraction, washing and drying, and subsequent purification by silica gel column chromatography, there was obtained 1.92 g (yield 29%) of the target compound, 6-dispiro[4.1.4.3]-tetradecyl methacrylate.

6-dispiro[4.1.4.3]tetradecyl methacrylate colorless liquid
IR (D-ATR): ν=2948, 2865, 1712, 1452, 1292, 1161, 935, 810 cm$^{-1}$
$^1$H-NMR (600 MHz in DMSO-d$_6$):
δ=1.25-1.55 (22H, m), 1.89 (3H, s), 4.77 (1H, s), 5.66 (1H, app quint, J=1.5 Hz), 6.04 (1H, app s) ppm
$^{13}$C-NMR (150 MHz in DMSO-d$_6$, 60° C.):
δ=17.71, 18.85, 23.39 (2C), 23.55 (2C), 33.12 (2C, br), 34.31 (2C, br), 35.96 (2C, br), 47.10, 81.65 (2C), 124.85, 136.06, 166.18 ppm In the $^{13}$C-NMR spectrum, since missing carbon due to peak broadening was observed upon measurement at room temperature, measurement was made at an elevated temperature of 60° C. Even at the elevated temperature, a signal broadening was observed which is believed to occur because equilibration between conformations is restrained by steric hindrance.

GC-MS (EI): (m/z)$^+$=41, 55, 69, 94, 108, 133, 148, 162, 190, 234, 248, 262, 276 (M$^+$)

Synthesis Example 9

Synthesis of 6-methyl-6-spiro[4.5]decyl acrylate

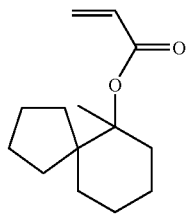 [SMILES: C=CC(=O)OC1(C)CCCCC12CCCC2]

To a mixture of 100 g of 6-methylspiro[4.5]decan-6-ol, 83 g of triethylamine, and 250 g of toluene at 60° C., 69 g of acryloyl chloride in 50 g of toluene was added dropwise over one hour. The mixture was stirred at the temperature for 6 hours, and cooled to 0° C., whereupon 50 g of water and 130 g of saturated sodium bicarbonate water were added dropwise to stop the reaction. Hexane, 300 g, was added to the reaction mixture, which was extracted, washed, dried, concentrated, and distilled for purification, obtaining 105 g (yield 82%) of the target compound, 6-methyl-6-spiro[4.5]decyl acrylate.

6-methyl-6-spiro[4.5]decyl acrylate colorless liquid
boiling point: 69° C./20 Pa IR (D-ATR): ν=2937, 2863, 1718, 1619, 1449, 1401, 1377, 1296, 1283, 1254, 1209, 1165, 1148, 1102, 1047, 1014, 984, 960, 912, 887, 865, 810 cm$^{-1}$ $^1$H-NMR (600 MHz in DMSO-d$_6$):

δ=1.21-1.41 (7H, m), 1.43 (3H, s), 1.46-1.63 (6H, m), 1.78 (1H, br), 1.86-1.92 (1H, m), 2.17 (1H, br), 5.84 (1H, dd, J=1.6, 10.3 Hz), 6.04 (1H, dd, J=10.1, 17.4 Hz), 6.19 (1H, dd, J=1.9, 17.4 Hz) ppm $^{13}$C-NMR (150 MHz in DMSO-d$_6$):

δ=19.36, 21.39, 21.48, 25.67, 25.75, 32.04, 33.15, 34.04, 34.87, 49.94, 129.82, 130.31, 164.51 ppm GC-MS (EI): (m/z)$^+$=27, 43, 55, 67, 81, 93, 108, 121, 135, 149, 165, 179, 193, 207, 222, 283 (M$^+$)

Synthesis Example 10

Synthesis of 6-methyl-6-spiro[4.5]decyl 5-norbornene-2-carboxylate

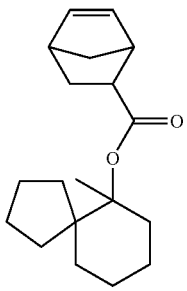 [SMILES: CC1(OC(=O)C2CC3C=CC2C3)CCCCC12CCCC2]

To 50 g of 6-methyl-6-spiro[4.5]decyl acrylate, cyclopentadiene liberated from 20 g of dicyclopentadiene was added dropwise at 30° C. The mixture was slowly heated to 70° C. and stirred for 12 hours at the temperature. The reaction solution was directly purified by silica gel chromatography, obtaining 54 g (yield 98%) of the target compound, 6-methyl-6-spiro[4.5]decyl 5-norbornene-2-carboxylate as a diastereomer mixture.

6-methyl-6-spiro[4.5]decyl 5-norbornene-2-carboxylate as a mixture of two endo-form diastereomers and two exo-form diastereomers (endo: exo form=85:15)

colorless liquid

IR (D-ATR): ν=3061, 2939, 2864, 1725, 1570, 1445, 1376, 1335, 1296, 1271, 1252, 1203, 1165, 1147, 1132, 1103, 1063, 1016, 1000, 954, 922, 904, 887, 866, 838, 815, 778, 759, 711 cm$^{-1}$

Since the product was a mixture of two endo-form diastereomers and two exo-form diastereomers, complex spectra were observed on $^1$H-NMR and $^{13}$C-NMR spectroscopy. Below shown are spectra of the main isomer.

$^1$H-NMR (600 MHz in DMSO-d$_6$):

δ=1.20-1.45 (13H, m), 1.47-1.62 (6H, m), 1.63-1.84 (2H, m), 1.85-1.94 (1H, m), 1.95-2.26 (1H, m), 2.83 (1H, br), 2.90-2.99 (1H, m), 3.08 (1H, br), 5.90 (1H, dd, J=4.6, 10.0 Hz), 6.14-6.18 (1H, m) ppm $^{13}$C-NMR (150 MHz in DMSO-d$_6$):

δ=19.25, 21.35, 21.44, 21.49, 21.55, 25.72, 25.80, 25.83, 28.17, 28.20, 32.02, 32.22, 33.15, 33.36, 33.83, 34.10, 34.88, 34.94, 41.88, 43.84, 43.93, 45.17, 45.30, 49.02, 49.23, 49.89, 49.92, 85.67, 85.76, 132.15, 132.30, 137.49, 137.54, 172.60, 172.66 ppm GC-MS spectrum of the main isomer is also shown.

GC-MS (EI): (m/z)$^+$=27, 43, 66, 81, 95, 121, 135, 150, 166, 190, 205, 223, 245, 259, 273, 288, 313, 326 (M$^+$)

Comparative Synthesis Example 1

Synthesis of 8-methyl-8-spiro[4.5]decyl methacrylate (Monomer 9)

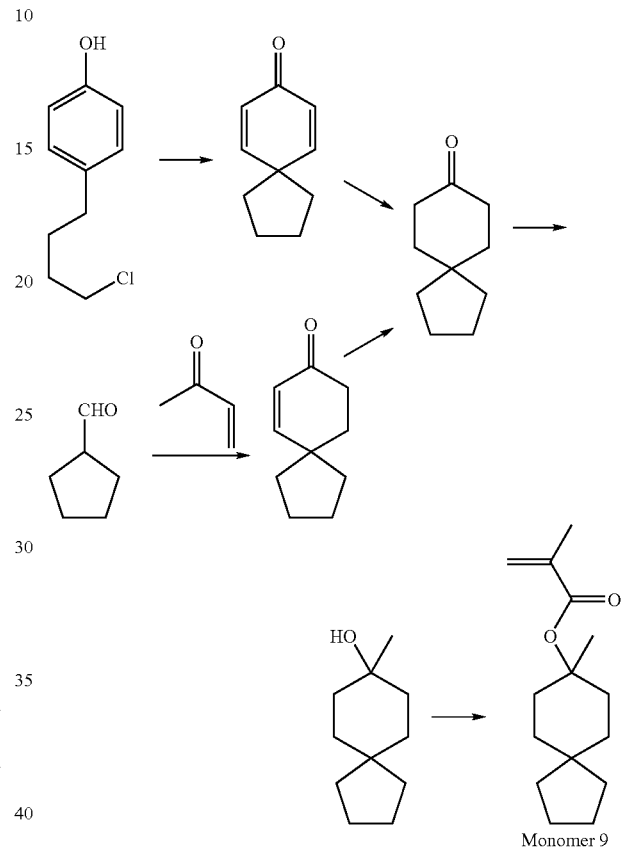

Monomer 9

A 25% sodium hydroxide aqueous solution, 4.8 g, was added to 5.5 g of p-(4-chlorobutyl)phenol and stirred. The mixture was slowly heated under reduced pressure while removing water (until 120° C. at 50 Pa) and subsequently heated to 180-200° C., at which a distillate was collected. There was obtained 2.11 g (yield 47%) of spiro[4.5]deca-6,9-dien-8-one.

spiro[4.5]deca-6,9-dien-8-one colorless liquid

IR (D-ATR): ν=2955, 2868, 1655, 1621, 1406, 1254, 1174, 941, 856 cm$^{-1}$ $^1$H-NMR (600 MHz in DMSO-d$_6$):

δ=1.70-1.75 (4H, m), 1.84-1.90 (4H, m), 6.06-6.11 (2H, m), 7.04-7.08 (2H, m) ppm $^{13}$C-NMR (150 MHz in DMSO-d$_6$):

δ=24.68 (2C), 37.24 (2C), 48.32, 126.40 (2C), 155.72 (2C), 185.17 ppm

GC-MS (EI): (m/z)$^+$=91, 107, 120, 133, 148 (M$^+$)

A mixture of 12.8 g of spiro[4.5]deca-6,9-dien-8-one, 50 ml of ethyl acetate, and a catalytic amount of 10% palladium-on-carbon was hydrogenated at 12 kg/cm$^2$. After the catalyst was filtered off, the reaction mixture was concentrated under reduced pressure, obtaining 13.5 g (quantitative yield) of the target compound, 8-spiro[4.5]decanone. This compound had a purity high enough to use in the subsequent step without further purification.

8-spiro[4.5]decanone colorless liquid

IR (D-ATR): ν=2946, 2856, 1714, 1446, 1336, 1231, 1143, 962 cm$^{-1}$ $^1$H-NMR (600 MHz in DMSO-d$_6$):

δ=1.48-1.56 (4H, m), 1.59-1.64 (4H, m), 1.66 (4H, t, J=6.9 Hz), 2.24 (4H, t, J=6.9 Hz) ppm $^{13}$C-NMR (150 MHz in DMSO-d$_6$, 60° C.):

δ=23.96 (2C), 36.64 (2C), 36.96 (2C), 38.55 (2C), 41.60, 211.22 ppm

GC-MS (EI): (m/z)$^+$=55, 67, 81, 97, 108, 123, 152 (M$^+$)

Synthesis of 8-spiro[4.5]decanone by another route

Piperidine enamine was prepared by a method analogous to that described in Organic Syntheses, Collective Volume 7, p 473, using 221.84 g of cyclopentane carbaldehyde instead of cyclooctane carbaldehyde. Through Michael addition of piperidine enamine to methyl vinyl ketone, cyclization by aldol condensation, dehydration, hydrolysis, and vacuum distillation for purification, there was obtained 173.4 g (yield 54%) of spiro[4.5]dec-6-en-8-one.

spiro[4.5]dec-6-en-8-one colorless liquid

IR (D-ATR): ν=2948, 2861, 1673, 1447, 1388, 1228, 1137, 927, 791 cm$^{-1}$ $^1$H-NMR (600 MHz in DMSO-d$_6$):

δ=1.54-1.73 (8H, m), 1.81 (2H, t, J=6.9 Hz), 2.31-2.35 (3H, m), 5.74 (1H, d, J=9.6 Hz), 6.83 (1H, d, J=10.1 Hz) ppm $^{13}$C-NMR (150 MHz in DMSO-d$_6$):

δ=24.03 (2C), 33.18, 34.98, 37.40 (2C), 43.76, 126.05, 159.64, 198.73 ppm

GC-MS (EI): (m/z)$^+$=53, 66, 79, 94, 108, 122, 150 (M$^+$)

A mixture of 170 g of spiro[4.5]dec-6-en-8-one, 400 ml of tetrahydrofuran, and a catalytic amount of 10% palladium-on-carbon was hydrogenated at 10 kg/cm$^2$. After the catalyst was filtered off, the reaction mixture was concentrated under reduced pressure, obtaining 187 g (quantitative yield) of the target compound, 8-spiro[4.5]decanone. This compound was found to have identical spectroscopic characteristics with the former compound. It had a purity high enough to use in the subsequent step without further purification.

With stirring under nitrogen atmosphere at room temperature, a mixture of 13.4 g of 8-spiro[4.5]decanone and 80 ml of tetrahydrofuran was added dropwise to a tetrahydrofuran solution of 0.205 mol methylmagnesium chloride (which had been prepared from 5.0 g of metallic magnesium, 100 ml of tetrahydrofuran and chloromethane), during which time the temperature was kept below 50° C. The reaction mixture was cooled to room temperature, after which a saturated ammonium chloride aqueous solution was added to stop the reaction. Through ordinary work-up of extraction, washing and drying, and subsequent concentration under reduced pressure, there was obtained 14.43 g (yield 99%) of the target compound, 8-methylspiro[4.5]decan-8-ol. This compound had a purity high enough to use in the subsequent step without further purification.

8-methylspiro[4.5]decan-8-ol colorless solid

IR (D-ATR): ν=3334, 2918, 2853, 1443, 1373, 1268, 1130, 993, 891 cm$^{-1}$ $^1$H-NMR (600 MHz in DMSO-d$_6$):

δ=1.57 (3H, s), 1.13-1.18 (2H, m), 1.28-1.35 (6H, m), 1.36-1.41 (2H, m), 1.47-1.55 (6H, m), 3.94 (1H, OH, s) ppm $^{13}$C-NMR (150 MHz in DMSO-d$_6$, 60° C.):

δ=23.51, 23.88, 29.23 (br), 33.44, 35.60 (2C, r), 36.24, 38.91 (2C, br), 41.33, 67.17 ppm With stirring under nitrogen atmosphere at room temperature, 13.9 g of methacryloyl chloride was added dropwise to a mixture of 14.4 g of 8-methylspiro[4.5]decan-8-ol, 13.5 g of triethylamine, a catalytic amount of 4-dimethylaminopyridine, 150 ml of acetonitrile, and 100 ml of tetrahydrofuran. The mixture was stirred overnight at 50° C. and returned to room temperature, after which water was added to stop the reaction. Through ordinary work-up of extraction, washing and drying, and subsequent vacuum distillation, there was obtained 17.0 g (yield 83%) of the target compound, 8-methyl-8-spiro[4.5]decyl methacrylate.

8-methyl-8-spiro[4.5]decyl methacrylate colorless liquid boiling point: 78° C./9.3 Pa IR (D-ATR): ν=2933, 2854, 1711, 1637, 1445, 1327, 1306, 1176, 1148, 935 cm$^{-1}$ $^1$H-NMR (600 MHz in DMSO-d$_6$):

δ=1.26-1.31 (2H, m), 1.31-1.35 (2H, m), 1.38-1.44 (4H, m), 1.46 (3H, s), 1.47-1.61 (6H, m), 1.84-1.86 (3H, app t, J=0.9 Hz), 2.05-2.10 (2H, m), 5.55-5.57 (1H, m), 5.93-5.95 (1H, m) ppm $^{13}$C-NMR (150 MHz in DMSO-d$_6$, 60° C.):

δ=17.70, 23.39, 23.99, 24.71, 32.85, 33.12, 34.75 (2C), 39.87 (2C), 40.95, 80.80, 123.96, 137.29, 165.42 ppm Comparative Synthesis Example 2

Synthesis of 7-methyl-7-spiro[4.5]decyl methacrylate (Monomer 10)

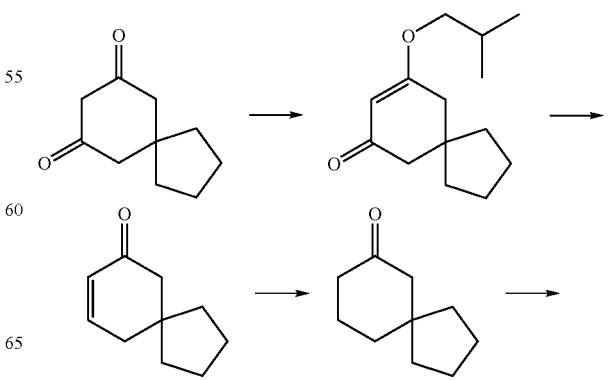

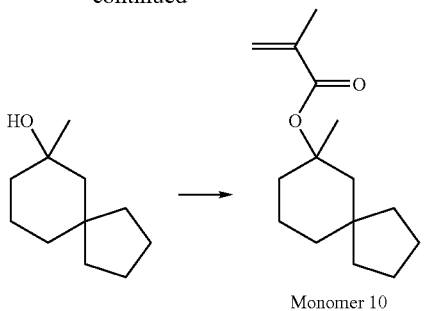

Monomer 10

By following a procedure analogous to that described in Organic Syntheses, Collective Volume 5, p 539, using 81.2 g of spiro[4.5]decane-7,9-dione instead of dihydroresorcinol and isobutyl alcohol instead of ethyl alcohol, a corresponding isobutyl enol ether was prepared. It was purified by silica gel chromatography, obtaining 9-isobutyloxyspiro[4.5]dec-8-en-7-one in a yield of 56%.

9-isobutyloxyspiro[4.5]dec-8-en-7-one colorless liquid
IR (D-ATR): ν=2954, 2873, 1655, 1603, 1471, 1381, 1362, 1213, 1146, 1002, 819 cm$^{-1}$
$^1$H-NMR (600 MHz in DMSO-$d_6$):
δ=0.91 (6H, d, J=6.4 Hz), 1.34-1.47 (4H, m), 1.56-1.63 (4H, m), 1.94 (1H, nonet, J=6.4 Hz), 2.19 (1H, s), 2.36 (1H, s), 3.63 (2H, d, J=6.4 Hz), 5.26 (1H, s, OH) ppm
$^{13}$C-NMR (150 MHz in DMSO-$d_6$):
δ=18.79 (2C), 23.60 (2C), 27.18, 37.48 (2C), 40.67, 42.89, 48.67, 74.13, 101.54, 176.34, 197.82 ppm
GC-MS (EI): (m/z)$^+$=41, 57, 69, 84, 96, 109, 125, 138, 151, 167, 222 (M$^+$)

With stirring under nitrogen atmosphere at room temperature, a mixture of 59 g of 9-isobutyloxyspiro[4.5]dec-8-en-7-one and 150 ml of tetrahydrofuran was added dropwise to a mixture of 10.0 g of lithium aluminum hydride and 400 ml of tetrahydrofuran. The mixture was stirred overnight at room temperature and ice cooled, after which 20 ml of water and then 400 ml of 10% sulfuric acid was added dropwise to stop the reaction. The mixture was stirred for one hour at room temperature, followed by ordinary work-up of extraction, washing and drying, and concentration under reduced pressure. There was obtained 45.9 g of a mixture of 8-spiro[4.5]decen-7-one and 8-spiro[4.5]decen-7-ol. The mixture, 45.8 g, was combined with 50 ml of tetrahydrofuran and a catalytic amount of 10% palladium-on-carbon, and hydrogenated at 14 kg/cm$^2$. After the catalyst was filtered off, the reaction mixture was concentrated under reduced pressure and purified by silica gel chromatography. There were obtained 30.85 g (yield 79%) of 7-spiro[4.5]decanone and 8.92 g (yield 23%) of 7-spiro[4.5]decanol.

7-spiro[4.5]decanone colorless liquid
IR (D-ATR): ν=2940, 2870, 1708, 1444, 1310, 1226, 1174, 1020 cm$^{-1}$
1H-NMR (600 MHz in DMSO-$d_6$):
δ=1.27-1.41 (4H, m), 1.52-1.58 (4H, m), 1.58-1.62 (2H, m), 1.72-1.77 (2H, m), 2.17 (2H, s), 2.21 (2H, t, J=6.4 Hz) ppm $^{13}$C-NMR (150 MHz in DMSO-$d_6$):
δ=23.18, 23.69 (2C), 35.74, 37.54 (2C), 40.52, 46.93, 52.49, 210.62 ppm
GC-MS (EI): (m/z)$^+$=41, 55, 67, 81, 94, 109, 123, 137, 152 (M$^+$)

7-spiro[4.5]decanol colorless solid
IR (D-ATR): ν=3326, 2925, 2856, 1449, 1364, 1091, 1052, 1019 cm$^{-1}$
$^1$H-NMR (600 MHz in DMSO-$d_6$):
δ=0.96-1.10 (3H, m), 1.22-1.38 (6H, m), 1.47-1.61 (6H, m), 1.73-1.79 (1H, m), 3.35-3.33 (1H, m), 4.33 (1H, OH, d, J=4.6 Hz) ppm
$^{13}$C-NMR (150 MHz in DMSO-$d_6$):
δ=21.34, 23.22, 24.41, 34.89, 35.56, 36.57, 41.70, 43.15, 47.31, 66.74 ppm
GC-MS (EI): (m/z)$^+$=41, 55, 67, 79, 94, 107, 121, 138, 154 (M$^+$)

With stirring under nitrogen atmosphere at −70° C., 12.0 g of dimethyl sulfoxide was added to a mixture of 14.4 g of oxalyl chloride and 100 ml of methylene chloride. Stirring was continued for 10 minutes. Below −55° C., a mixture of 8.72 g of 7-spiro[4.5]decanol and 20 ml of methylene chloride was added dropwise thereto, followed by stirring for 30 minutes at −70° C. After 50 g of triethylamine was added, the mixture was warmed up to −5° C. while stirring. The reaction mixture was poured into a saturated ammonium chloride aqueous solution, followed by ordinary work-up of extraction, washing and drying, and purification by silica gel chromatography. There was obtained 8.22 g (yield 96%) of 7-spiro[4.5]decanone. This compound was found to have identical spectroscopic characteristics with the former compound.

With stirring under nitrogen atmosphere at room temperature, a mixture of 39.1 g of 7-spiro[4.5]decanone and 100 ml of tetrahydrofuran was added dropwise to a tetrahydrofuran solution of 0.502 mol methylmagnesium chloride (which had been prepared from 12.2 g of metallic magnesium, 500 ml of tetrahydrofuran and chloromethane). The mixture was stirred overnight at room temperature, after which a saturated ammonium chloride aqueous solution was added to stop the reaction. Through ordinary work-up of extraction, washing and drying, and subsequent concentration under reduced pressure, there was obtained 42.3 g (yield 95%) of the target compound, 7-methylspiro[4.5]decan-7-ol. This compound had a purity high enough to use in the subsequent step without further purification.

7-methylspiro[4.5]decan-7-ol colorless solid
IR (D-ATR): ν=3382, 2926, 2865, 1447, 1371, 1274, 1168, 1126, 962, 922 cm$^{-1}$
$^1$H-NMR (600 MHz in DMSO-$d_6$):
δ=1.02-1.09 (1H, m), 1.05 (3H, s), 1.17-1.65 (15H, m), 3.76 (1H, OH, s) ppm
$^{13}$C-NMR (150 MHz in DMSO-$d_6$):
δ=19.46, 22.94, 24.02, 31.58, 36.50, 36.93, 39.22, 41.32, 42.24, 49.77, 68.55 ppm With stirring under nitrogen atmosphere at 50° C., 41.0 ml of methacryloyl chloride was added dropwise to a mixture of 42.0 g of 7-methylspiro[4.5]decan-7-ol, 40.2 g of triethylamine, a catalytic amount of 4-dimethylaminopyridine, 400 ml of acetonitrile, and 50 ml of tetrahydrofuran. The reaction mixture was stirred for one hour at 50° C., overnight at room temperature, and for a further one hour at 50° C., after which it was returned to room temperature. Water was added to stop the reaction. Through ordinary work-up of extraction, washing and drying, and subsequent vacuum distillation, there was obtained 43.7 g (yield 78%) of the target compound, 7-methyl-7-spiro[4.5]decyl methacrylate.

7-methyl-7-spiro[4.5]decyl methacrylate colorless liquid boiling point: 95° C./73 Pa IR (D-ATR): ν=2929, 2866, 1709, 1637, 1447, 1331, 1306, 1174, 1153, 935 cm$^{-1}$ $^1$H-NMR (600 MHz in DMSO-d$_6$):

δ=1.01-1.08 (1H, m), 1.15-1.22 (1H, m), 1.24-1.35 (3H, m), 1.40-1.56 (9H, m), 1.42 (3H, s), 1.83 (3H, d, J=1.4 Hz), 2.06-2.11 (1H, m), 2.16-2.21 (1H, m), 5.58 (1H, app dq, J=0.9, 1.4 Hz), 5.94 (1H, q, J=0.9 Hz) ppm $^{13}$C-NMR (150 MHz in DMSO-d$_6$):

δ=18.15, 18.82, 22.11, 23.97, 26.41, 34.94, 35.16, 37.02, 41.94, 42.02, 45.08, 81.67, 124.62, 137.51, 165.88 ppm Polymers within the scope of the invention were synthesized according to the following formulation.

Synthesis Example 9-1

Synthesis of Polymer 1

In a nitrogen atmosphere, 6.14 g of 6-methyl-6-spiro-[4.5]decyl methacrylate, 5.12 g of 3-hydroxy-1-adamantyl methacrylate, 8.74 g of 4,8-dioxatricyclo[4.2.1.0$^{3,7}$]nonan-5-on-2-yl methacrylate, 0.57 g of 2,2'-azobisisobutyronitrile, and 0.1 g of 2-mercaptoethanol were dissolved in 22.09 g of PGMEA and 18.97 g of γ-butyrolactone. In a nitrogen atmosphere, with stirring, the solution was added dropwise to 6.28 g of PGMEA and 5.39 g of γ-butyrolactone at 80° C. over 4 hours. After the completion of dropwise addition, the polymerization solution was stirred at 80° C. for a further 2 hours, cooled to room temperature, and then added dropwise to 320 g of methanol. The solids precipitated were separated by filtration, washed twice with 120 g of methanol, and vacuum dried at 50° C. for 16 hours. There was obtained a polymer (designated Polymer 1) in white powder solid form in an amount of 17.19 g (yield 86%).

Polymer 1

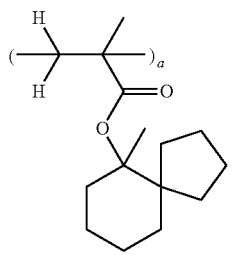
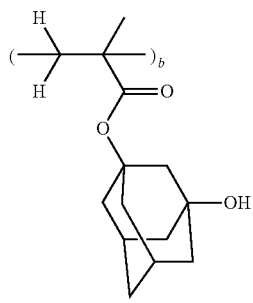
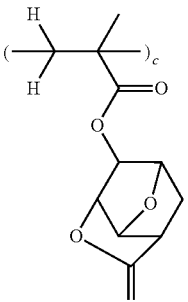

(a = 0.30, b = 0.25, c = 0.45, Mw = 8,090)

Synthesis Examples 9-2 to 9-29 & Comparative Synthesis Examples 3-1 to 3-10

Synthesis of Polymers 2 to 39

Polymers 2 to 39 of the structure and monomer compositional ratio shown below were synthesized by the same procedure as Synthesis Example 9-1 except that the type and proportion of monomers were changed.

Synthesis Example 9-2

Polymer 2

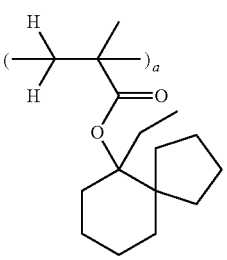
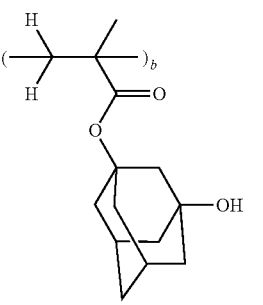
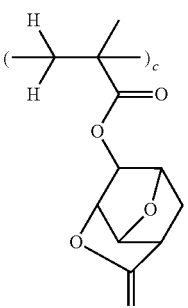

(a = 0.30, b = 0.25, c = 0.45, Mw = 7,950)

Synthesis Example 9-3
Polymer 3
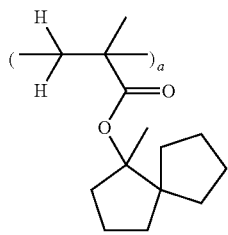 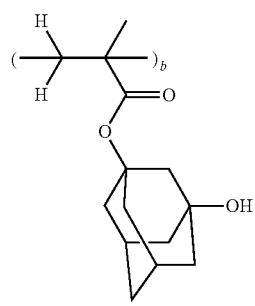
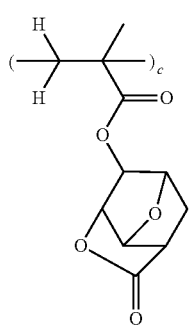
(a = 0.30, b = 0.25, c = 0.45, Mw = 8,100)
Synthesis Example 9-5
Polymer 5
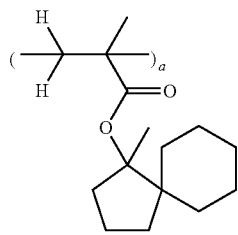 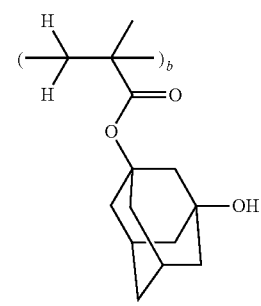
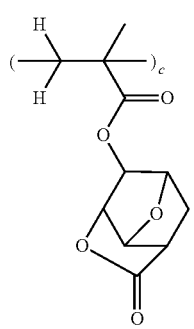
(a = 0.30, b = 0.25, c = 0.45, Mw = 7,300)
Synthesis Example 9-4
Polymer 4
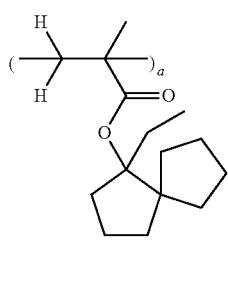 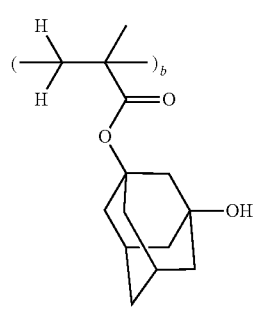
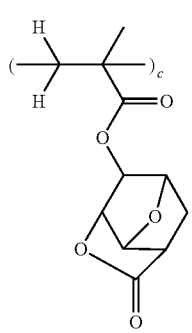
(a = 0.30, b = 0.25, c = 0.45, Mw = 6,920)
Synthesis Example 9-6
Polymer 6
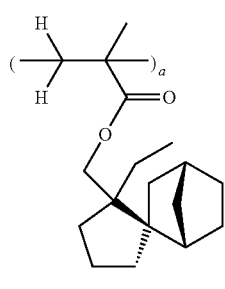 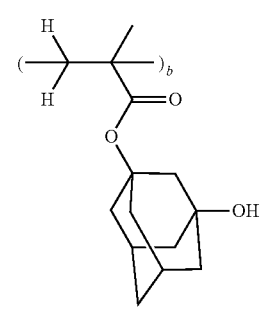
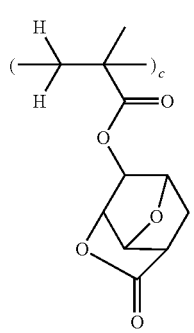
(a = 0.30, b = 0.25, c = 0.45, Mw = 6,570)

Synthesis Example 9-7
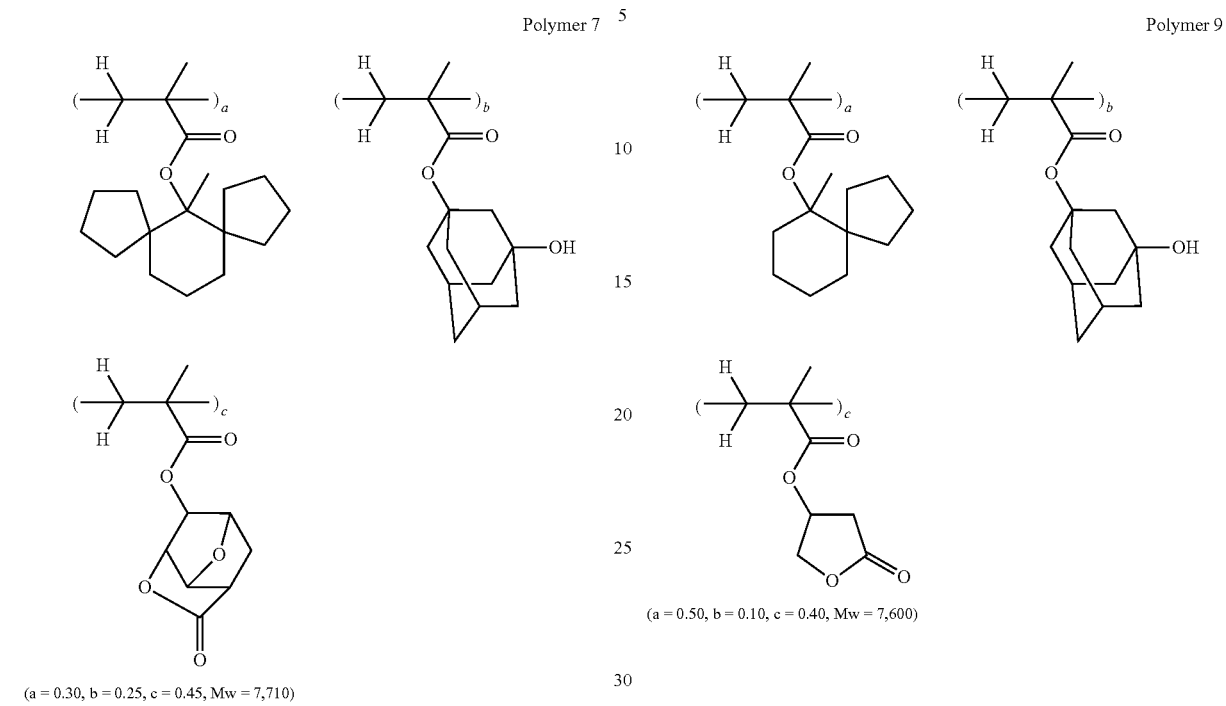
Polymer 7
(a = 0.30, b = 0.25, c = 0.45, Mw = 7,710)
Synthesis Example 9-8
Polymer 8
(a = 0.50, b = 0.10, c = 0.40, Mw = 7,400)
Synthesis Example 9-9
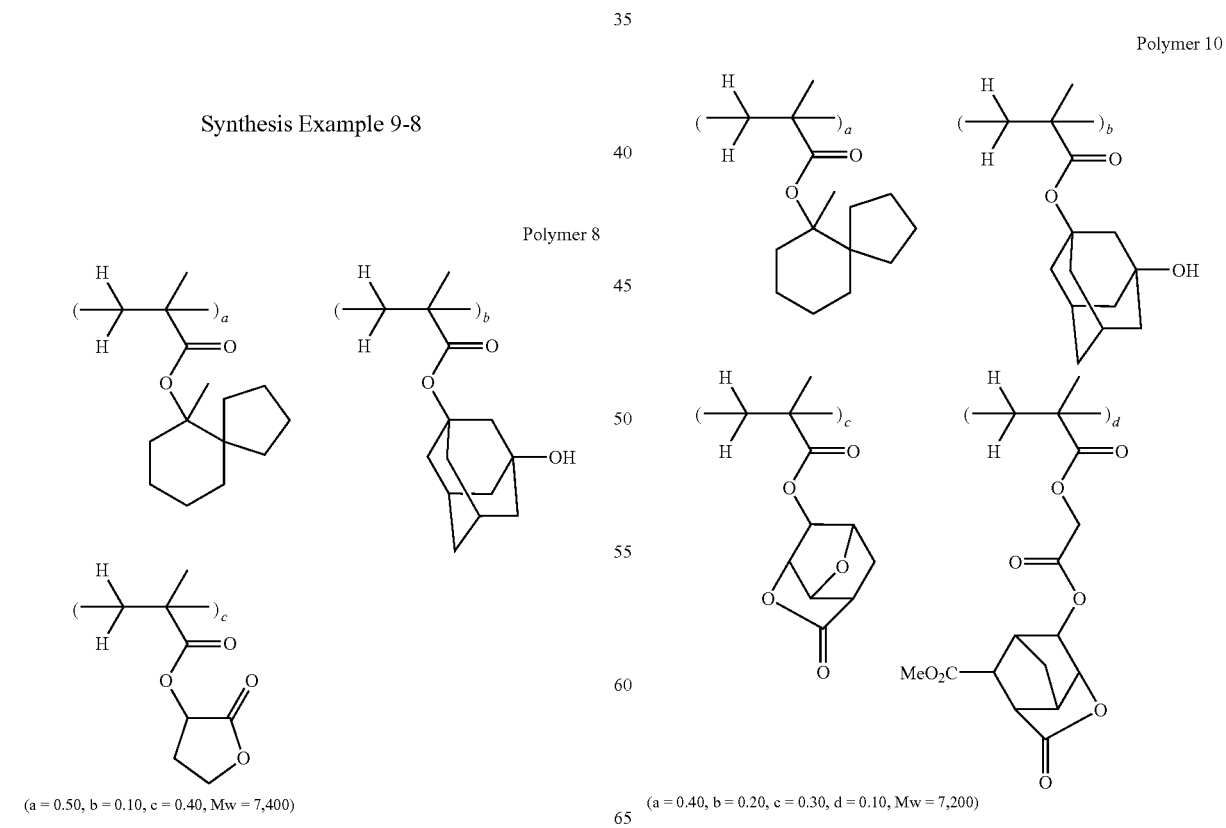
Polymer 9
(a = 0.50, b = 0.10, c = 0.40, Mw = 7,600)
Synthesis Example 9-10
Polymer 10
(a = 0.40, b = 0.20, c = 0.30, d = 0.10, Mw = 7,200)

Synthesis Example 9-11
Polymer 11
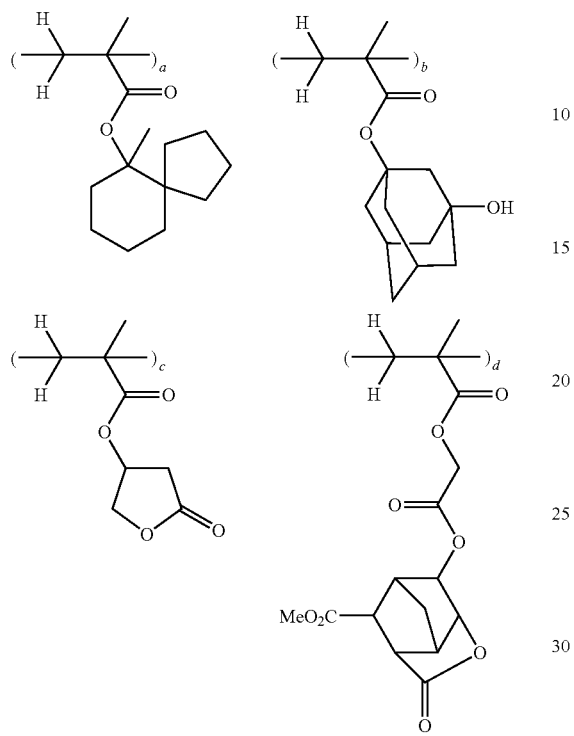
(a = 0.40, b = 0.20, c = 0.30, d = 0.10, Mw = 7,650)
Synthesis Example 9-12
Polymer 12
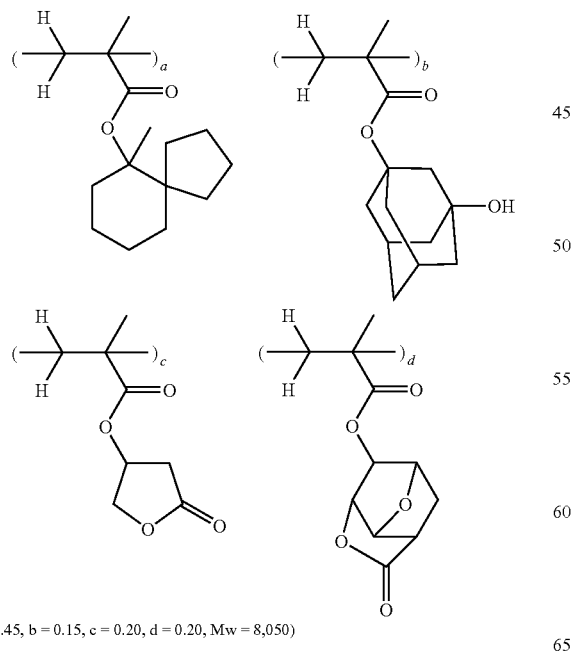
(a = 0.45, b = 0.15, c = 0.20, d = 0.20, Mw = 8,050)
Synthesis Example 9-13
Polymer 13
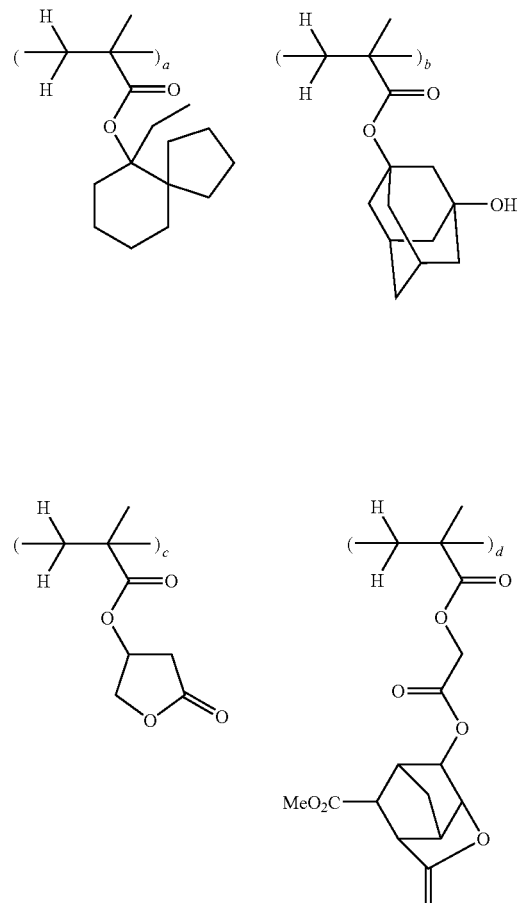
(a = 0.40, b = 0.20, c = 0.30, d = 0.10, Mw = 8,110)
Synthesis Example 9-14
Polymer 14
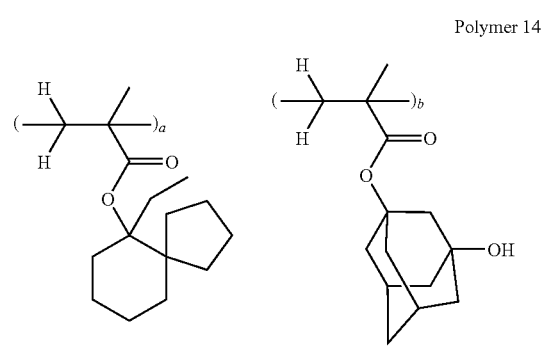

-continued
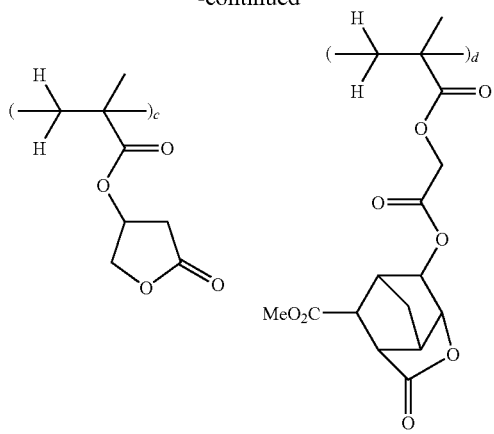
-continued
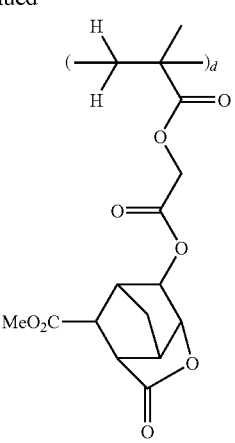
(a = 0.60, b = 0.10, c = 0.25, d = 0.05, Mw = 6,680)
Synthesis Example 9-16
Polymer 16
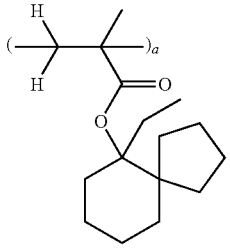
(a = 0.55, b = 0.45, Mw = 8,230)
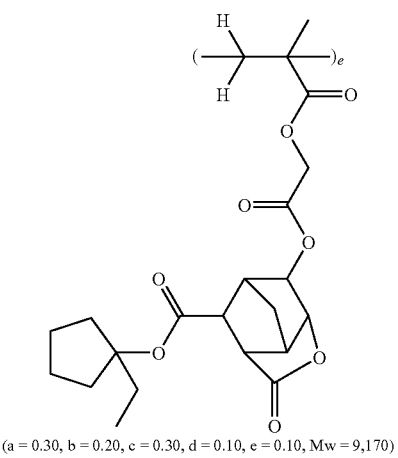
(a = 0.30, b = 0.20, c = 0.30, d = 0.10, e = 0.10, Mw = 9,170)
Synthesis Example 9-15
Polymer 15
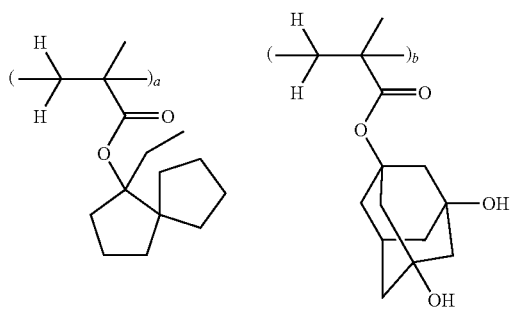
Synthesis Example 9-17
Polymer 17
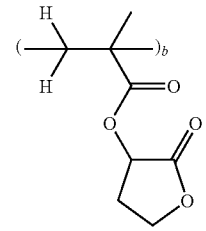
(a = 0.55, b = 0.45, Mw = 8,610)

Synthesis Example 9-18
Polymer 18
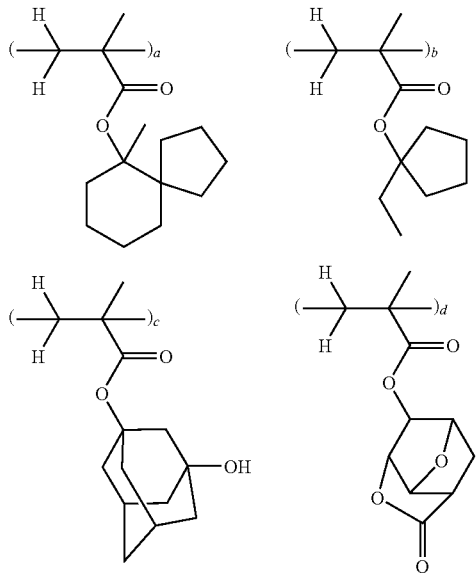
(a = 0.25, b = 0.25, c = 0.10, d = 0.40, Mw = 7,220)
Synthesis Example 9-20
Polymer 20
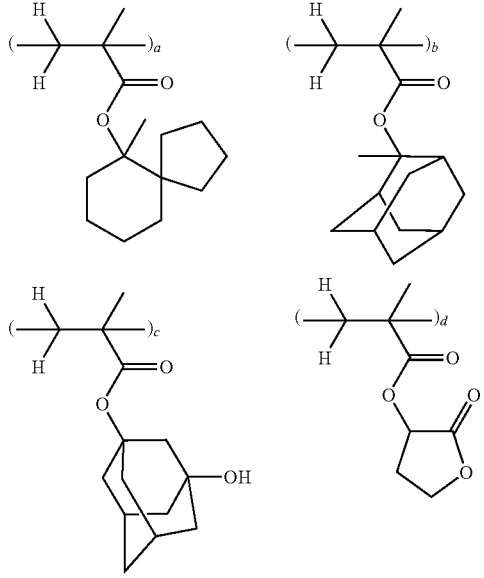
(a = 0.25, b = 0.25, c = 0.10, d = 0.40, Mw = 6,960)
Synthesis Example 9-19
Polymer 19
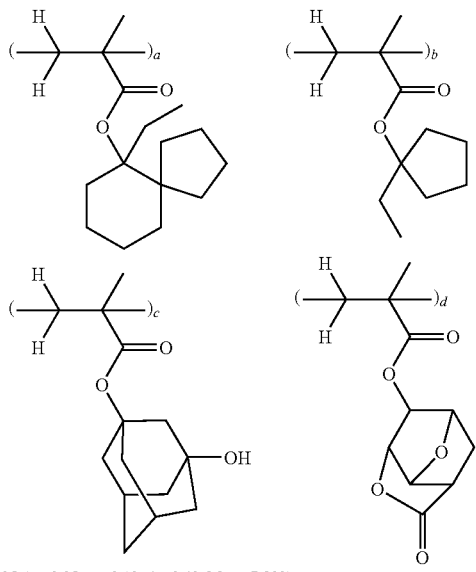
(a = 0.25, b = 0.25, c = 0.10, d = 0.40, Mw = 7,820)
Synthesis Example 9-21
Polymer 21
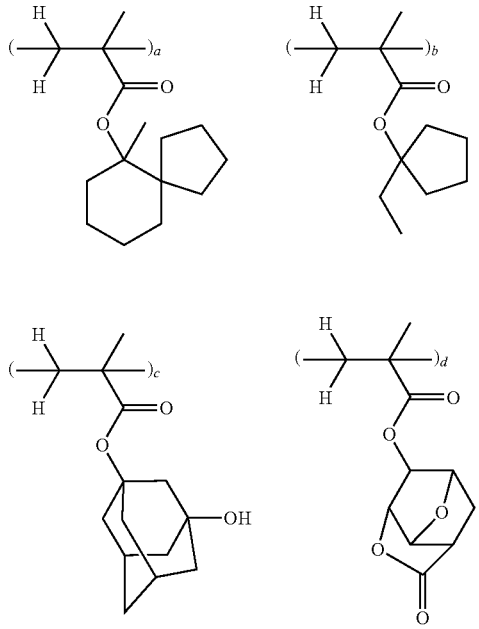

-continued
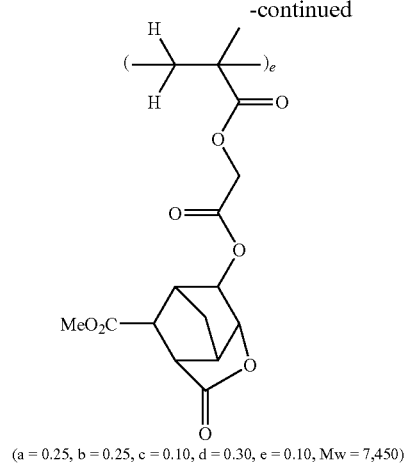
(a = 0.25, b = 0.25, c = 0.10, d = 0.30, e = 0.10, Mw = 7,450)
Synthesis Example 9-22
Polymer 22
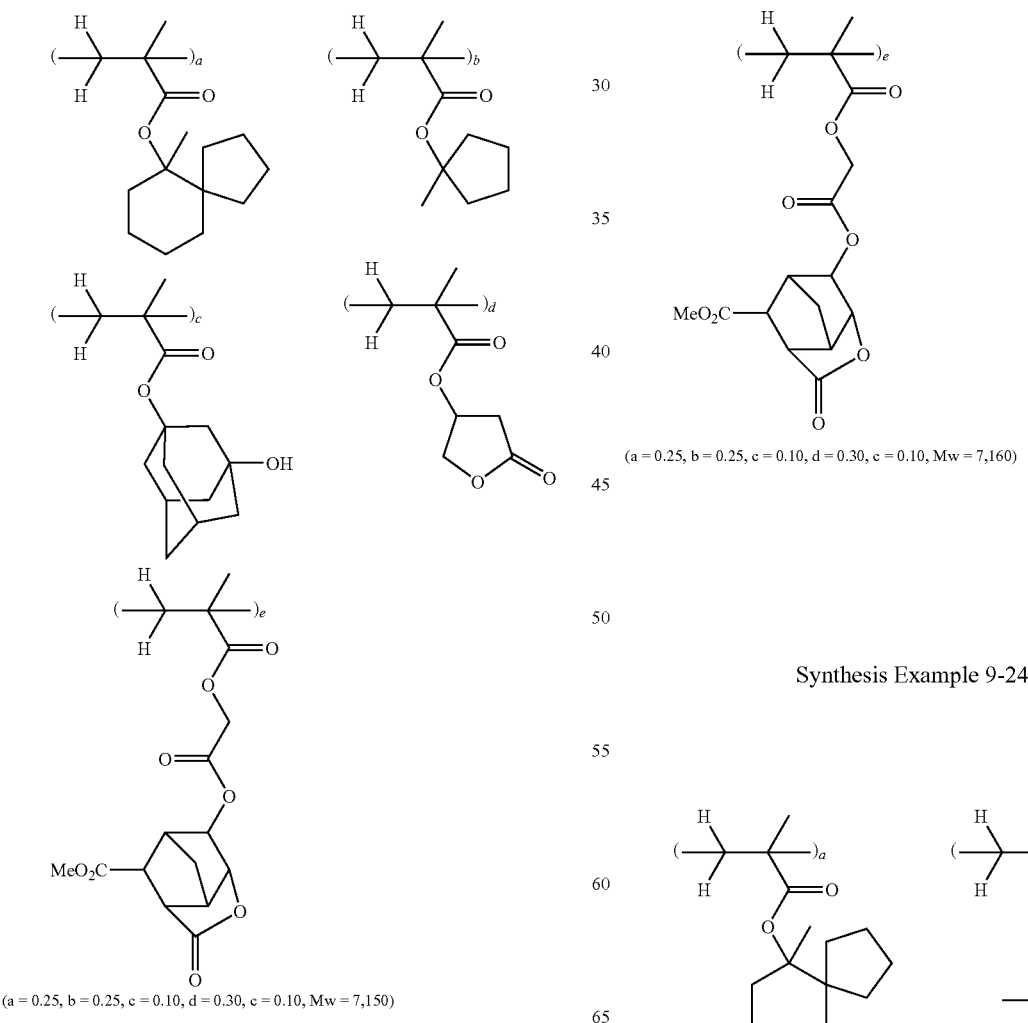
(a = 0.25, b = 0.25, c = 0.10, d = 0.30, e = 0.10, Mw = 7,150)
Synthesis Example 9-23
Polymer 23
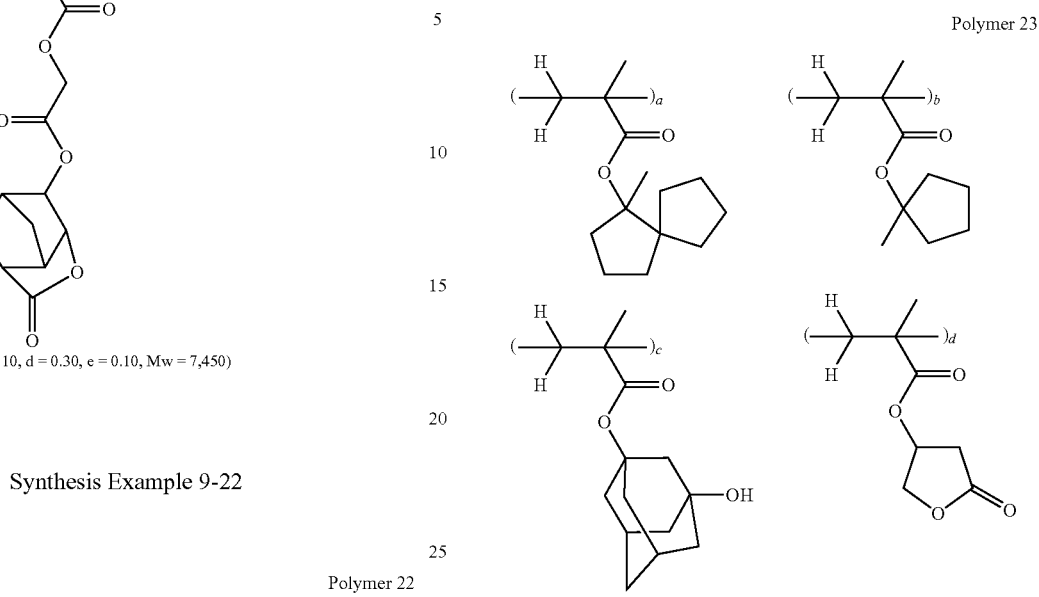
(a = 0.25, b = 0.25, c = 0.10, d = 0.30, e = 0.10, Mw = 7,160)
Synthesis Example 9-24
Polymer 24

-continued
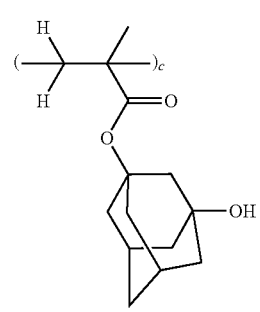 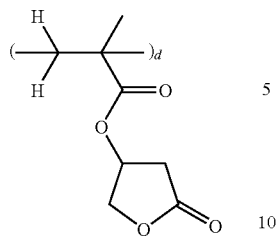
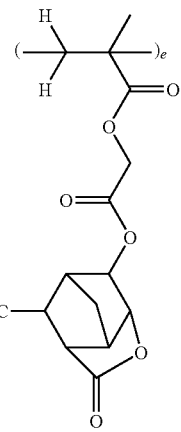
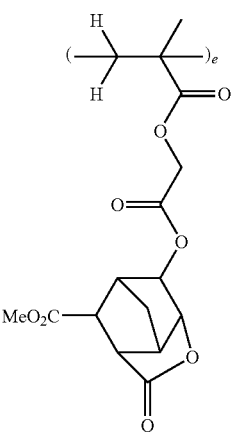
(a = 0.20, b = 0.20, c = 0.20, d = 0.30, e = 0.10, Mw = 8,230)
(a = 0.15, b = 0.15, c = 0.20, d = 0.40, e = 0.10, Mw = 8,800)
Synthesis Example 9-26
Polymer 26
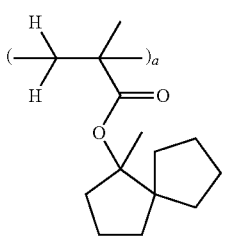 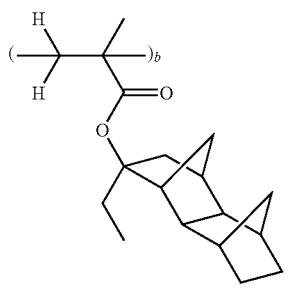
Synthesis Example 9-25
Polymer 25
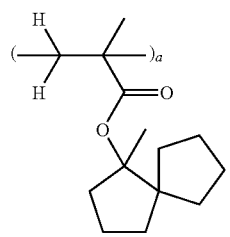 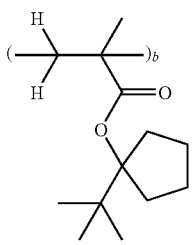
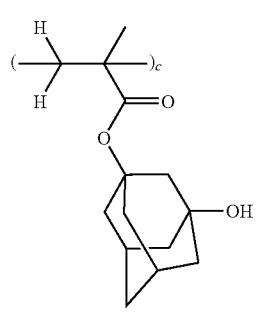 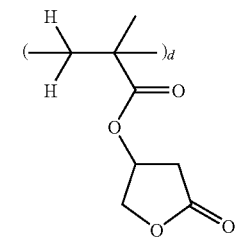
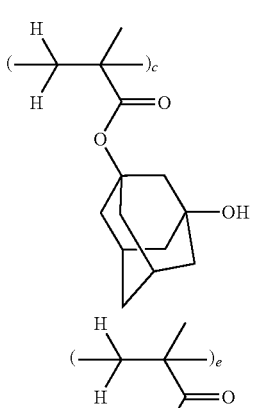
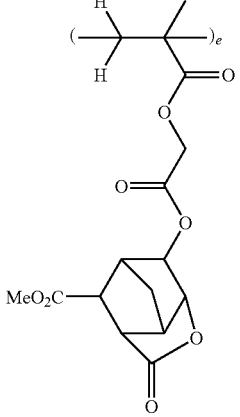

-continued
(a = 0.20, b = 0.20, c = 0.20, d = 0.30, e = 0.10, Mw = 8,700)
Synthesis Example 9-27
Polymer 27
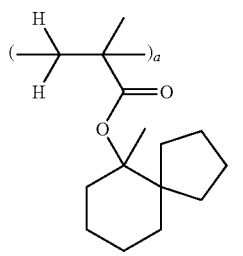 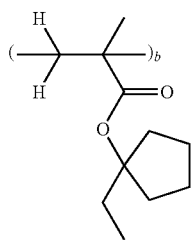
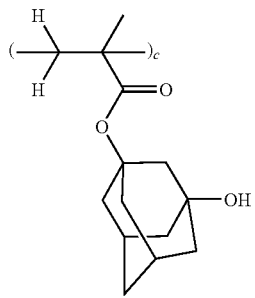 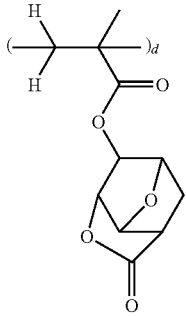
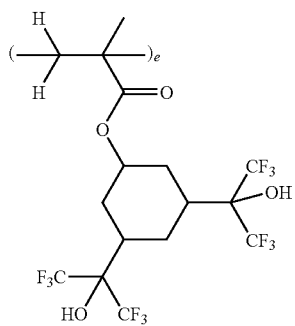
(a = 0.25, b = 0.15, c = 0.20, d = 0.30, e = 0.10, Mw = 5,440)
Synthesis Example 9-28
Polymer 28
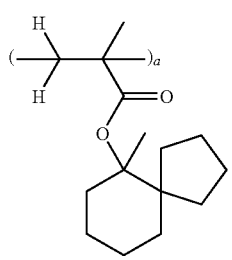 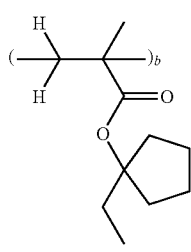
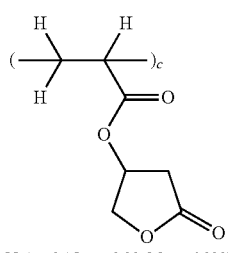
-continued
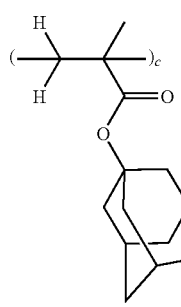 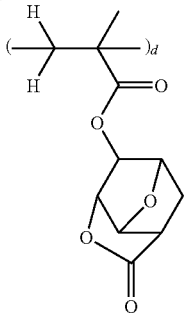
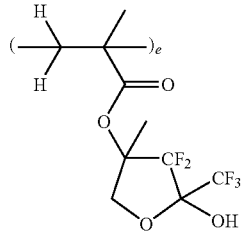
(a = 0.25, b = 0.15, c = 0.20, d = 0.30, e = 0.10, Mw = 5,930)
Synthesis Example 9-29
Polymer 29
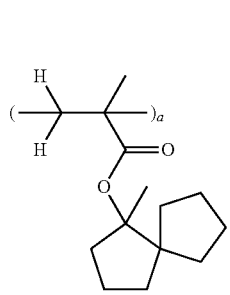 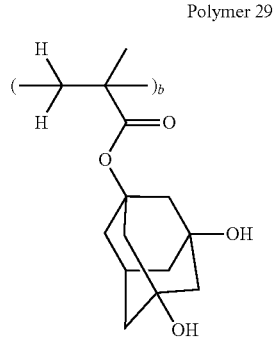
(a = 0.55, b = 0.15, c = 0.30, Mw = 6,320)

Comparative Synthesis Example 3-1
Polymer 30
Comparative Synthesis Example 3-3
Polymer 32
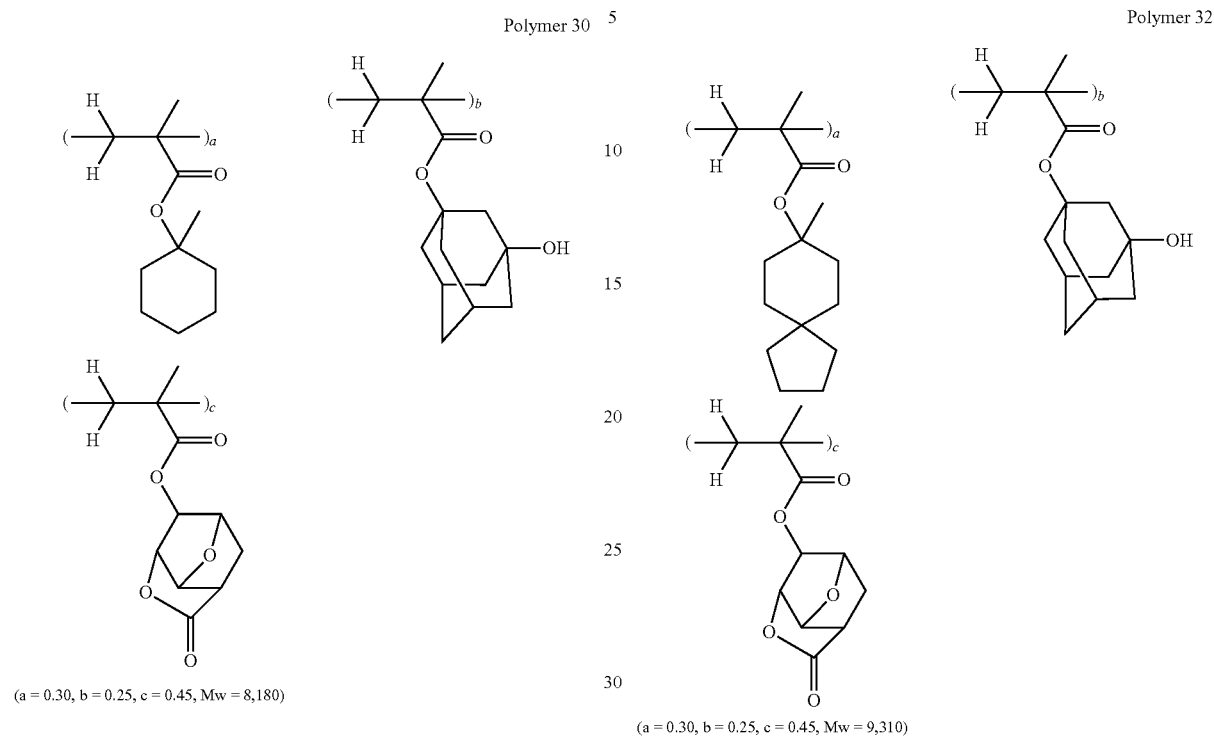
(a = 0.30, b = 0.25, c = 0.45, Mw = 8,180)
(a = 0.30, b = 0.25, c = 0.45, Mw = 9,310)
Comparative Synthesis Example 3-2
Polymer 31
Comparative Synthesis Example 3-4
Polymer 33
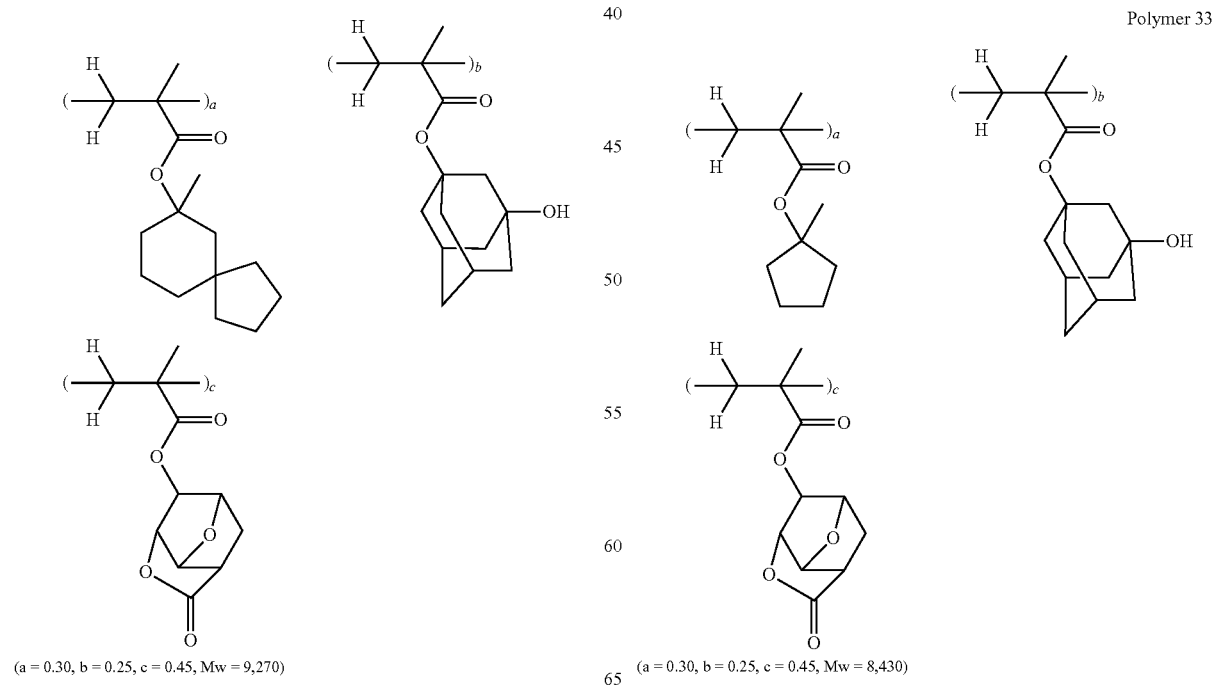
(a = 0.30, b = 0.25, c = 0.45, Mw = 9,270)
(a = 0.30, b = 0.25, c = 0.45, Mw = 8,430)

Comparative Synthesis Example 3-5
Polymer 34
Comparative Synthesis Example 3-7
Polymer 36
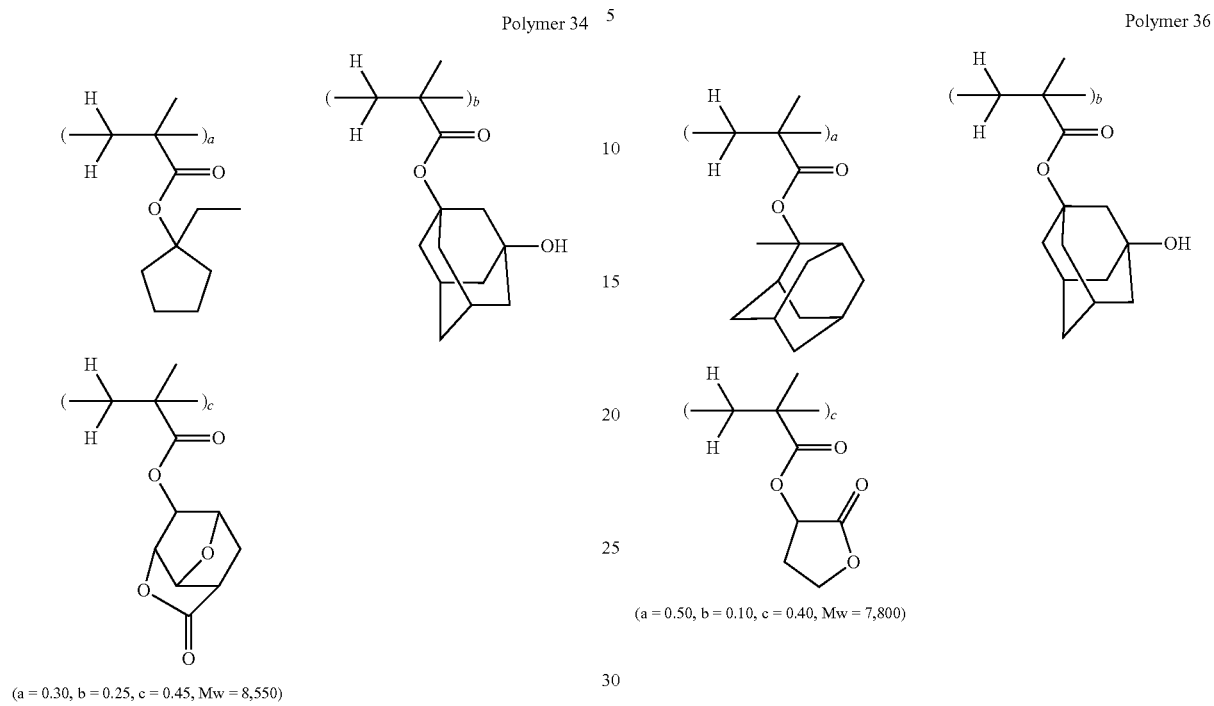
(a = 0.50, b = 0.10, c = 0.40, Mw = 7,800)
Comparative Synthesis Example 3-6
Polymer 35
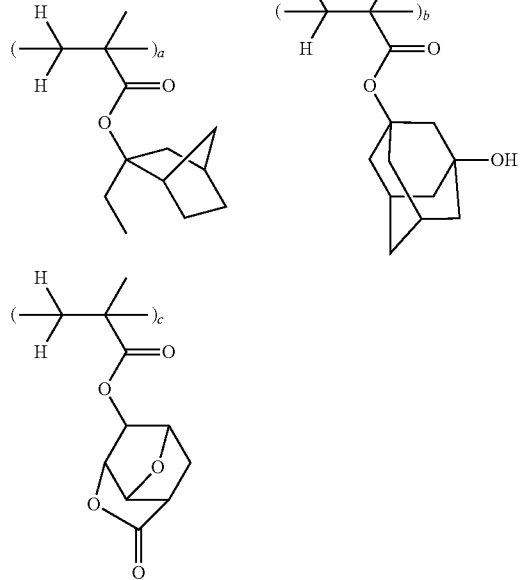
(a = 0.30, b = 0.25, c = 0.45, Mw = 8,030)
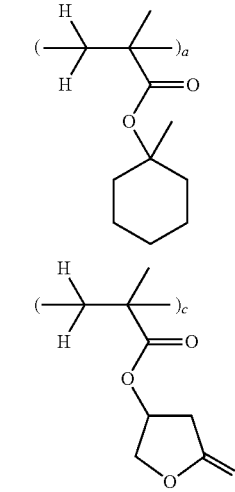
Comparative Synthesis Example 3-8
Polymer 37
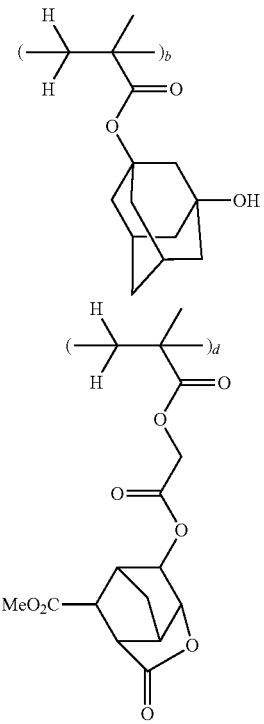
(a = 0.40, b = 0.20, c = 0.30, d = 0.10, Mw = 7,250)

Comparative Synthesis Example 3-9

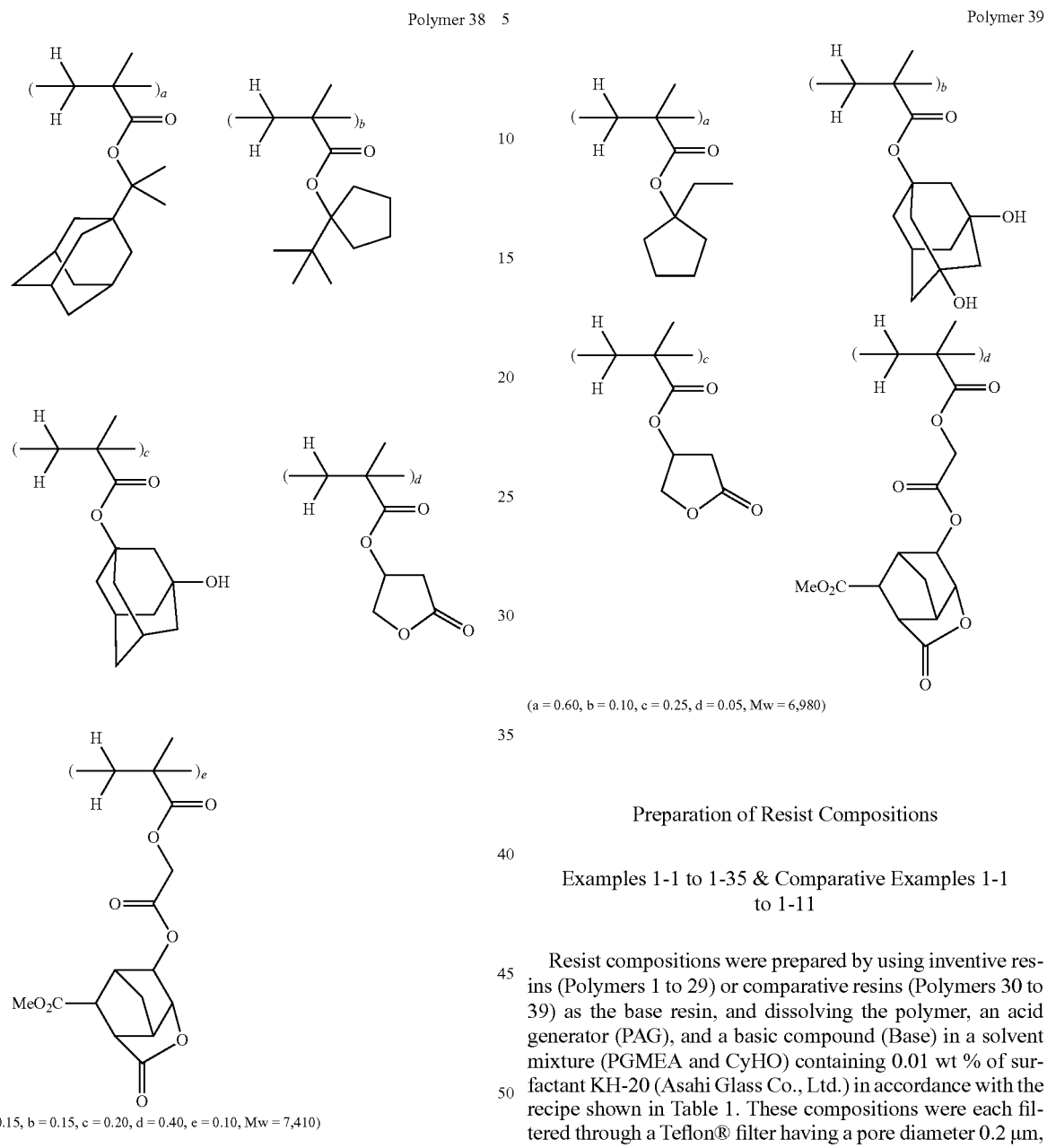

Polymer 38

(a = 0.15, b = 0.15, c = 0.20, d = 0.40, e = 0.10, Mw = 7,410)

Comparative Synthesis Example 3-10

Polymer 39

(a = 0.60, b = 0.10, c = 0.25, d = 0.05, Mw = 6,980)

Preparation of Resist Compositions

Examples 1-1 to 1-35 & Comparative Examples 1-1 to 1-11

Resist compositions were prepared by using inventive resins (Polymers 1 to 29) or comparative resins (Polymers 30 to 39) as the base resin, and dissolving the polymer, an acid generator (PAG), and a basic compound (Base) in a solvent mixture (PGMEA and CyHO) containing 0.01 wt % of surfactant KH-20 (Asahi Glass Co., Ltd.) in accordance with the recipe shown in Table 1. These compositions were each filtered through a Teflon® filter having a pore diameter 0.2 μm, thereby giving inventive resist solutions (R-01 to 35) and comparative resist solutions (R-36 to 46).

TABLE 1

|  |  | Resist | Resin (pbw) | PAG (pbw) | Base (pbw) | Solvent 1 (pbw) | Solvent 2 (pbw) |
|---|---|---|---|---|---|---|---|
| Example | 1-1 | R-01 | Polymer 1 (80) | PAG-1 (8.7) | Base-1 (1.29) | PGMEA (1,120) | CyHO (480) |
|  | 1-2 | R-02 | Polymer 1 (80) | PAG-2 (10.2) | Base-1 (1.29) | PGMEA (1,120) | CyHO (480) |
|  | 1-3 | R-03 | Polymer 1 (80) | PAG-3 (11.0) | Base-1 (1.29) | PGMEA (1,120) | CyHO (480) |
|  | 1-4 | R-04 | Polymer 1 (80) | PAG-4 (11.2) | Base-1 (1.29) | PGMEA (1,120) | CyHO (480) |
|  | 1-5 | R-05 | Polymer 1 (80) | PAG-5 (9.3) | Base-1 (1.29) | PGMEA (1,120) | CyHO (480) |
|  | 1-6 | R-06 | Polymer 1 (80) | PAG-6 (13.6) | Base-1 (1.29) | PGMEA (1,120) | CyHO (480) |
|  | 1-7 | R-07 | Polymer 2 (80) | PAG-2 (10.2) | Base-1 (1.29) | PGMEA (1,120) | CyHO (480) |
|  | 1-8 | R-08 | Polymer 3 (80) | PAG-2 (10.2) | Base-1 (1.29) | PGMEA (1,120) | CyHO (480) |
|  | 1-9 | R-09 | Polymer 4 (80) | PAG-2 (10.2) | Base-1 (1.29) | PGMEA (1,120) | CyHO (480) |

TABLE 1-continued

|  | Resist | Resin (pbw) | PAG (pbw) | Base (pbw) | Solvent 1 (pbw) | Solvent 2 (pbw) |
|---|---|---|---|---|---|---|
| 1-10 | R-10 | Polymer 5 (80) | PAG-2 (10.2) | Base-1 (1.29) | PGMEA (1,120) | CyHO (480) |
| 1-11 | R-11 | Polymer 6 (80) | PAG-2 (10.2) | Base-1 (1.29) | PGMEA (1,120) | CyHO (480) |
| 1-12 | R-12 | Polymer 7 (80) | PAG-2 (10.2) | Base-1 (1.29) | PGMEA (1,120) | CyHO (480) |
| 1-13 | R-13 | Polymer 8 (80) | PAG-2 (10.2) | Base-1 (1.29) | PGMEA (1,120) | CyHO (480) |
| 1-14 | R-14 | Polymer 9 (80) | PAG-2 (10.2) | Base-1 (1.29) | PGMEA (1,120) | CyHO (480) |
| 1-15 | R-15 | Polymer 10 (80) | PAG-2 (10.2) | Base-1 (1.29) | PGMEA (1,120) | CyHO (480) |
| 1-16 | R-16 | Polymer 11 (80) | PAG-2 (10.2) | Base-1 (1.29) | PGMEA (1,120) | CyHO (480) |
| 1-17 | R-17 | Polymer 12 (80) | PAG-2 (10.2) | Base-1 (1.29) | PGMEA (1,120) | CyHO (480) |
| 1-18 | R-18 | Polymer 13 (80) | PAG-2 (10.2) | Base-1 (1.29) | PGMEA (1,120) | CyHO (480) |
| 1-19 | R-19 | Polymer 14 (80) | PAG-2 (10.2) | Base-1 (1.29) | PGMEA (1,120) | CyHO (480) |
| 1-20 | R-20 | Polymer 15 (80) | PAG-5 (9.3) | Base-1 (1.29) | PGMEA (1,120) | CyHO (480) |
| 1-21 | R-21 | Polymer 16 (80) | PAG-2 (10.2) | Base-1 (1.29) | PGMEA (1,120) | CyHO (480) |
| 1-22 | R-22 | Polymer 17 (80) | PAG-2 (10.2) | Base-1 (1.29) | PGMEA (1,120) | CyHO (480) |
| 1-23 | R-23 | Polymer 18 (80) | PAG-4 (11.2) | Base-1 (1.29) | PGMEA (1,120) | CyHO (480) |
| 1-24 | R-24 | Polymer 19 (80) | PAG-2 (10.2) | Base-1 (1.29) | PGMEA (1,120) | CyHO (480) |
| 1-25 | R-25 | Polymer 20 (80) | PAG-2 (10.2) | Base-1 (1.29) | PGMEA (1,120) | CyHO (480) |
| 1-26 | R-26 | Polymer 21 (80) | PAG-2 (10.2) | Base-1 (1.29) | PGMEA (1,120) | CyHO (480) |
| 1-27 | R-27 | Polymer 22 (80) | PAG-2 (10.2) | Base-1 (1.29) | PGMEA (1,120) | CyHO (480) |
| 1-28 | R-28 | Polymer 23 (80) | PAG-2 (10.2) | Base-1 (1.29) | PGMEA (1,120) | CyHO (480) |
| 1-29 | R-29 | Polymer 24 (80) | PAG-2 (7.6) PAG-6 (3.4) | Base-1 (1.29) | PGMEA (1,120) | CyHO (480) |
| 1-30 | R-30 | Polymer 25 (80) | PAG-2 (10.2) | Base-1 (1.29) | PGMEA (1,120) | CyHO (480) |
| 1-31 | R-31 | Polymer 26 (80) | PAG-2 (10.2) | Base-1 (1.29) | PGMEA (1,120) | CyHO (480) |
| 1-32 | R-32 | Polymer 27 (80) | PAG-2 (10.2) | Base-1 (1.29) | PGMEA (1,120) | CyHO (480) |
| 1-33 | R-33 | Polymer 28 (80) | PAG-2 (10.2) | Base-1 (1.29) | PGMEA (1,120) | CyHO (480) |
| 1-34 | R-34 | Polymer 29 (80) | PAG-2 (10.2) | Base-1 (1.29) | PGMEA (1,120) | CyHO (480) |
| 1-35 | R-35 | Polymer 24 (80) Polymer 38 (80) | PAG-2 (10.2) | Base-1 (1.29) | PGMEA (1,120) | CyHO (480) |
| Comparative Example 1-1 | R-36 | Polymer 30 (80) | PAG-1 (8.7) | Base-1 (1.29) | PGMEA (1,120) | CyHO (480) |
| 1-2 | R-37 | Polymer 30 (80) | PAG-2 (10.2) | Base-1 (1.29) | PGMEA (1,120) | CyHO (480) |
| 1-3 | R-38 | Polymer 31 (80) | PAG-2 (10.2) | Base-1 (1.29) | PGMEA (1,120) | CyHO (480) |
| 1-4 | R-39 | Polymer 32 (80) | PAG-2 (10.2) | Base-1 (1.29) | PGMEA (1,120) | CyHO (480) |
| 1-5 | R-40 | Polymer 33 (80) | PAG-2 (10.2) | Base-1 (1.29) | PGMEA (1,120) | CyHO (480) |
| 1-6 | R-41 | Polymer 34 (80) | PAG-2 (10.2) | Base-1 (1.29) | PGMEA (1,120) | CyHO (480) |
| 1-7 | R-42 | Polymer 35 (80) | PAG-2 (10.2) | Base-1 (1.29) | PGMEA (1,120) | CyHO (480) |
| 1-8 | R-43 | Polymer 36 (80) | PAG-2 (10.2) | Base-1 (1.29) | PGMEA (1,120) | CyHO (480) |
| 1-9 | R-44 | Polymer 37 (80) | PAG-2 (10.2) | Base-1 (1.29) | PGMEA (1,120) | CyHO (480) |
| 1-10 | R-45 | Polymer 38 (80) | PAG-2 (10.2) | Base-1 (1.29) | PGMEA (1,120) | CyHO (480) |
| 1-11 | R-46 | Polymer 39 (80) | PAG-2 (10.2) | Base-1 (1.29) | PGMEA (1,120) | CyHO (480) |

PAG-1 to PAG-6 in Table 1 are acid generators of the following structure.

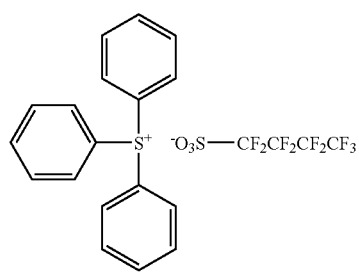

PAG-1

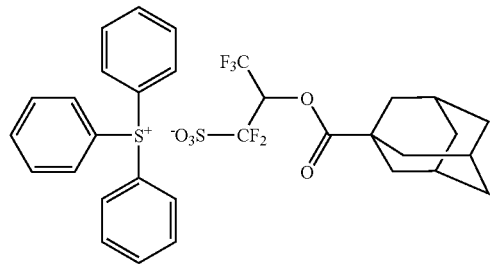

PAG-2

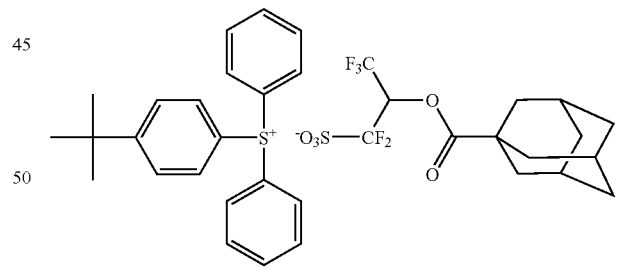

PAG-3

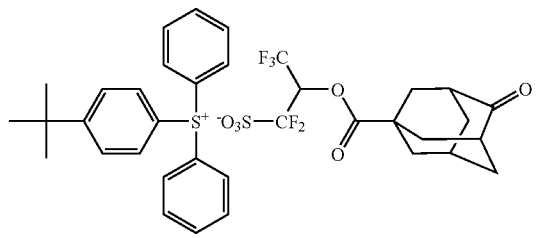

PAG-4

-continued

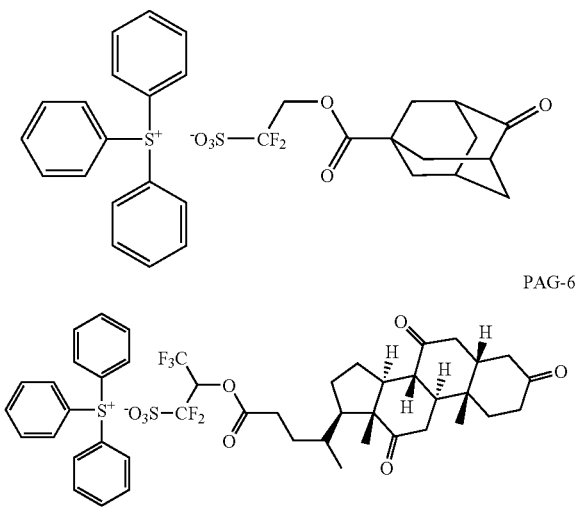

PAG-5

PAG-6

The base and solvent shown in Table 1 have the following meanings.
Base-1: 2-morpholinoethyl octanoate
PGMEA: propylene glycol monomethyl ether acetate
CyHO: cyclohexanone Evaluation of Resist Compositions 1. Comparison of Sensitivity Examples 2-1 to 2-7 & Comparative Examples 2-1 to 2-5

Samples in Table 2 were selected from inventive resist compositions (R-01 to 35) and comparative resist compositions (R-36 to 46) in Example 1. Each resist composition was spin coated on a silicon wafer having an antireflective coating (ARC-29A, Nissan Chemical Co., Ltd.) of 78 nm thick and baked at 120° C. for 60 seconds, forming a resist film of 150 nm thick. The wafer was open-frame exposed by means of an ArF excimer laser stepper (Nikon Corp., NA 0.85), post-exposure baked (PEB) for 60 seconds at 120° C., and puddle developed with a 2.38 wt % TMAH aqueous solution for 30 seconds. The minimum exposure dose ($E_0$) was determined at which the thickness of the resist film became zero at the end of development. A lower value of $E_0$ corresponds to a higher sensitivity, indicating that the resist base resin is more reactive.

The test results are shown in Table 2.

TABLE 2

|  | Resist composition | $E_0$ |
| --- | --- | --- |
| Example 2-1 | R-02 | 10.2 mJ/cm$^2$ |
| Example 2-2 | R-07 | 8.9 mJ/cm$^2$ |
| Example 2-3 | R-08 | 9.2 mJ/cm$^2$ |
| Example 2-4 | R-09 | 8.3 mJ/cm$^2$ |
| Example 2-5 | R-10 | 8.9 mJ/cm$^2$ |
| Example 2-6 | R-11 | 7.8 mJ/cm$^2$ |
| Example 2-7 | R-12 | 8.7 mJ/cm$^2$ |
| Comparative Example 2-1 | R-37 | 12.3 mJ/cm$^2$ |
| Comparative Example 2-2 | R-38 | 11.7 mJ/cm$^2$ |
| Comparative Example 2-3 | R-39 | 11.9 mJ/cm$^2$ |

TABLE 2-continued

|  | Resist composition | $E_0$ |
| --- | --- | --- |
| Comparative Example 2-4 | R-40 | 11.3 mJ/cm$^2$ |
| Comparative Example 2-5 | R-41 | 10.5 mJ/cm$^2$ |

It is estimated from the results in Table 2 that the acid-labile ester monomers of spirocycle structure within the scope of the invention are highly reactive. A comparison of Example 2-1 with Comparative Example 2-1, for example, reveals that the spirocycle bond Monomer 1 possesses greatly contributes to acid-elimination reaction. A comparison of Example 2-1 with Comparative Examples 2-2 and 2-3 reveals that Monomer 1 in which the position of spirocycle bond is adjacent the acid-elimination reaction site is more reactive than Monomers 9 and 10 in which the position of spirocycle bond is separated via one or two carbon atoms apart from the acid-elimination reaction site, indicating that acid-elimination reactivity differs with the position of spirocycle bond. It accounts for a slight difference in reactivity between Comparative Examples 2-2 and 2-3 that Monomer 10 in which the position of spirocycle bond is separated via one carbon atom on the six-membered ring apart from the acid-elimination reaction site provides for a contribution of 1,3-diaxial interaction to acid-elimination reaction. Thus Monomer 10 displays a slightly higher reactivity than Monomer 9.

2. Comparison of Pattern Resolution

Examples 3-1 to 3-35 & Comparative Examples 3-1 to 3-11

Each of inventive resist compositions (R-01 to 35) and comparative resist compositions (R-36 to 46) was spin coated on a silicon wafer having an antireflective coating (ARC-29A, Nissan Chemical Co., Ltd.) of 90 nm thick and baked at 100° C. for 60 seconds to form a resist film of 100 nm thick. A resist protective coating material (SIOC-3, Shin-Etsu Chemical Co., Ltd.) was spin coated on the resist film and heat treated at 90° C. for 60 seconds to form a protective film of 50 nm thick. Using an ArF immersion excimer laser stepper (Nikon Corp., NA 1.30), the wafer was exposed to a certain pattern drawn on a 6% halftone phase shift mask for pattern transfer. The wafer was post-exposure baked (PEB) for 60 seconds, and puddle developed with a 2.38 wt % TMAH aqueous solution for 30 seconds, forming a line-and-space pattern. During the PEB, an optimum temperature for each resist composition was employed.

The pattern-bearing wafer thus obtained was observed under a top-down scanning electron microscope (TDSEM). The line width of the 40-nm 1:1 line-and-space pattern transferred was measured to determine the dependence of line width on exposure dose. The optimum exposure dose was defined as an exposure dose (mJ/cm$^2$) at which lines with a width of 40 nm were formed. An exposure dose tolerance which provided a line width of 40 nm±10% was then determined. The exposure dose tolerance divided by the optimum exposure dose, expressed in percent, represents an exposure latitude. A greater value indicates a smaller dimensional change with varying exposure dose, that is, better exposure latitude. As the measure of mask fidelity, the line width formed in the resist film at the optimum exposure dose is plotted relative to the line width in the mask, from which a gradient is computed by linear approximation and reported as a mask error enhancement factor (MEEF). A smaller value of MEEF is better because it indicates a higher mask fidelity and minimizes the influence of finish errors in the mask pattern. Furthermore, for roughness comparison, the line width was measured at 100 equally spaced-apart points in the line length 2-μm range of the 40-nm 1:1 line-and-space pattern. A 3σ value of these measurements was then computed and reported as line width roughness (LWR). A smaller value of LWR is better because it indicates smaller roughness.

The test results of the resist compositions are tabulated in Table 3.

As seen from the results in Table 3, the resist compositions within the scope of the invention are improved in resolution performance when processed by the ArF excimer laser lithography. A comparison between Comparative Examples 3-1, 3-2, 3-3, 3-4 and Examples 3-1, 3-2, 3-3, 3-4, 3-5, 3-6 reveals that a difference in resolution performance arises from the presence or absence of spirocyclic structure in the acid-labile ester monomer and the position of spirocycle bond. A further improvement in resolution is achieved when the polymer

TABLE 3

|  |  | Resist composition | PEB temp., °C. | Optimum dose, mJ/cm$^2$ | Exposure latitude, % | MEEF | LWR, nm |
|---|---|---|---|---|---|---|---|
| Example | 3-1 | R-01 | 100 | 33 | 12 | 4.0 | 6.3 |
|  | 3-2 | R-02 | 105 | 35 | 14 | 3.4 | 5.8 |
|  | 3-3 | R-03 | 110 | 36 | 16 | 3.2 | 5.9 |
|  | 3-4 | R-04 | 110 | 39 | 18 | 3.2 | 5.8 |
|  | 3-5 | R-05 | 110 | 42 | 20 | 3.1 | 5.6 |
|  | 3-6 | R-06 | 115 | 40 | 16 | 3.6 | 6.1 |
|  | 3-7 | R-07 | 95 | 33 | 18 | 2.4 | 5.8 |
|  | 3-8 | R-08 | 100 | 39 | 15 | 3.3 | 5.9 |
|  | 3-9 | R-09 | 90 | 38 | 16 | 2.5 | 5.7 |
|  | 3-10 | R-10 | 100 | 34 | 16 | 2.9 | 5.9 |
|  | 3-11 | R-11 | 85 | 36 | 18 | 2.8 | 5.6 |
|  | 3-12 | R-12 | 95 | 35 | 15 | 2.8 | 5.8 |
|  | 3-13 | R-13 | 90 | 32 | 18 | 2.6 | 5.5 |
|  | 3-14 | R-14 | 80 | 33 | 20 | 2.4 | 5.3 |
|  | 3-15 | R-15 | 100 | 35 | 19 | 3.0 | 5.9 |
|  | 3-16 | R-16 | 90 | 35 | 19 | 2.8 | 5.6 |
|  | 3-17 | R-17 | 95 | 37 | 18 | 2.7 | 5.7 |
|  | 3-18 | R-18 | 80 | 40 | 18 | 2.5 | 5.4 |
|  | 3-19 | R-19 | 80 | 33 | 16 | 2.6 | 5.3 |
|  | 3-20 | R-20 | 80 | 30 | 22 | 2.2 | 6.2 |
|  | 3-21 | R-21 | 90 | 28 | 12 | 3.3 | 5.8 |
|  | 3-22 | R-22 | 85 | 27 | 11 | 2.9 | 5.9 |
|  | 3-23 | R-23 | 100 | 33 | 14 | 2.8 | 5.5 |
|  | 3-24 | R-24 | 90 | 31 | 17 | 2.5 | 5.4 |
|  | 3-25 | R-25 | 105 | 29 | 12 | 3.2 | 6.0 |
|  | 3-26 | R-26 | 95 | 34 | 18 | 2.7 | 5.3 |
|  | 3-27 | R-27 | 95 | 36 | 16 | 2.9 | 6.1 |
|  | 3-28 | R-28 | 90 | 36 | 18 | 2.6 | 5.8 |
|  | 3-29 | R-29 | 95 | 38 | 16 | 2.5 | 5.3 |
|  | 3-30 | R-30 | 85 | 33 | 20 | 2.5 | 5.8 |
|  | 3-31 | R-31 | 90 | 35 | 16 | 3.0 | 6.2 |
|  | 3-32 | R-32 | 105 | 30 | 15 | 3.1 | 6.0 |
|  | 3-33 | R-33 | 105 | 29 | 16 | 2.9 | 5.9 |
|  | 3-34 | R-34 | 85 | 33 | 12 | 3.1 | 6.3 |
|  | 3-35 | R-35 | 100 | 42 | 20 | 2.3 | 5.6 |
| Comparative Example | 3-1 | R-36 | 115 | 35 | 9 | 4.5 | 7.2 |
|  | 3-2 | R-37 | 120 | 34 | 10 | 4.1 | 6.9 |
|  | 3-3 | R-38 | 115 | 31 | 11 | 4.0 | 6.8 |
|  | 3-4 | R-39 | 115 | 36 | 10 | 3.8 | 6.9 |
|  | 3-5 | R-40 | 105 | 33 | 10 | 3.9 | 6.8 |
|  | 3-6 | R-41 | 110 | 37 | 11 | 4.0 | 6.6 |
|  | 3-7 | R-42 | 95 | 32 | 8 | 4.3 | 6.5 |
|  | 3-8 | R-43 | 110 | 27 | 7 | 4.5 | 7.5 |
|  | 3-9 | R-44 | 100 | 30 | 10 | 4.2 | 6.7 |
|  | 3-10 | R-45 | 100 | 35 | 11 | 3.6 | 7.2 |
|  | 3-11 | R-46 | 95 | 32 | 8 | 3.4 | 7.2 |

3. PEB Temperature Dependence

Examples 4-1 to 4-3 & Comparative Examples 4-1 to 4-3

In the test of evaluating the 40-nm 1:1 line-and-space patterns of Examples 3-1 to 3-35 and Comparative Examples 3-1 to 3-11, it was also examined at the optimum exposure dose how the line width depended on the PEB temperature.

Samples in Table 4 were selected from inventive resist compositions (R-01 to 35) and comparative resist compositions (R-36 to 46) in Example 1. For each resist composition, the PEB temperature was varied at intervals of 2° C. in the range of optimum PEB temperature±4° C. The line width is plotted relative to the PEB temperature, from which a gradient (nm/° C.) was computed by fitting of the linear approximate expression to the least square method. A smaller gradient is better because PEB temperature dependence is so reduced to suppress the dimensional change caused by a difference in thermal history on the wafer surface.

The test results are tabulated in Table 4.

TABLE 4

|  | Resist composition | Gradient, nm/° C. |
| --- | --- | --- |
| Example 4-1 | R-02 | 4.6 |
| Example 4-2 | R-07 | 3.5 |
| Example 4-3 | R-08 | 4.1 |
| Comparative Example 4-1 | R-37 | 6.0 |
| Comparative Example 4-2 | R-38 | 5.5 |
| Comparative Example 4-3 | R-39 | 5.8 |

It is evident from Table 4 that the resist compositions within the scope of the invention are reduced in PEB temperature dependence.

The invention claimed is:

1. An acid-labile ester monomer having a spirocyclic structure, represented by the general formula (2):

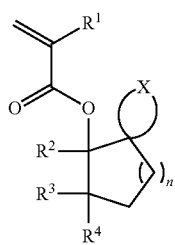

(2)

wherein X is a divalent group which forms a substituted or unsubstituted cyclopentane, cyclohexane or norbornane ring with the carbon atom to which it is attached, $R^1$ is hydrogen, fluorine, methyl or trifluoromethyl, $R^2$ is a straight, branched or cyclic $C_1$-$C_{10}$ monovalent hydrocarbon group, $R^3$ and $R^4$ are each independently hydrogen or a straight, branched or cyclic $C_1$-$C_{10}$ monovalent hydrocarbon group, or $R^3$ and $R^4$, taken together, stand for a divalent group which forms a substituted or unsubstituted cyclopentane or cyclohexane ring with the carbon atom to which they are attached, and n is 1 or 2.

2. The acid-labile ester monomer of claim 1 which is selected from the group consisting of monomers having the following formulae:

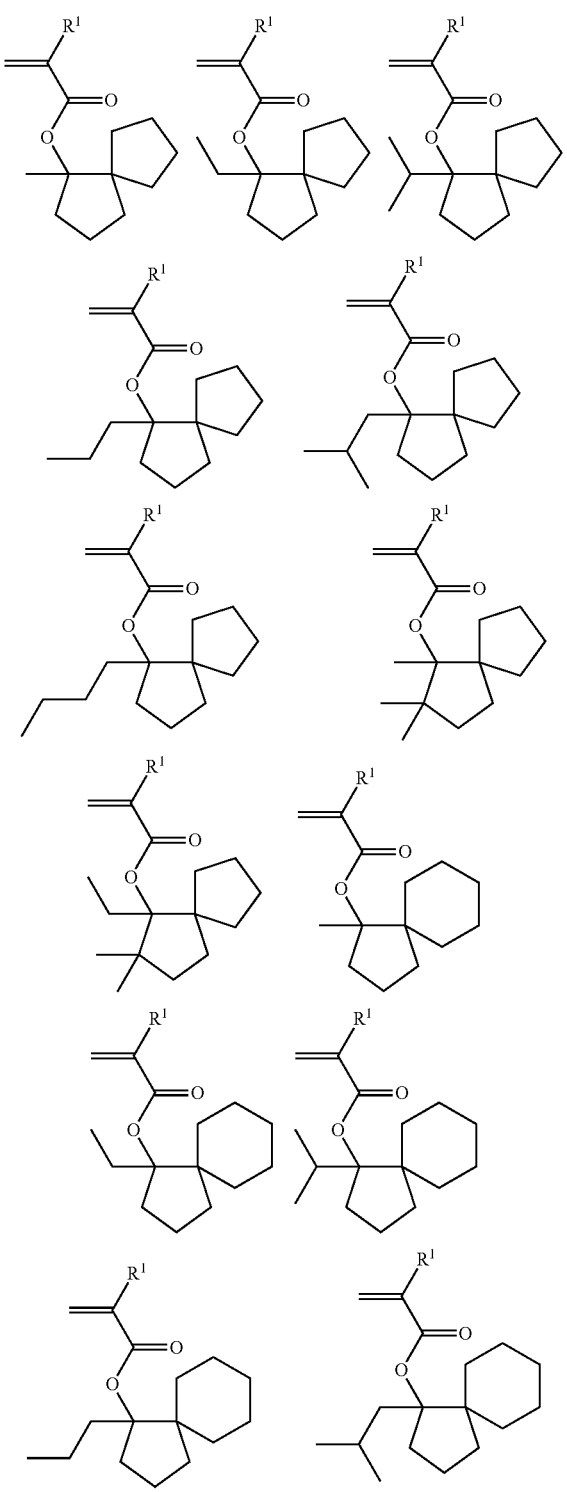

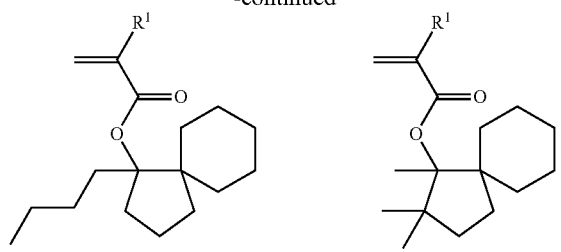
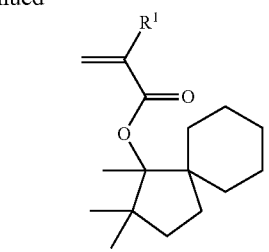
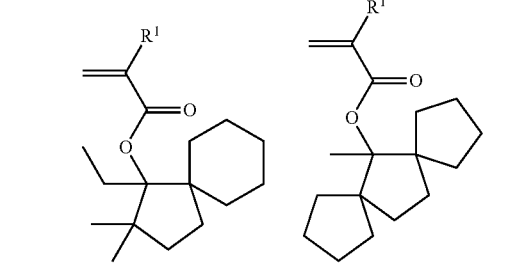
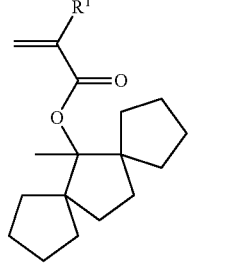
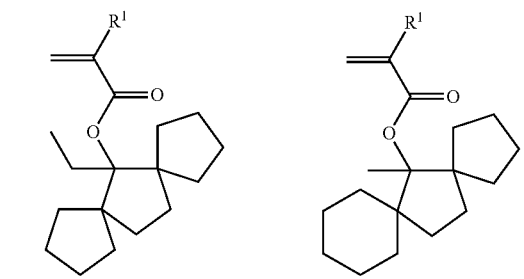
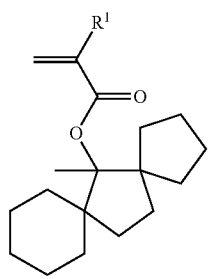
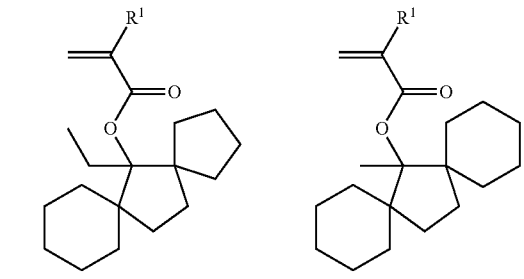
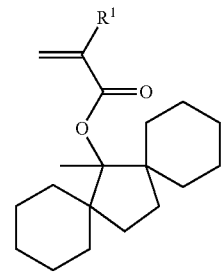
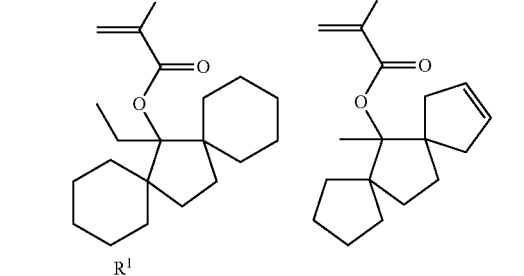
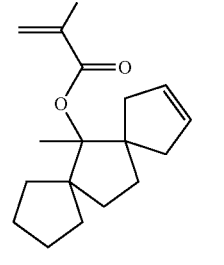
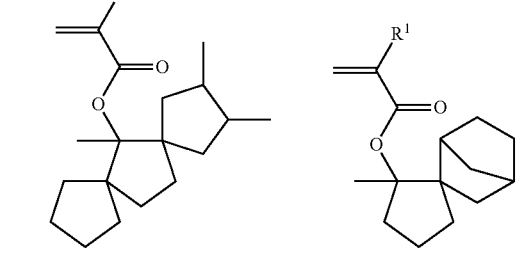
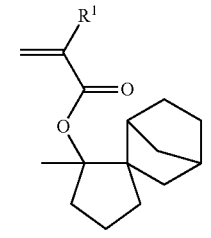
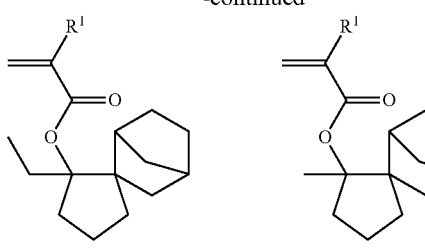
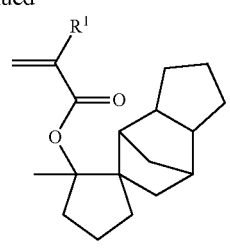
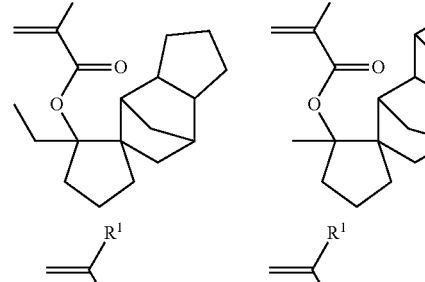
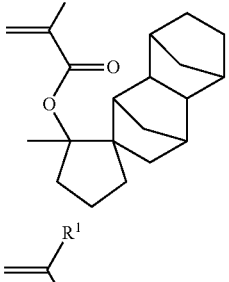
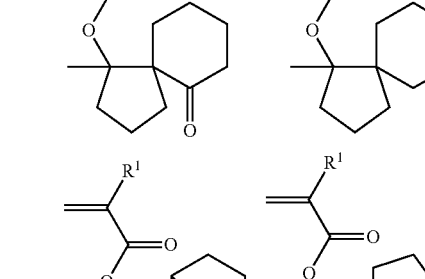
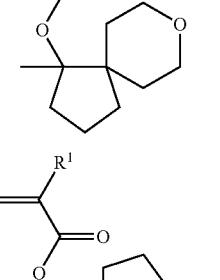
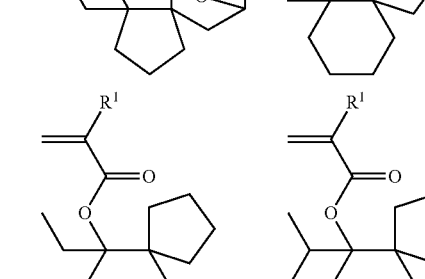
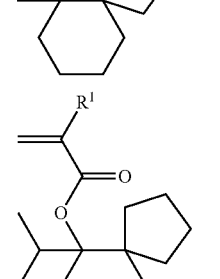
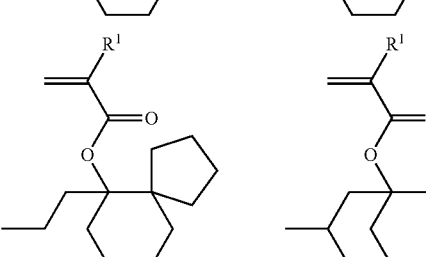
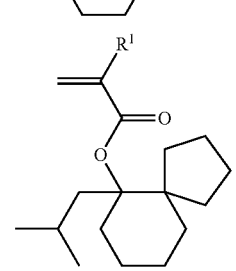
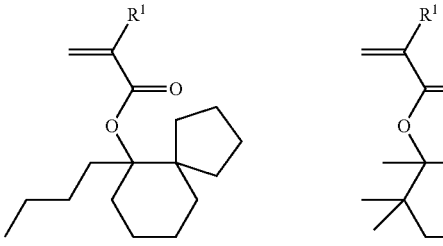
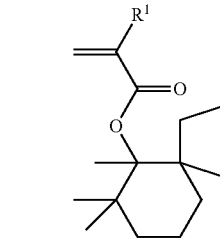

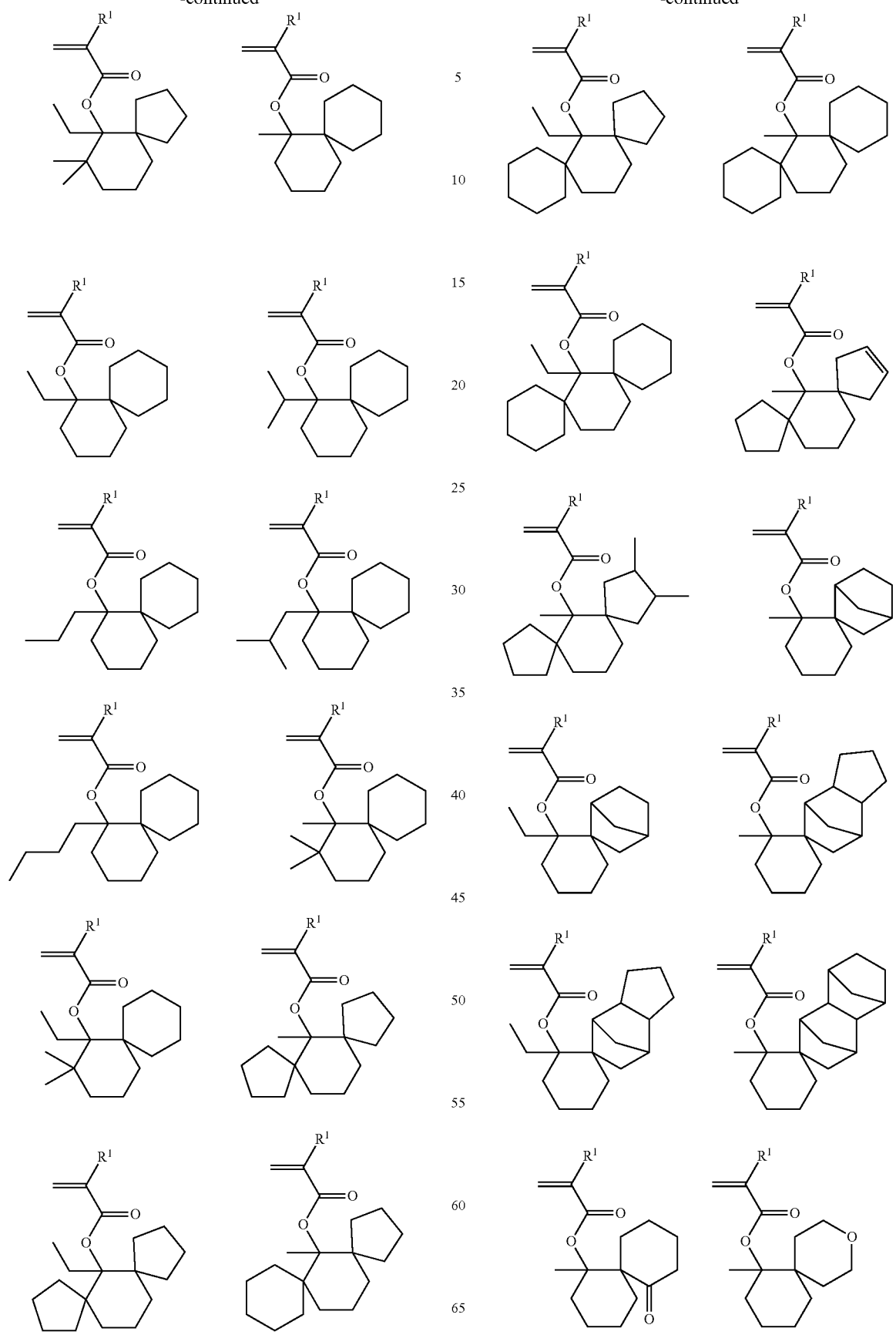

-continued

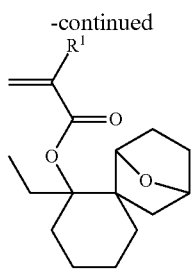

wherein R¹ is hydrogen, fluorine, methyl or trifluoromethyl.

3. A polymer comprising recurring units having the general formula (2a), which is derived from the acid-labile ester monomer having a spirocyclic structure of claim 1:

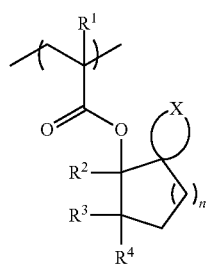

(2a)

wherein X is a divalent group which forms a substituted or unsubstituted cyclopentane, cyclohexane or norbornane ring with the carbon atom to which it is attached, R¹ is hydrogen, fluorine, methyl or trifluoromethyl, R² is a straight, branched or cyclic $C_1$-$C_{10}$ monovalent hydrocarbon group, R³ and R⁴ are each independently hydrogen or a straight, branched or cyclic $C_1$-$C_{10}$ monovalent hydrocarbon group, or R³ and R⁴, taken together, stand for a divalent group which forms a substituted or unsubstituted cyclopentane or cyclohexane ring with the carbon atom to which they are attached, and n is 1 or 2.

4. A resist composition comprising the polymer of claim 3 as a base resin and a compound capable of generating an acid in response to actinic light or radiation.

5. The resist composition of claim 4, wherein the compound capable of generating an acid in response to actinic light or radiation is a sulfonium salt compound having the general formula (4):

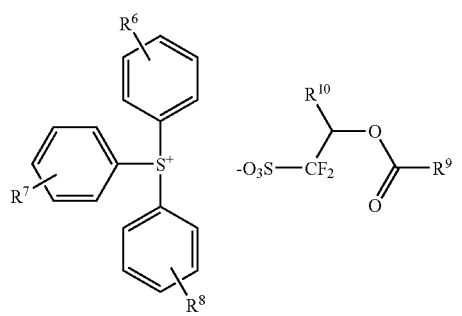

(4)

wherein R⁶, R⁷, and R⁸ are each independently hydrogen, a straight, branched or cyclic $C_1$-$C_{20}$ monovalent hydrocarbon group which may contain a heteroatom, $C_1$-$C_{10}$ alkoxy group or halogen, R⁹ is a straight, branched or cyclic $C_1$-$C_{30}$ monovalent hydrocarbon group which may contain a heteroatom, and R¹⁰ is hydrogen or trifluoromethyl.

6. A process for forming a pattern, comprising the steps of applying the resist composition of claim 4 onto a substrate, heat treating, exposing to high-energy radiation or electron beam through a photomask, optionally heat treating, and developing with a developer.

7. A process for forming a pattern, comprising the steps of applying the resist composition of claim 5 onto a substrate, heat treating, exposing to high-energy radiation or electron beam through a photomask, optionally heat treating, and developing with a developer.

8. The polymer of claim 3 which is selected from the group consisting of polymers derived from monomers having the following formulae:

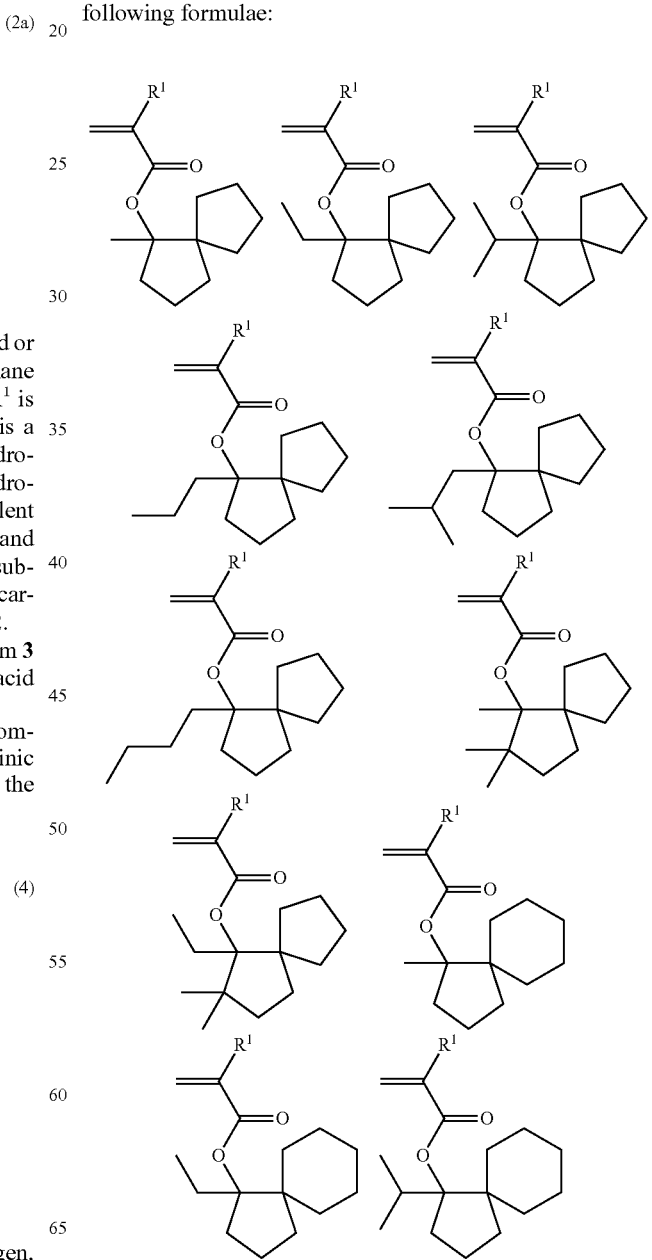

-continued
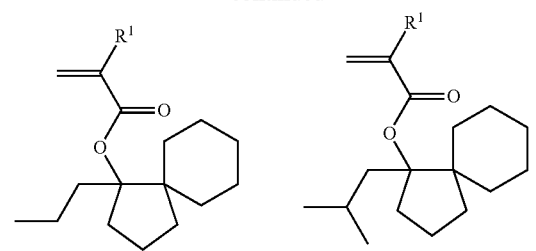
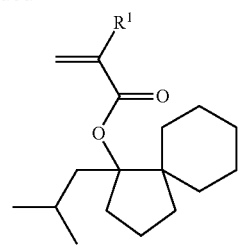
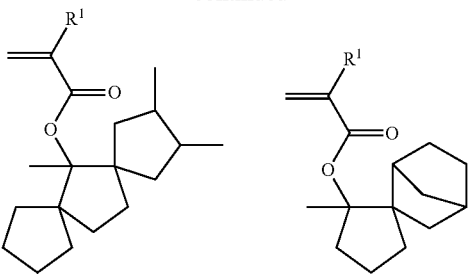
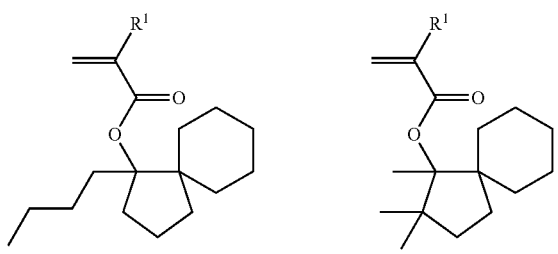
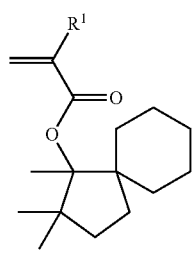
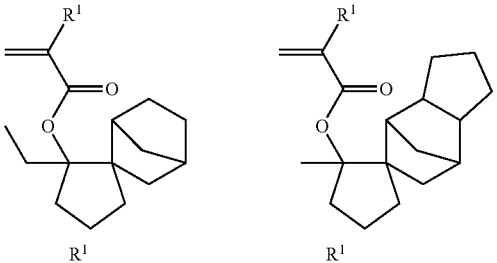
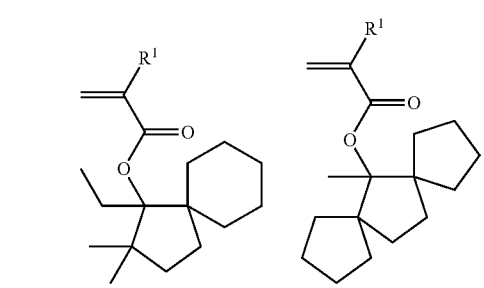
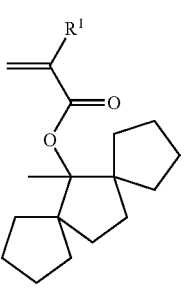
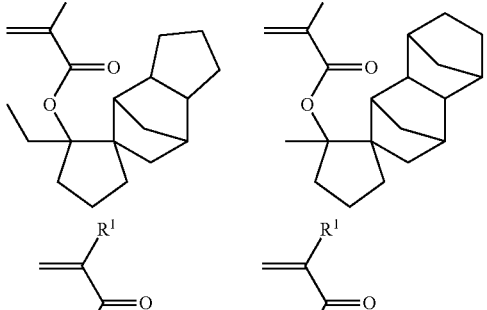
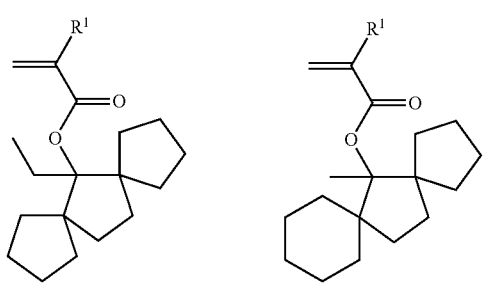
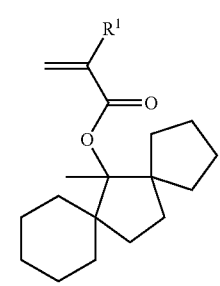
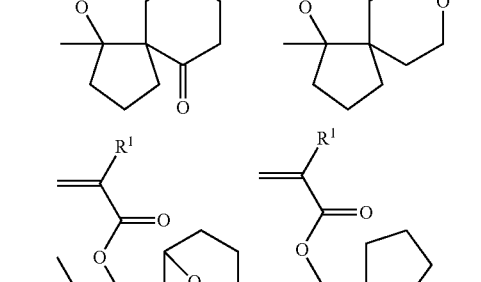
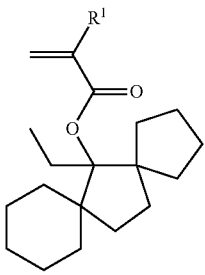
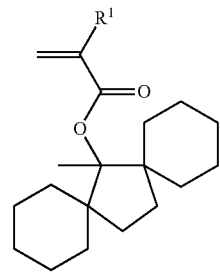
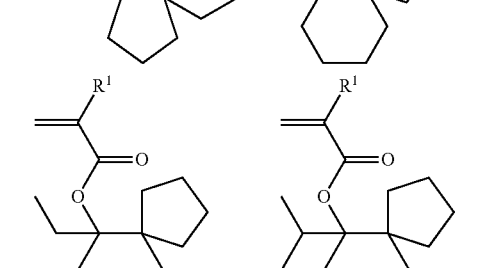
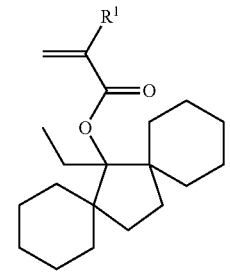
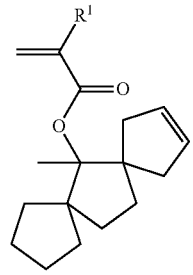
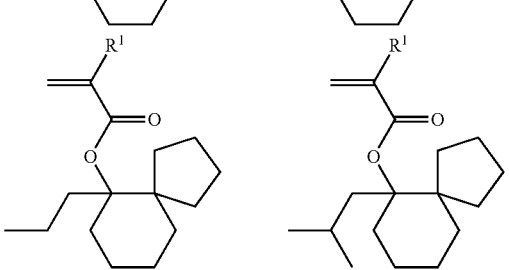

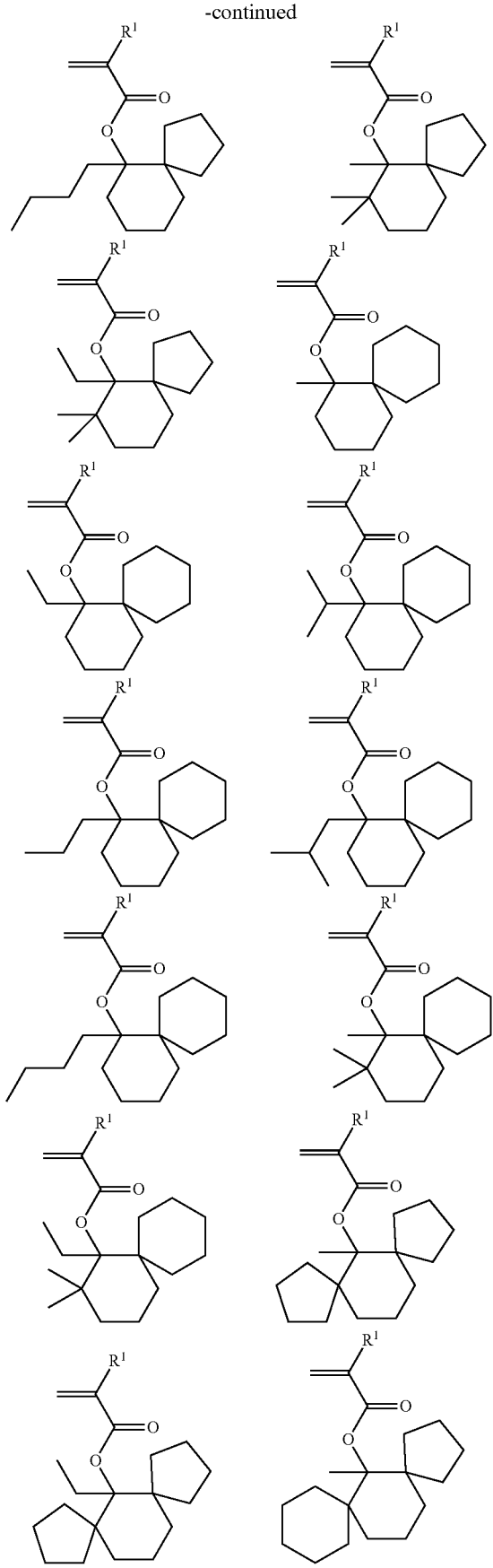
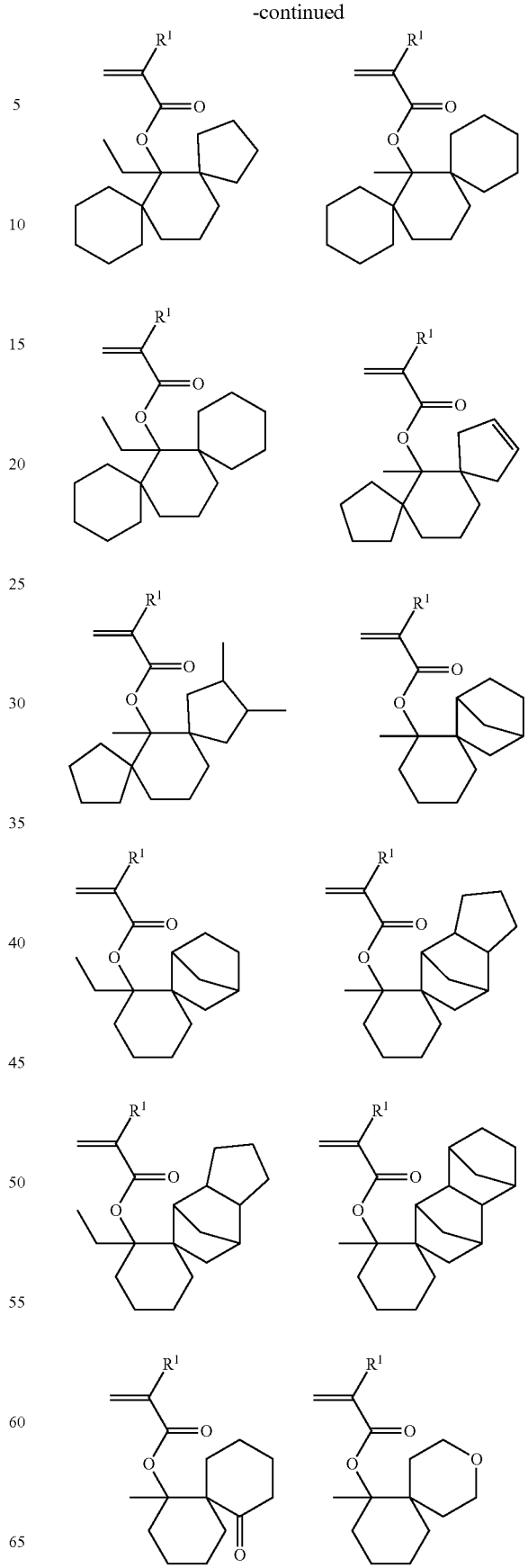

-continued

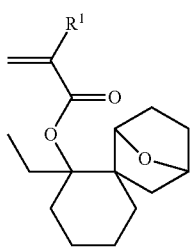

wherein $R^1$ is hydrogen, fluorine, methyl or trifluoromethyl.

9. A resist composition comprising the polymer of claim 8 as a base resin and a compound capable of generating an acid in response to actinic light or radiation.

10. A resist composition comprising the polymer of claim 8 and a sulfonium salt compound having the general formula (4) as a compound capable of generating an acid in response to actinic light or radiation:

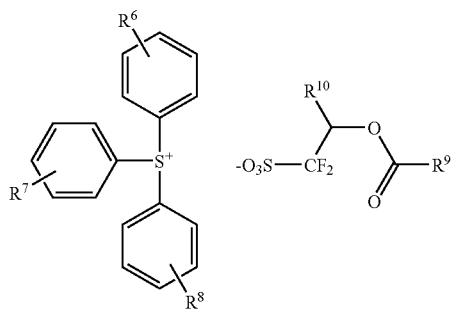

(4)

wherein $R^6$, $R^7$, and $R^8$ are each independently hydrogen, a straight, branched or cyclic $C_1$-$C_{20}$ monovalent hydrocarbon group which may contain a heteroatom, $C_1$-$C_{10}$alkoxy group or halogen, $R^9$ is a straight, branched or cyclic $C_1$-$C_{30}$ monovalent hydrocarbon group which may contain a heteroatom, and $R^{10}$ is hydrogen or trifluoromethyl.

11. A process for forming a pattern, comprising the steps of applying a resist composition comprising the polymer of claim 8 onto a substrate, heat treating, exposing to high-energy radiation or electron beam through a photomask, optionally heat treating, and developing with a developer.

* * * * *